US008883915B2

(12) United States Patent
Myung et al.

(10) Patent No.: US 8,883,915 B2
(45) Date of Patent: Nov. 11, 2014

(54) HYDROPHOBIC AND HYDROPHILIC INTERPENETRATING POLYMER NETWORKS DERIVED FROM HYDROPHOBIC POLYMERS AND METHODS OF PREPARING THE SAME

(75) Inventors: David Myung, Santa Clara, CA (US); Michael J. Jaasma, San Francisco, CA (US); Lampros Kourtis, Berkeley, CA (US); Daniel Chang, Danville, CA (US); Curtis W. Frank, Cupertino, CA (US)

(73) Assignee: Biomimedica, Inc., Germantown, TN (US)

( * ) Notice: Subject to any disclaimer, the term of this patent is extended or adjusted under 35 U.S.C. 154(b) by 285 days.

(21) Appl. No.: 13/219,348

(22) Filed: Aug. 26, 2011

(65) Prior Publication Data

US 2012/0045651 A1 Feb. 23, 2012

Related U.S. Application Data

(63) Continuation-in-part of application No. 12/499,041, filed on Jul. 7, 2009, now abandoned.

(60) Provisional application No. 61/078,741, filed on Jul. 7, 2008, provisional application No. 61/079,060, filed on Jul. 8, 2008, provisional application No. 61/095,273, filed on Sep. 8, 2008, provisional application No. 61/166,194, filed on Apr. 2, 2009, provisional application No. 61/377,844, filed on Aug. 27, 2010, provisional application No. 61/383,705, filed on Sep. 16, 2010.

(51) Int. Cl.
*C08G 18/42* (2006.01)
*C08G 18/08* (2006.01)
(Continued)

(52) U.S. Cl.
CPC . *C08L 75/04* (2013.01); *A61K 6/09* (2013.01); *C08G 18/831* (2013.01);
(Continued)

(58) Field of Classification Search
CPC ....... A61F 2/0063; A61L 31/16; B23B 27/08; A61B 17/00; C08L 23/00; C08L 2203/00; C08G 18/42
USPC ......... 524/589, 564, 562, 560, 543, 507, 501, 524/500, 1; 525/50, 55, 60; 521/106
See application file for complete search history.

(56) References Cited

U.S. PATENT DOCUMENTS 3,030,327 A * 4/1962 Hosch ........................... 524/706
(Continued)

FOREIGN PATENT DOCUMENTS

EP 1779875 A1 5/2007
GB 2372707 A 9/2002
(Continued)

OTHER PUBLICATIONS

Jones et al. (Journal of Materials Science: Materials in Medicine vol. 8 1997 pp. 713-717).*
(Continued)

*Primary Examiner* — Patrick Ryan
*Assistant Examiner* — Aaron Greso
(74) *Attorney, Agent, or Firm* — Shay Glenn LLP

(57) ABSTRACT

A composition of matter comprising a hydrophobic or hydrophilic (or both) interpenetrating polymer network containing a non-ionic/ionic polymer and a hydrophobic thermoset or thermoplastic polymer, articles made from such composition and methods of preparing such articles. The invention also includes a process for preparing a hydrophobic/hydrophilic IPN or semi-IPN from a hydrophobic thermoset or thermoplastic polymer including the steps of placing an non-ionizable/ionizable monomer solution in contact with a hydrophobic thermoset or thermoplastic polymer; diffusing the monomer solution into the hydrophobic thermoset or thermoplastic polymer; and polymerizing the monomers to form a penetrating polymer inside the hydrophobic thermoset or thermoplastic polymer, thereby forming the IPN or semi-IPN.

40 Claims, 63 Drawing Sheets

(51) Int. Cl.

| | |
|---|---|
| *C08L 75/00* | (2006.01) |
| *A61K 9/16* | (2006.01) |
| *C08L 31/02* | (2006.01) |
| *D06M 15/263* | (2006.01) |
| *C08L 75/04* | (2006.01) |
| *A61K 6/09* | (2006.01) |
| *C08G 18/83* | (2006.01) |
| *C08L 75/06* | (2006.01) |
| *C08L 75/16* | (2006.01) |
| *C08L 33/12* | (2006.01) |
| *C08L 33/02* | (2006.01) |

(52) U.S. Cl.
CPC .............. *C08L 75/06* (2013.01); *C08L 75/16* (2013.01); *C08L 33/12* (2013.01); *C08G 2270/00* (2013.01); *C08L 33/02* (2013.01)
USPC .............. 524/589; 524/1; 524/500; 524/507; 524/543; 524/564; 525/50; 525/55; 525/60; 521/106

(56) References Cited

U.S. PATENT DOCUMENTS

| | | | |
|---|---|---|---|
| 3,053,251 A | 9/1962 | Black et al. | |
| 3,702,611 A | 11/1972 | Fishbein | |
| 3,826,678 A | 7/1974 | Hoffman et al. | |
| 3,833,404 A | 9/1974 | Sperling et al. | |
| 3,939,049 A | 2/1976 | Ratner et al. | |
| 4,035,848 A | 7/1977 | Wagner | |
| 4,128,600 A | 12/1978 | Skinner et al. | |
| 4,192,827 A | 3/1980 | Mueller et al. | |
| 4,224,699 A | 9/1980 | Weber | |
| 4,302,553 A | 11/1981 | Frisch et al. | |
| 4,312,079 A | 1/1982 | Dorre et al. | |
| 4,320,709 A | 3/1982 | Hladun | |
| 4,391,797 A | 7/1983 | Folkman et al. | |
| 4,423,099 A | 12/1983 | Mueller et al. | |
| 4,439,583 A | 3/1984 | Gould et al. | |
| 4,452,925 A | 6/1984 | Kuzma et al. | |
| 4,468,499 A | 8/1984 | Siegfried et al. | |
| 4,477,604 A | 10/1984 | Oechsle, III | |
| 4,487,865 A | 12/1984 | Balazs et al. | |
| 4,500,676 A | 2/1985 | Balazs et al. | |
| 4,502,161 A | 3/1985 | Wall | |
| 4,536,554 A | 8/1985 | Lim et al. | |
| 4,575,539 A | 3/1986 | DeCrosta et al. | |
| 4,621,637 A | 11/1986 | Fishbein | |
| 4,678,468 A | 7/1987 | Hiroyoshi | |
| 4,680,336 A | 7/1987 | Larsen et al. | |
| 4,693,715 A | 9/1987 | Abel, Jr. | |
| 4,836,884 A | 6/1989 | McAuslan | |
| 4,846,841 A | 7/1989 | Oh | |
| 4,865,601 A | 9/1989 | Caldwell et al. | |
| 4,913,144 A | 4/1990 | Del Medico | |
| 4,931,287 A | 6/1990 | Bae et al. | |
| 4,966,934 A | 10/1990 | Huang et al. | |
| 4,973,493 A | 11/1990 | Guire | |
| 4,978,352 A | 12/1990 | Fedorov et al. | |
| 5,030,230 A | 7/1991 | White | |
| 5,067,961 A | 11/1991 | Kelman et al. | |
| 5,087,392 A | 2/1992 | Burke et al. | |
| 5,094,876 A | 3/1992 | Goldberg et al. | |
| 5,100,689 A | 3/1992 | Goldberg et al. | |
| 5,112,350 A | 5/1992 | Civerchia et al. | |
| 5,115,056 A | 5/1992 | Mueller et al. | |
| 5,122,133 A | 6/1992 | Evans | |
| 5,133,769 A | 7/1992 | Wagner et al. | |
| 5,171,318 A | 12/1992 | Gibson et al. | |
| 5,258,024 A | 11/1993 | Chavel et al. | |
| 5,264,495 A | 11/1993 | Irie et al. | |
| 5,276,070 A | 1/1994 | Arroyo | |
| 5,282,851 A | 2/1994 | Jacob-LaBarre | |
| 5,290,548 A | 3/1994 | Goldberg | |
| 5,300,116 A | 4/1994 | Chirila et al. | |
| 5,314,478 A | 5/1994 | Oka et al. | |
| 5,374,515 A | 12/1994 | Parenteau et al. | |
| 5,403,893 A | 4/1995 | Tanaka et al. | |
| 5,476,515 A | 12/1995 | Kelman | |
| 5,556,429 A | 9/1996 | Felt | |
| 5,562,738 A | 10/1996 | Boyd et al. | |
| 5,589,563 A | 12/1996 | Ward | |
| 5,591,170 A | 1/1997 | Spievack et al. | |
| 5,643,390 A | 7/1997 | Don et al. | |
| 5,644,049 A | 7/1997 | Giusti et al. | |
| 5,645,592 A | 7/1997 | Nicolais et al. | |
| 5,656,210 A | 8/1997 | Hill et al. | |
| 5,660,692 A | 8/1997 | Nesburn et al. | |
| 5,674,942 A | 10/1997 | Hill et al. | |
| 5,693,034 A | 12/1997 | Buscemi et al. | |
| 5,716,633 A | 2/1998 | Civerchia | |
| 5,763,529 A | 6/1998 | Lucas | |
| 5,770,669 A | 6/1998 | Robertson et al. | |
| 5,800,412 A * | 9/1998 | Zhang et al. ................. 604/523 |
| 5,824,079 A | 10/1998 | Siegler et al. | |
| 5,836,313 A | 11/1998 | Perez et al. | |
| 5,856,366 A | 1/1999 | Shiveley et al. | |
| 5,904,927 A | 5/1999 | Amiji | |
| 5,913,858 A | 6/1999 | Calandruccio et al. | |
| 5,962,005 A | 10/1999 | Saga et al. | |
| 5,976,648 A | 11/1999 | Li et al. | |
| 6,001,894 A | 12/1999 | Ottersbach et al. | |
| 6,005,160 A | 12/1999 | Hsiue et al. | |
| 6,027,742 A | 2/2000 | Lee et al. | |
| 6,031,017 A | 2/2000 | Waki et al. | |
| 6,057,406 A | 5/2000 | Pojman et al. | |
| 6,120,904 A | 9/2000 | Hostettler et al. | |
| 6,160,084 A | 12/2000 | Langer et al. | |
| 6,171,300 B1 | 1/2001 | Adams | |
| 6,210,438 B1 | 4/2001 | Sheets, Jr. et al. | |
| 6,214,044 B1 | 4/2001 | Silverstrini | |
| 6,221,467 B1 | 4/2001 | Nazarova et al. | |
| 6,224,893 B1 | 5/2001 | Langer et al. | |
| 6,231,605 B1 | 5/2001 | Ku | |
| 6,231,611 B1 | 5/2001 | Mosseri | |
| 6,239,209 B1 | 5/2001 | Yang et al. | |
| 6,251,965 B1 | 6/2001 | Wang et al. | |
| 6,254,637 B1 | 7/2001 | Lee et al. | |
| 6,264,695 B1 | 7/2001 | Stoy | |
| 6,265,016 B1 | 7/2001 | Hostettler et al. | |
| 6,281,271 B1 | 8/2001 | Rumphorst et al. | |
| 6,306,177 B1 | 10/2001 | Felt et al. | |
| 6,331,578 B1 | 12/2001 | Turner et al. | |
| 6,368,315 B1 * | 4/2002 | Gillis et al. ................. 604/523 |
| 6,372,815 B1 | 4/2002 | Sulc et al. | |
| 6,376,742 B1 | 4/2002 | Zdrahala et al. | |
| 6,388,043 B1 | 5/2002 | Langer et al. | |
| 6,391,055 B1 | 5/2002 | Ikada et al. | |
| 6,428,576 B1 | 8/2002 | Haldimann | |
| 6,437,018 B1 | 8/2002 | Gertzman et al. | |
| 6,440,444 B2 | 8/2002 | Boyce et al. | |
| 6,479,565 B1 | 11/2002 | Stanley | |
| 6,482,209 B1 | 11/2002 | Engh et al. | |
| 6,494,917 B1 | 12/2002 | McKellop et al. | |
| 6,509,098 B1 | 1/2003 | Merrill et al. | |
| 6,610,067 B2 | 8/2003 | Tallarida et al. | |
| 6,629,997 B2 | 10/2003 | Mansmann | |
| 6,632,235 B2 | 10/2003 | Weikel et al. | |
| 6,632,246 B1 | 10/2003 | Simon et al. | |
| 6,645,715 B1 | 11/2003 | Griffith et al. | |
| 6,652,587 B2 | 11/2003 | Felt et al. | |
| 6,673,079 B1 | 1/2004 | Kane | |
| 6,673,112 B2 | 1/2004 | Nigam | |
| 6,679,917 B2 | 1/2004 | Ek | |
| 6,689,165 B2 | 2/2004 | Jacob et al. | |
| 6,726,322 B2 | 4/2004 | Andino et al. | |
| 6,733,533 B1 | 5/2004 | Lozier | |
| 6,740,087 B2 | 5/2004 | Knox | |
| 6,755,865 B2 | 6/2004 | Tarabishy | |
| 6,846,875 B2 | 1/2005 | Pennings et al. | |
| 6,852,125 B2 | 2/2005 | Simon et al. | |
| 6,866,936 B2 | 3/2005 | Opolski | |
| 6,911,212 B2 | 6/2005 | Gertzman et al. | |
| 6,918,914 B2 | 7/2005 | Bauer | |

(56) References Cited

U.S. PATENT DOCUMENTS

| | | |
|---|---|---|
| 6,921,264 B2 | 7/2005 | Mayer et al. |
| 6,949,251 B2 | 9/2005 | Dalal et al. |
| RE38,839 E | 10/2005 | Magnante |
| 6,953,594 B2 | 10/2005 | Lee et al. |
| 6,955,540 B2 | 10/2005 | Mayer et al. |
| 6,960,617 B2 | 11/2005 | Omidian et al. |
| 6,976,997 B2 | 12/2005 | Noolandi et al. |
| 7,008,226 B2 | 3/2006 | Mayer et al. |
| 7,008,635 B1 | 3/2006 | Coury et al. |
| 7,018,460 B2 | 3/2006 | Xu et al. |
| 7,019,192 B2 | 3/2006 | Gertzman et al. |
| 7,029,479 B2 | 4/2006 | Tallarida et al. |
| 7,037,984 B2 | 5/2006 | Lendlein et al. |
| 7,049,351 B2 | 5/2006 | Phelan et al. |
| 7,066,958 B2 | 6/2006 | Ferree |
| 7,083,650 B2 | 8/2006 | Moskowitz et al. |
| 7,094,286 B2 | 8/2006 | Liu |
| 7,105,026 B2 | 9/2006 | Johnson et al. |
| 7,160,305 B2 | 1/2007 | Schmieding |
| 7,163,541 B2 | 1/2007 | Ek |
| 7,176,247 B1 | 2/2007 | Walker, Jr. |
| 7,204,897 B2 | 4/2007 | Stoy et al. |
| 7,217,294 B2 | 5/2007 | Kusanagi et al. |
| 7,235,592 B2 | 6/2007 | Muratoglu et al. |
| 7,279,174 B2 | 10/2007 | Pacetti et al. |
| 7,279,507 B2 | 10/2007 | Hu et al. |
| 7,303,814 B2 | 12/2007 | Lamberti et al. |
| 7,335,205 B2 | 2/2008 | Aeschlimann et al. |
| 7,341,593 B2 | 3/2008 | Auxepaules et al. |
| 7,371,257 B2 | 5/2008 | Sahatjian et al. |
| 7,387,810 B2 | 6/2008 | Hossainy |
| 7,468,075 B2 | 12/2008 | Lang et al. |
| 7,476,398 B1 | 1/2009 | Doillon et al. |
| 7,563,483 B2 | 7/2009 | Hossainy et al. |
| 7,618,462 B2 | 11/2009 | Ek |
| 7,678,151 B2 | 3/2010 | Ek |
| 7,713,305 B2 | 5/2010 | Ek |
| 7,824,666 B2 | 11/2010 | Wolff et al. |
| 2002/0055007 A1* | 5/2002 | Soane et al. .................. 428/520 |
| 2002/0082699 A1 | 6/2002 | Ward et al. |
| 2002/0091229 A1 | 7/2002 | Hubbell et al. |
| 2002/0173855 A1 | 11/2002 | Mansmann |
| 2002/0198280 A1 | 12/2002 | Baba et al. |
| 2003/0022216 A1 | 1/2003 | Mao et al. |
| 2003/0083389 A1 | 5/2003 | Kao et al. |
| 2003/0092777 A1 | 5/2003 | Leitner |
| 2003/0100666 A1 | 5/2003 | DeGroot et al. |
| 2003/0114936 A1 | 6/2003 | Sherwood et al. |
| 2003/0130741 A1 | 7/2003 | McMinn |
| 2003/0153981 A1 | 8/2003 | Wang et al. |
| 2003/0170308 A1 | 9/2003 | Cleary et al. |
| 2004/0028804 A1 | 2/2004 | Anderson et al. |
| 2004/0034437 A1 | 2/2004 | Schmieding |
| 2004/0044410 A1 | 3/2004 | Ferree et al. |
| 2004/0059425 A1 | 3/2004 | Schmieding |
| 2004/0116564 A1 | 6/2004 | Devlin et al. |
| 2004/0133275 A1 | 7/2004 | Mansmann |
| 2004/0134502 A1 | 7/2004 | Mizuno et al. |
| 2004/0138382 A1 | 7/2004 | Dous |
| 2004/0139382 A1 | 7/2004 | Kim |
| 2004/0147466 A1 | 7/2004 | Barman et al. |
| 2004/0147927 A1 | 7/2004 | Tsougarakis et al. |
| 2004/0153040 A1 | 8/2004 | Martineau et al. |
| 2004/0153079 A1 | 8/2004 | Tsougarakis et al. |
| 2004/0153163 A1 | 8/2004 | Posner |
| 2004/0167528 A1 | 8/2004 | Schantz |
| 2004/0171740 A1 | 9/2004 | Ruberti et al. |
| 2004/0199250 A1 | 10/2004 | Fell |
| 2004/0204760 A1 | 10/2004 | Fitz et al. |
| 2004/0214914 A1 | 10/2004 | Marmo |
| 2004/0230315 A1 | 11/2004 | Ek |
| 2004/0236424 A1 | 11/2004 | Berez et al. |
| 2004/0266941 A1 | 12/2004 | Houston et al. |
| 2004/0267363 A1 | 12/2004 | Fell et al. |
| 2005/0004306 A1 | 1/2005 | Lubnin et al. |
| 2005/0013793 A1 | 1/2005 | Beckman et al. |
| 2005/0027364 A1 | 2/2005 | Kim et al. |
| 2005/0038520 A1 | 2/2005 | Binette et al. |
| 2005/0049459 A1 | 3/2005 | Hern |
| 2005/0055044 A1 | 3/2005 | Kangas |
| 2005/0065616 A1 | 3/2005 | Ankorina-Stark et al. |
| 2005/0090612 A1 | 4/2005 | Soane et al. |
| 2005/0113836 A1 | 5/2005 | Lozier et al. |
| 2005/0113928 A1 | 5/2005 | Cragg et al. |
| 2005/0126680 A1 | 6/2005 | Aeschlimann et al. |
| 2005/0142162 A1 | 6/2005 | Hunter et al. |
| 2005/0147685 A1 | 7/2005 | Osada et al. |
| 2005/0171604 A1 | 8/2005 | Michalow |
| 2005/0187146 A1 | 8/2005 | Helmus et al. |
| 2005/0215660 A1 | 9/2005 | Tomikawa et al. |
| 2005/0218541 A1 | 10/2005 | Peng et al. |
| 2005/0228161 A1 | 10/2005 | Benz et al. |
| 2005/0251267 A1 | 11/2005 | Winterbottom et al. |
| 2005/0251268 A1 | 11/2005 | Truncale |
| 2005/0267482 A1 | 12/2005 | Hyde, Jr. |
| 2005/0267584 A1 | 12/2005 | Burdulis, Jr. et al. |
| 2005/0278025 A1 | 12/2005 | Ku et al. |
| 2005/0283255 A1 | 12/2005 | Geremakis et al. |
| 2005/0287187 A1 | 12/2005 | Mansmann |
| 2006/0008506 A1 | 1/2006 | De Sousa et al. |
| 2006/0052878 A1 | 3/2006 | Schmieding |
| 2006/0083773 A1 | 4/2006 | Myung et al. |
| 2006/0105295 A1 | 5/2006 | Mayer et al. |
| 2006/0111726 A1 | 5/2006 | Felt et al. |
| 2006/0122543 A1 | 6/2006 | Mayer et al. |
| 2006/0134186 A1 | 6/2006 | Carlton et al. |
| 2006/0142406 A1 | 6/2006 | Schmitt et al. |
| 2006/0188487 A1 | 8/2006 | Thomas et al. |
| 2006/0188940 A1 | 8/2006 | Cima et al. |
| 2006/0224244 A1 | 10/2006 | Thomas et al. |
| 2006/0233855 A1 | 10/2006 | Seliktar et al. |
| 2006/0235517 A1 | 10/2006 | Hodorek |
| 2006/0235539 A1 | 10/2006 | Blunn et al. |
| 2006/0235542 A1 | 10/2006 | Hodorek et al. |
| 2006/0241759 A1 | 10/2006 | Trieu |
| 2006/0246241 A1 | 11/2006 | Kruger et al. |
| 2006/0282169 A1 | 12/2006 | Felt et al. |
| 2006/0287721 A1 | 12/2006 | Myung et al. |
| 2006/0287730 A1 | 12/2006 | Segal et al. |
| 2007/0014828 A1 | 1/2007 | Fitzhugh et al. |
| 2007/0016211 A1 | 1/2007 | Botimer |
| 2007/0048382 A1 | 3/2007 | Meyer et al. |
| 2007/0067032 A1 | 3/2007 | Felt et al. |
| 2007/0068816 A1 | 3/2007 | Solomon et al. |
| 2007/0078388 A1 | 4/2007 | Kangas |
| 2007/0078518 A1 | 4/2007 | Lavi |
| 2007/0083266 A1 | 4/2007 | Lang |
| 2007/0088444 A1 | 4/2007 | Hodorek et al. |
| 2007/0098675 A1 | 5/2007 | Elisseeff et al. |
| 2007/0099840 A1 | 5/2007 | Ulijn et al. |
| 2007/0100457 A1 | 5/2007 | Hyde, Jr. et al. |
| 2007/0118218 A1 | 5/2007 | Hooper |
| 2007/0126982 A1 | 6/2007 | Myung et al. |
| 2007/0134291 A1 | 6/2007 | Ting et al. |
| 2007/0135922 A1 | 6/2007 | Trieu |
| 2007/0141108 A1 | 6/2007 | Thomas et al. |
| 2007/0149441 A1 | 6/2007 | Aeschlimann et al. |
| 2007/0167541 A1 | 7/2007 | Ruberti et al. |
| 2007/0179605 A1 | 8/2007 | Myung et al. |
| 2007/0179607 A1 | 8/2007 | Hodorek et al. |
| 2007/0179622 A1 | 8/2007 | Denoziere et al. |
| 2007/0191963 A1 | 8/2007 | Winterbottom et al. |
| 2007/0198022 A1 | 8/2007 | Lang et al. |
| 2007/0202148 A1 | 8/2007 | Ringeisen et al. |
| 2007/0224238 A1 | 9/2007 | Mansmann et al. |
| 2007/0225823 A1 | 9/2007 | Hawkins et al. |
| 2007/0233240 A1 | 10/2007 | Frank et al. |
| 2007/0233269 A1 | 10/2007 | Steines et al. |
| 2007/0265704 A1 | 11/2007 | Mayer et al. |
| 2007/0270783 A1 | 11/2007 | Zumsteg et al. |
| 2007/0276394 A1 | 11/2007 | Johnson et al. |
| 2008/0058954 A1 | 3/2008 | Trieu |
| 2008/0070086 A1 | 3/2008 | Fukuchi et al. |
| 2008/0077249 A1 | 3/2008 | Gradel |

(56) References Cited

U.S. PATENT DOCUMENTS

| | | | |
|---|---|---|---|
| 2008/0103505 A1* | 5/2008 | Fransen | 606/92 |
| 2008/0124376 A1 | 5/2008 | Pruitt et al. | |
| 2008/0241214 A1 | 10/2008 | Myung et al. | |
| 2008/0269370 A1 | 10/2008 | Myung et al. | |
| 2008/0317818 A1 | 12/2008 | Griffith et al. | |
| 2009/0035344 A1 | 2/2009 | Thomas et al. | |
| 2009/0062408 A1 | 3/2009 | Liu et al. | |
| 2009/0062423 A1 | 3/2009 | Betz et al. | |
| 2009/0088846 A1 | 4/2009 | Myung et al. | |
| 2009/0142508 A1 | 6/2009 | Lai | |
| 2009/0163860 A1 | 6/2009 | Patrick et al. | |
| 2009/0176891 A1 | 7/2009 | Chogle et al. | |
| 2009/0209966 A1 | 8/2009 | Chandler | |
| 2009/0221730 A1 | 9/2009 | Kowalski et al. | |
| 2009/0233887 A1 | 9/2009 | Shalaby et al. | |
| 2009/0240337 A1 | 9/2009 | Myung et al. | |
| 2010/0010114 A1 | 1/2010 | Myung et al. | |
| 2010/0032090 A1 | 2/2010 | Myung et al. | |
| 2010/0056646 A1 | 3/2010 | Shalaby et al. | |
| 2010/0125341 A1 | 5/2010 | Frauens | |
| 2011/0152868 A1 | 6/2011 | Kourtis et al. | |
| 2013/0096691 A1 | 4/2013 | Myung et al. | |
| 2013/0103157 A1 | 4/2013 | Kourtis et al. | |

FOREIGN PATENT DOCUMENTS

| | | |
|---|---|---|
| JP | 06-287443 A | 10/1994 |
| JP | 09-077809 A | 3/1997 |
| JP | 10-500038 | 1/1998 |
| JP | 2002-514233 A | 5/2002 |
| JP | 2002-518564 A | 6/2002 |
| JP | 2002-518565 A | 6/2002 |
| JP | 2003-171475 A | 6/2003 |
| WO | WO 94/01468 A1 | 1/1994 |
| WO | WO 00/02937 A1 | 1/2000 |
| WO | WO00/43050 A1 | 7/2000 |
| WO | WO02/26848 A2 | 4/2002 |
| WO | WO 2004/055057 A1 | 7/2004 |
| WO | WO 2004/091685 A2 | 10/2004 |
| WO | WO2007/067697 A2 | 6/2007 |
| WO | WO 2007/112305 A2 | 10/2007 |
| WO | WO 2009/071937 A1 | 6/2009 |
| WO | WO2010/037685 | 4/2010 |
| WO | WO 2010/059495 A2 | 5/2010 |

OTHER PUBLICATIONS

MIT.Edu (http://web.mit.edu/course/3/3.11/www/modules/props.pdf Feb. 8, 2007}.*
Van Landuyt (Bone vol. 25 No. 2 sup. 1, Aug. 1999 pp. 96S-98S).*
Chen (Yingyong Huaxue 1995 vol. 12 No. 4 pp. 66-69 with English Abstract).*
Lam et al. (Urology vol. 64 pp. 9-15 2004).*
Real Dictionary—implant—Princeton Uni Princeton NJ Available May 26, 2003 {http://www.realdictionary.com/?q=implant}.*
Nuerosurgical (Nuerosurgical.com spinal_anatomy (C) 2007 Taken as Sep. 18, 2008) {http://www.neurosurgical.com/neuro_medical_info/spinal_anatomy.html}.*
Christenson et al.; Antioxidant inhibition of poly(carbonate urethane) in vivo biodegradation; J Biomed Mater Res; 76(3); pp. 480-490; Mar. 2006.
Gorna et al.; Biodegradable porous polyurethane scaffolds for tissue repair and regeneration; J Biomed Mater Res; 79(1); pp. 128-138; Oct. 2006.
Bobyn et al., The optimum pore size for the fixation of porous-surfaced metal implants by the ingrowth of bone. Clin Orthop Relat Res, Jul./Aug. 1980(150): p. 263-70.
Borden et al.; The sintered microsphere matrix for bone tissue engineering: In vitroosteoconductivity studies; J. Biomed. Mat. Res.; 61(3); pp. 421-429; Sep. 2002.
Brodbeck et al., Biomaterial adherent macrophage apoptosis is increased by hydrophilic and anionic substrates in vivo. Proc Natl Acad Sci U S A, Aug. 6, 2002, 99(16): p. 10287-92.
Brown et al.; Solvent/Non-solvent sintering: A novel route to create porous microsphere scaffolds for tissue regeneration; J. Biomed. Mat. Res. (Part B: Applied Biomaterials); 868(2); pp. 396-406; Aug. 2008.
Covert et al.; Friction characteristics of a potential articular cartilage biomaterial. Wear, Aug. 2003. 255: p. 1064-1068.
Dror et al.; Gradient interpenetrating polymer networks. I. Poly(ether urethane) and polyacrylamide IPN; J of Applied Polymer Science; 26; pp. 1741-1757; Jun. 1981.
Elmer's Products Inc.; Material Safety Data Sheet; "Elmer's Nano Glue"; Jun. 13, 2007.
Elsabee et al.; Gradient interpenetrating polymer networks. II. Polyacrylamide gradients in poly(ether urethane); J of Applied Polymer Science; 28(7); pp. 2151-2166; Jun. 1983.
Evans et al.; The use of corneal organ culture in biocompatibility studies; Biomaterials; vol. 23; pp. 1359-1367; Mar. 2002.
Frank, Curt; Structure-property relationships for hydrogels with applications to biomedical devices; Presentation at American Chemical Society Mtg; San Francisco, CA; Sep. 11, 2006.
Gao et al.; Grafting of hydrophilic monomers onto polyurethane membranes by solution or pre-absorbing methods for acceleration of cell compatibility; Chinese Journal of Polymer Science; vol. 19; No. 5; pp. 493-498; Oct. 20, 2001.
Gong et al.; Double-network hydrogels with extremely high mechanical strength; Adv. Mater.; vol. 15; No. 14; pp. 1155-1158; Jul. 17, 2003.
Gorna et al.; Preparation, degradation, and clarification of biodegradable polyurethane foams for bone graft substitutes; J. Biomed Mater Res A; 67(3); pp. 813-827; Dec. 1, 2003.
Guelcher et al.; Synthesis and in vitro biocompatibility of injectable polyurethane foam scaffolds; Tissue Engineering; 12(5); pp. 1247-1259; May 2006.
Guelcher et al.; Synthesis of biocompatible segmented polyurethanes from aliphatic diisocyanates and diurea diol chain extenders; Acta biomaterialia; 1(4); pp. 471-484; Jul. 2005.
Gunatillake et al.; Designing biostable polyurethane elastomers for biomedical implants; Aust. J. Chem.; vol. 56; pp. 545-557; Jun. 2003.
Hern et al.; Incorporation of adhesion peptides into nonadhesive hydrogels useful for tissue resurfacing; J. Biomed. Materials Research; vol. 39; No. 1; pp. 266-276; Feb. 1998.
Iwasaki et al., Hydrogel like elastic membrane consisting of semi-interpenetrating polymer networks based on a phosphorylcholine polymer and a segmented polyurethane; J. Polym. Sd Part A: Polym Chem; 41; pp. 68-75; Jan. 2003.
Khan et al., Analysis and evaluation of a biomedical polycarbonate urethane tested in an in vitro study and an ovine arthroplasty model. Part I: materials selection and evaluation. Biomaterials, Feb. 2005. 26(6): p. 621-31.
Kim et al.; Water sorption of ploy(propylene glycol)/poly(acrylic acid) interpenetrating polymer network hydrogels; Reactive & Functional Polymers; vol. 55; pp. 69-73; Feb. 2003.
Kim et al.; Electrochemical behavior of an interpenetrating polymer network hydrogel composed of poly (propylene glycol) and poly(acrylic acid); Journal of Applied Polymer Science; vol. 89; pp. 2301-2305; Aug. 2003.
Lamba et al.; Polyurethanes in Biomedical Application; CRC Press; pp. 11, 14, 16, 18-20, 57-59, 73, 79 & 104; Nov. 1997.
Lee et al.; Interpenetrating polymer network hydrogels based on poly (ethylene glycol) macromer and chitosan; Carbohydrate Polymer; vol. 41; No. 2; pp. 197-205; Feb. 2000.
Lipatov et al.; Gradient interpenetrating polymer networks; Journal of Materials Science; 30(4); pp. 1095-1104; Feb. 1995.
Lu et al.; Release behavior of high molecular weight solutes from poly(ethylene glycol)-based degradable networks; Macromolecules; vol. 33(7); pp. 2509-2515; Mar. 2000.
Myung, David; Structure, properties, and medical device applications of mechanically enhanced, biometric hydrogel alloys; Doctoral Thesis; Stanford University; Dec. 2007.
Myung et al.; Biomimetic strain hardening in interpenetrating polymer network hydrogels; Polymer, ; vol. 48; No. 18; pp. 5376-5387; Jun. 2007.

(56) References Cited

OTHER PUBLICATIONS

Park et al.; Synthesis of PVA/PVP hydrogels having two-layer by radiation and their physical properties; Radiation Physics and Chemistry; 67(3-4); pp. 361-365; Jun. 2003.
Saito et al.; Preparation and properties of transparent cellulose hydrogels; J. Applied Polymer Science; 90(11); pp. 3020-3025; Dec. 2003.
Scholes at al.; Compliant layer acetabular cups: friction tsting of a range of materials and designs for a new generation of prosthesis that mimics the natural joint; Proc. IMechE; vol. 220(5); Part H; J. Engineering in Medicine; pp. 583-596, Jul. 2006.
Shalaby; U.S. Appl. No. 61/069,046 entitled "Hydroswellable, segmented, aliphatic polyurethanes and polyurethane ureas," filed Mar. 12, 2008.
Spector et al.; Porous polymers for biological fixation. Clin Orthop Relat Res, Oct. 1988 (235): p. 207-19.
Stammen et al., Mechanical properties of a novel PVA hydrogel in shear and unconfined compression. Biomaterials, Apr. 2001. 22(8): p. 799-806.
Tariq et al.; (Abstract) Sodium benzoate attenuates iminodipropionitrile-induced behavioral syndrome in rats. Behav pharmacol; Dec. 2004.
Tawfik, Dan; Amidation of carboxyl groups; The Protein Protocols Handbook, 2nd Ed.; Humana Press; pp. 477-478; Feb. 2002.
The Engineering Toolbox; Polyurethane Insulation: {http://www.engineeringtoolbox.com/polyurethane-insulation-k-values-d_1174.html} pp. 1-3; printed Oct. 21, 2011.
The Engineering Toolbox;Thermal conductivity of some common materials and gases: {http://www.engineeringtoolbox.com/thrmal-conductivity-d_429.html} pp. 1-2; printed Oct. 21, 2011.
The Gorilla Glue Company; Material Safety Data Sheet; "New Fast Cure-Dries White Gorilla Glue®"; Jan. 30, 2007.
The Gorilla Glue Company; Material Safety Data Sheet; "New Stronger-Faster Gorilla Glue®"; Jan. 26, 2007.
Yang et al.; Preparation of poly(acrylic acid) modified polyurethane membrane for biomaterial by UV radiation without degassing; J. Biomed. Mater. Res.; vol. 45(2); pp. 133-139; May 1999.
Yim et al., Biocompatibility of poly(ethylene glycol)/poly(acrylic acid)interpenetrating polymer network hydrogel particles inRAW 264.7 macrophage and MG-63 osteoblast cell lines. Journal of Biomedical Materials Research, 91A(3); pp. 894-902; Dec. 1, 2009.
Zhu et al.; (Abstract) Promoting the cytocompatibility of polyurethane scaffolds via surface photo-grafting polymerization of acrylamide; J. Mater. Sci. Mater. Med.; vol. 15; No. 3; pp. 283-289; Mar. 2004.
Myung et al.; U.S. Appl. No. 13/347,647 entitled "Orthopedic implants having gradient polymer alloys," filed Jan. 10, 2012.
Myung et al.; U.S. Appl. No. 13/418,294 entitled "Hydrogel Arthroplasty Device," filed Mar. 12, 2012.
Maroudas et al.; Permeability of articular cartilage; Nature; vol. 219 (5160); pp. 1260-1261; Sep. 21, 1968.
Mow et al., Basic Orthopaedic Biomechanics and Mechano-Biology, Lippincot Williams and Wilkins, 3rd Edition, Apr. 2005, pp. 459-461.
Wittemann et al.; Adsorption of proteins on spherical polyelectrolyte brushes in aqueous solution; Phys. Chem. Chem. Phys., Mar. 2003, vol. 5(8), pp. 1671-1677.
Wright et al., Wear studies on prosthetic materials using the pin-on-disc machine. Biomaterials, vol. 3, Issue 1, Jan. 1982, pp. 41-48.
Myung et al.; U.S. Appl. No. 13/542,464 entitled "Methods, Devices and Compositions for Adhering Hydrated Polymer Implants to Bone," filed Jul. 5, 2012.
Kim et al.; Electrical/pH Responsive Properties of Poly(2-acrylamido-2-methylpropane sulfonic acid)/Hyaluronic Acid Hydrogels; Journal of Applied Polymer Science; vol. 92; issue 3; pp. 1731-1736; May 2004.
Causton et al.; Dental materials: 1981 literature review Part 1; Journal of Dentistry; vol. 12; Issue 1; pp. 1R28; Mar. 1984.
Charnley, J.; Anchorage of the femoral head prosthesis to the shaft of the femur; J Bone Joint Surg Br.; 42-B:28-30; Feb. 1960.
Depuy Orthopaedics; Bone Cement Time Setting Chart; product file; date of publication unknown; available to applicants at least as of Jul. 2012.
Kanie et al.; Flexural properties of ethyl or methyl methacrylate-UDMA blend polymers; Dent Mater J; 29(5); pp. 575-581; Oct. 2010.
Kwong et al.; A comparison of the shrinkage of commercial bone cements when mixed under vacuum; J Bone Joint Surg Br.; 88(1):120-2; Jan. 2006.
Lewis G.; Properties of acrylic bone cement: state of the art review; J Biomed Mater Res.; 38(2):155-82; Summer(Jun.-Aug.) 1997.
Morgan et al.; Dependence of yield strain of human trabecular bone on anatomic site; J Biomech.; 34(5):569-77; May 2001.
Ohman et al.; Mechanical testing of cancellous bone from the femoral head: experimental errors due to off-axis measurements; J Biomech.; 40(11):2426-33; (year of publication is sufficiently earlier than the effective U.S. filing date and any foreign priority date) 2007.
Orr et al.; Shrinkage stresses in bone cement; Biomaterials; 24(17):2933-40; Aug. 2003.
Puska et al.; Exothermal Characteristics and Release of Residual Monomers from Fiber-reinforced Oligomer-modified Acrylic Bone Cement; J Biomat App; 20:51-64; Jul. 2005.
Stryker Orthopaedics; SimplexTM P Bone Cement; Product Literature LSB Rev. 3, Mar. 2006.
Kourtis et al.: U.S. Appl. No. 13/683,731 entitled "Systems, Devices, and Methods for Anchoring Orthopaedic Implants to Bone," filed Nov. 21, 2012.
Myung et al.; U.S. Appl. No. 13/748,573 entitled "Hydrophilic Interpenetrating Polymer Networks Derived From Hydrophobic Polymers," filed Jan. 23, 2013.
Myung et al.; U.S. Appl. No. 13/748,576 entitled "Hydrophilic Interpenetrating Polymer Networks Derived From Hydrophobic Polymers," filed Jan. 23, 2013.
Myung et al.; U.S. Appl. No. 13/816,537 entitled "Hydrophobic and Hydrophilic Interpenetrating Polymer Networks Derived From Hydrophobic Polymers and Methods of Preparing the Same," filed Apr. 24, 2013.
Myung et al.; U.S. Appl. No. 13/905,028 entitled "Polyurethane-grafted hydrogels," filed May 29, 2013.

* cited by examiner

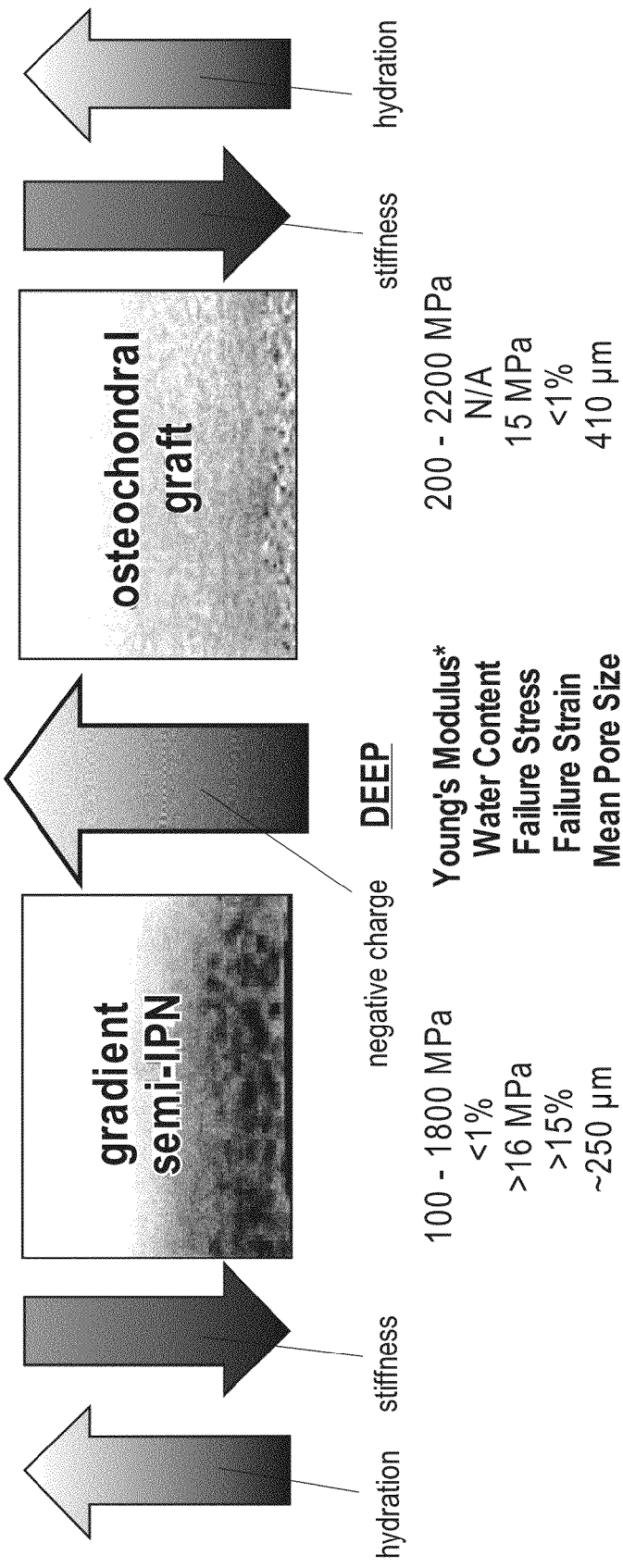

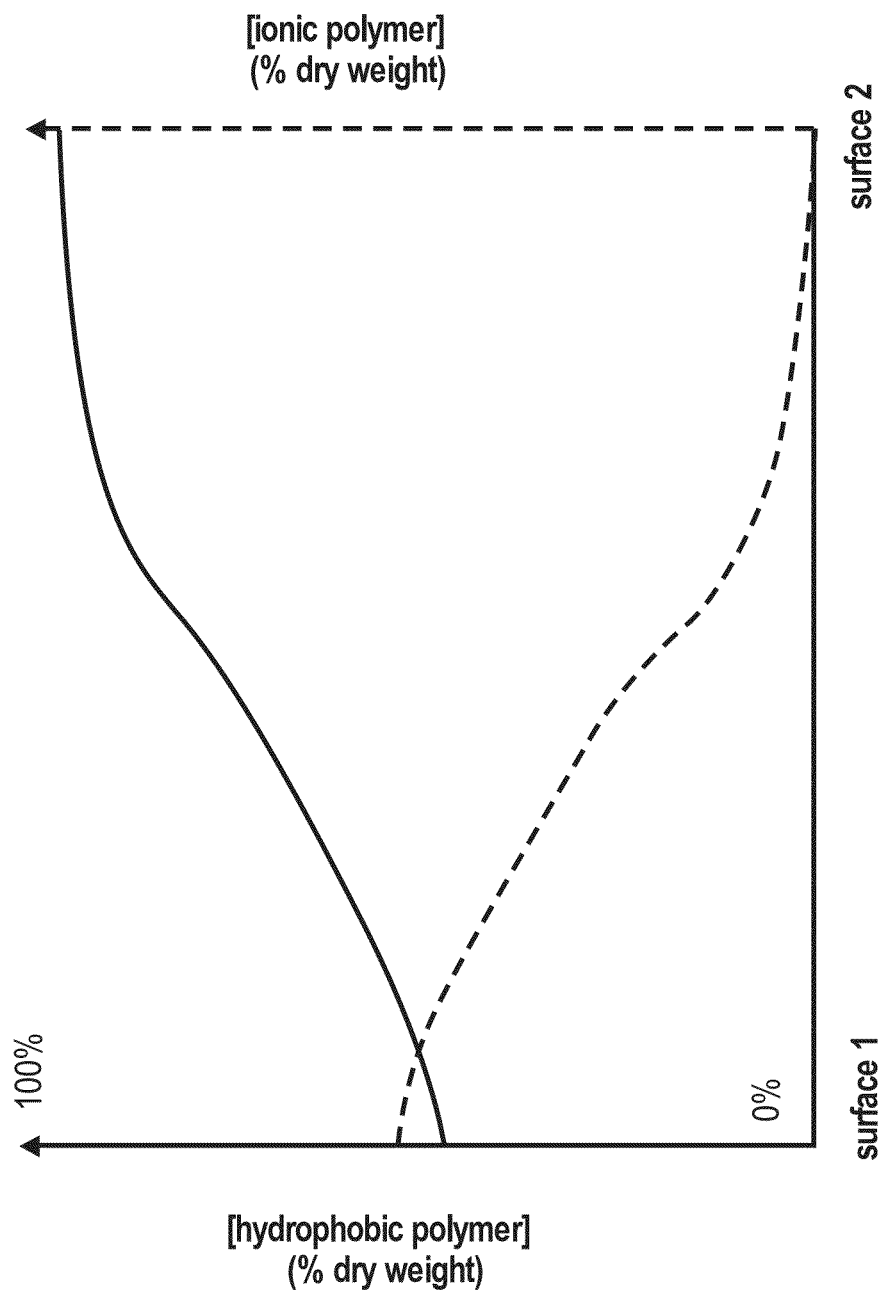

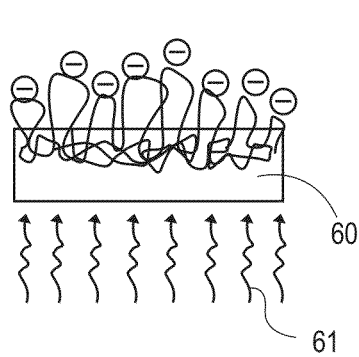 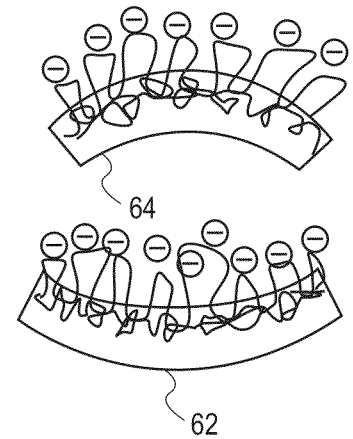
FIG. 6A    FIG. 6B
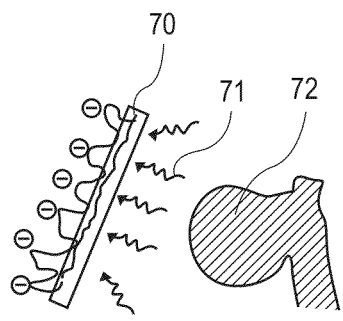 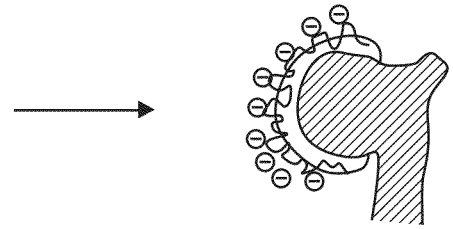
FIG. 7A    FIG. 7B
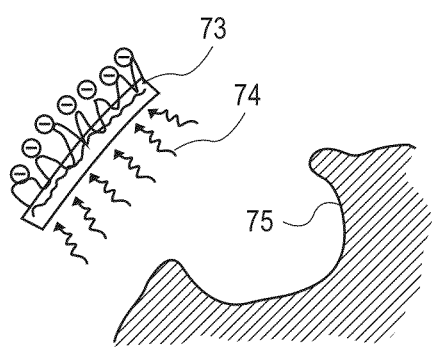 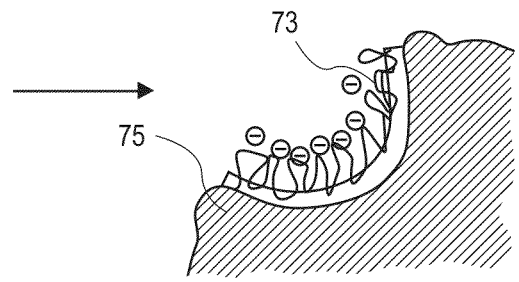
FIG. 7C    FIG. 7D

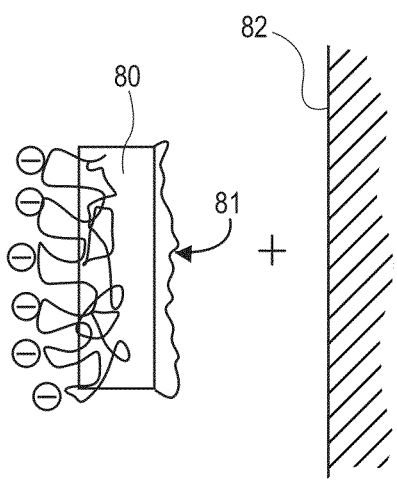 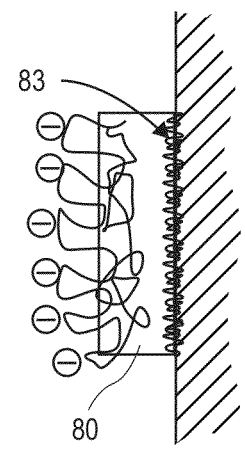
FIG. 8A    FIG. 8B
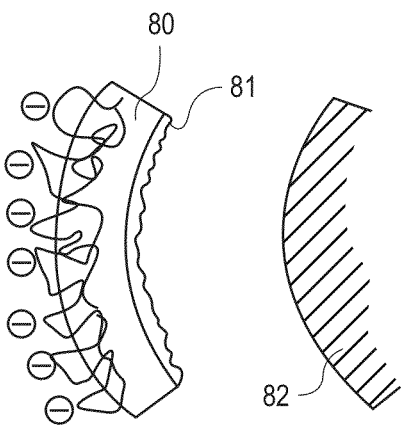 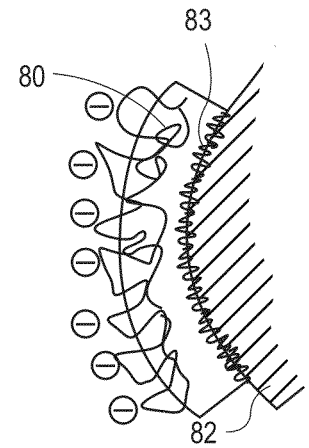
FIG. 8C    FIG. 8D

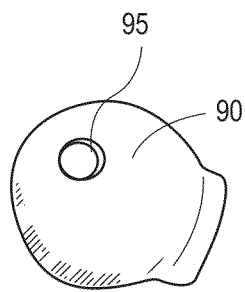
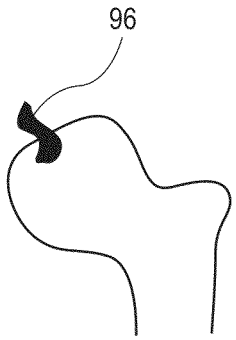
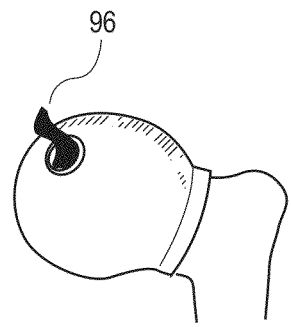
FIG. 10A  FIG. 10B
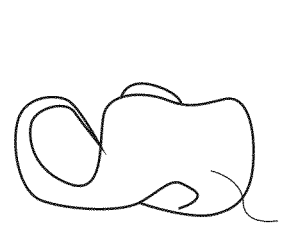
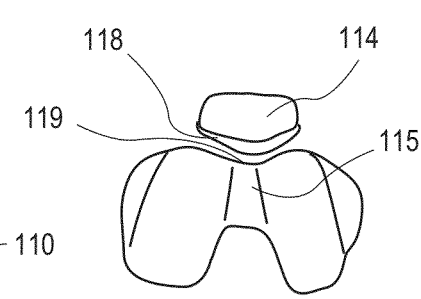
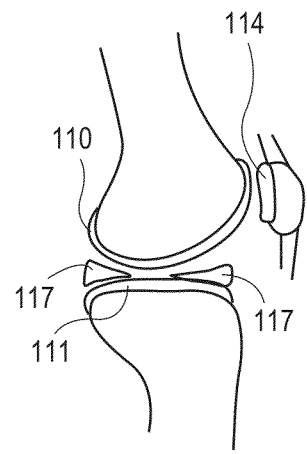
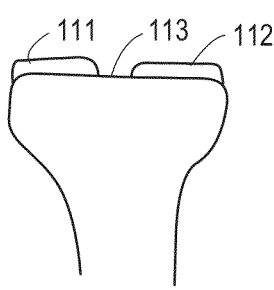
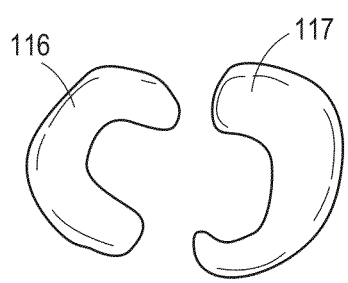
FIG. 11A  FIG. 11C
FIG. 11E
FIG. 11B  FIG. 11D

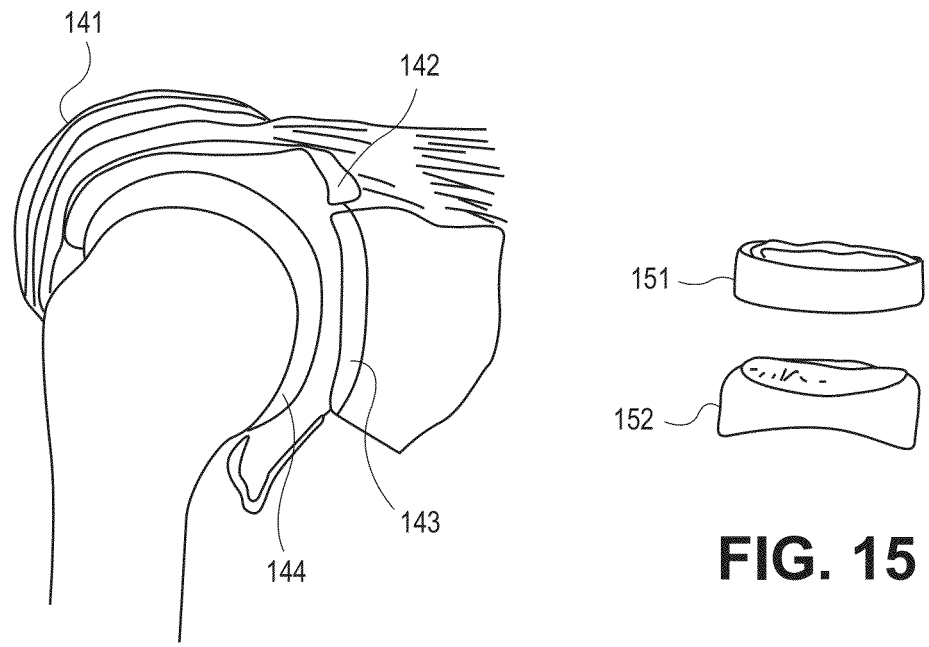
FIG. 14
FIG. 15
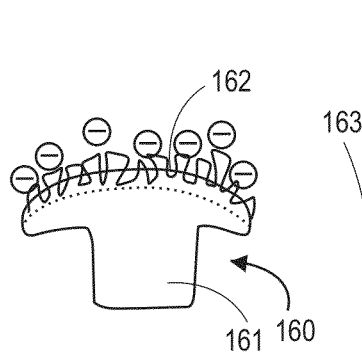 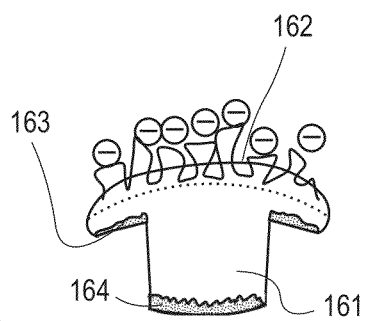 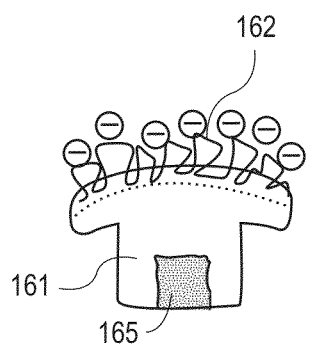
FIG. 16A  FIG. 16B  FIG. 16C
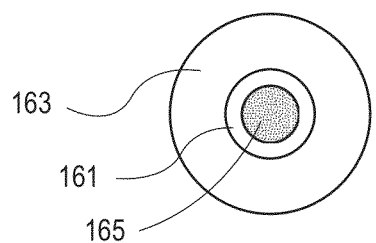
FIG. 16D

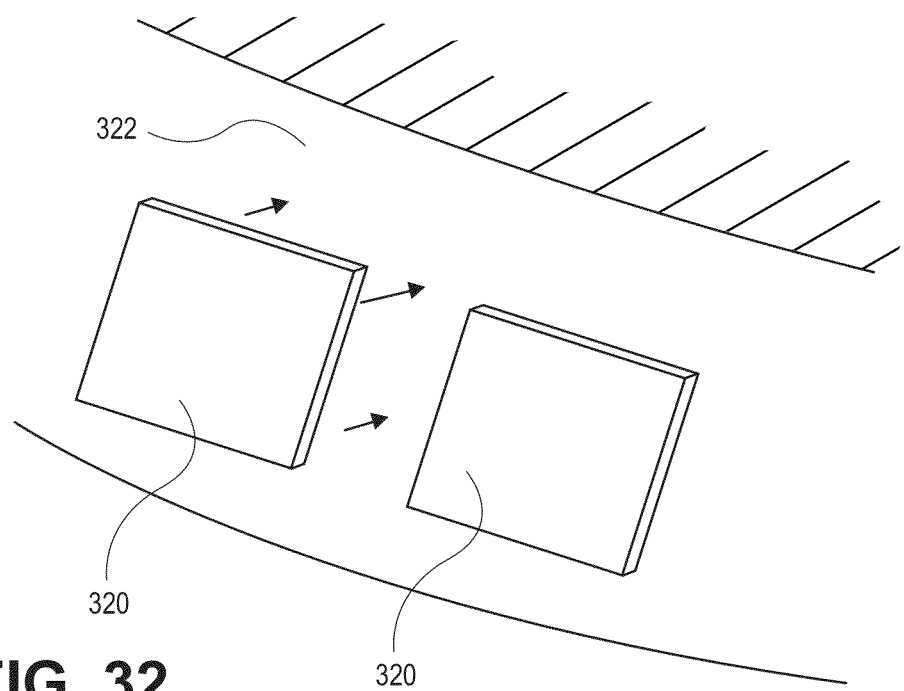
FIG. 32
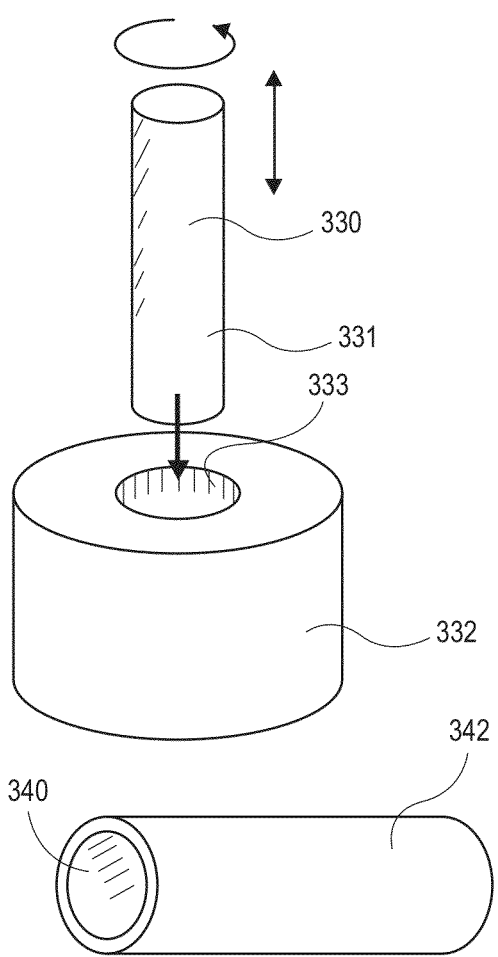
FIG. 33
FIG. 34

FIG. 38
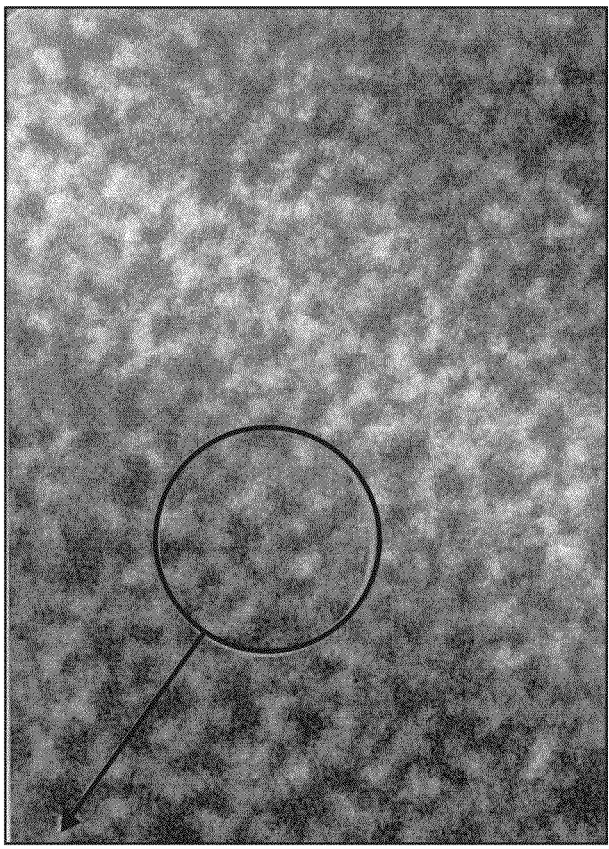
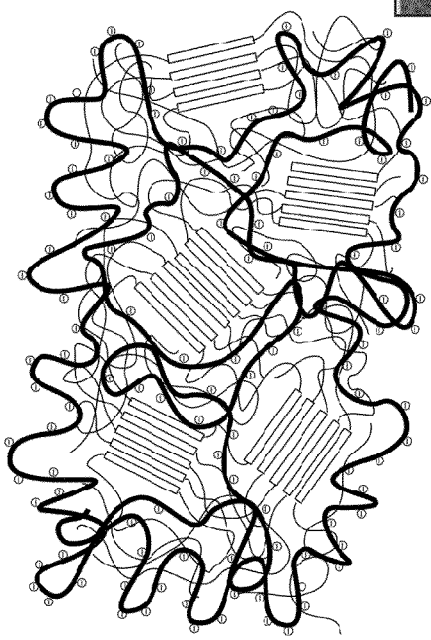

| Sample ID | Heating Rate (°C per min) | Tg (°C) | Tm (°C) | Crystallization (°C) |
|---|---|---|---|---|
| PEU (Control) | 10 | - | 176 186 | 92 |
| PEU/PAA (Sample) | 10 | -20 | 154 | 79 |
| PEU (Control) | 40 | -22 | 178 | 93 |
| PEU/PAA (Sample) | 40 | -21 | 164 | 90 |

FIG. 41

| Description | Solvent | % Change in mass due to swelling |
|---|---|---|
| Elasthane | $CH_2Cl_2$ | 150.6% |
| Elasthane | $CH_2=CHCOOH$ | 105.0% |
| Elasthane | $CH_3COOH$ | 86.6% |
| Elasthane | $CH_3COOCH_2CH_3$ | 41.3% |
| Elasthane | $O=C(CH_3)_2$ | 40.8% |
| Elasthane | $CH_3CH_2OH$ | 19.5% |
| Elasthane | $CH_3OH$ | 17.4% |
| Elasthane | $H_2O$ | 1.0% |
| Elasthane | $n-C_4H_9OH$ | < 1.0% |
|  |  |  |
| Elasthane + PAA | $H_2O$ | 130.0% |
| Elasthane + PAA | $CH_3OH$ | 69.7% |
| Elasthane + PAA | $CH_3COOH$ | 65.3% |
| Elasthane + PAA | $CH_3CH_2OH$ | 62.5% |
| Elasthane + PAA | $CH_2Cl_2$ | 60.4% |
| Elasthane + PAA | $OC(CH_3)_2$ | 49.0% |
| Elasthane + PAA | $CH_3COOCH_2CH_3$ | 20.2% |
| Elasthane + PAA | $n-C_4H_9OH$ | 3.4% |

FIG. 47

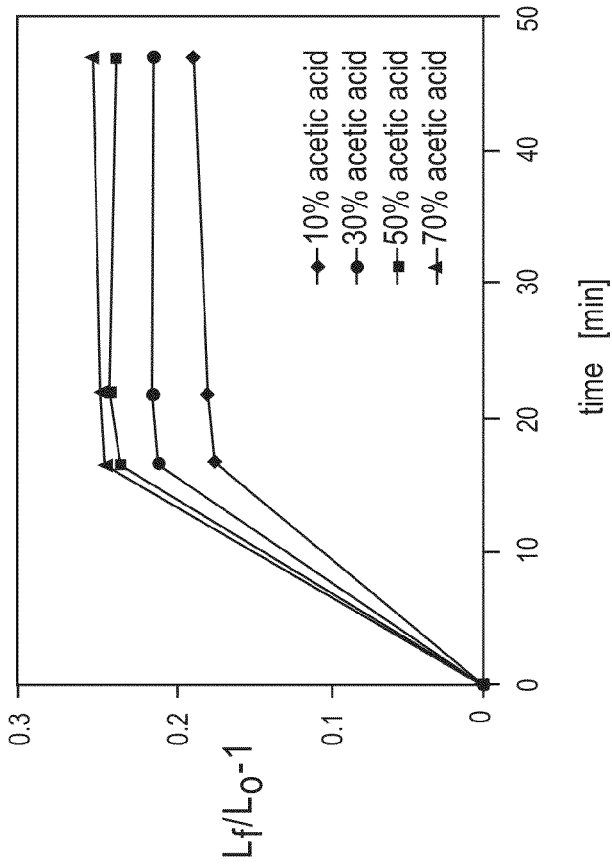
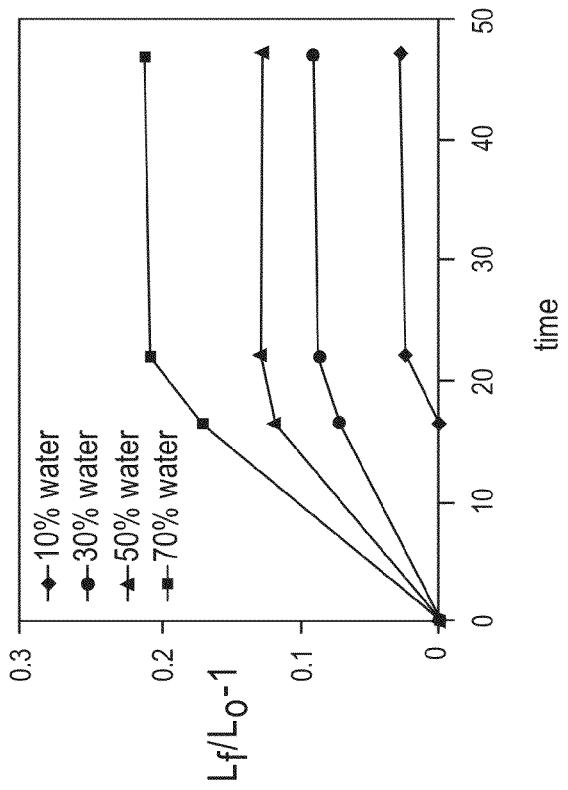
FIG. 48B
FIG. 48A

FIG. 54

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 55D | | 70% acrylic acid | | $H_2O$ | 0.1% MBAA | 0.1% HMPP (UV) |
| Elasthane™ 55D | | 70% acrylic acid | | $H_2O$ | 0.1% MBAA | 0.1% potassium persulfate (thermal) |
| Elasthane™ 55D | | 70% acrylic acid | | $H_2O$ | 0.1% MBAA | 0.1% AIBN (thermal) |
| Elasthane™ 55D | | 70% acrylic acid | | $H_2O$ | 0.01% MBAA | 0.1% HMPP (UV) |
| Elasthane™ 55D | | 70% acrylic acid | | $H_2O$ | none | 0.1% HMPP (UV) |
| Elasthane™ 55D | | 70% acrylic acid | | $H_2O$ | 0.1% TEGMDA | 0.1% HMPP (UV) |
| Elasthane™ 55D | | 100% acrylic acid | | none | 0.1% MBAA | 0.1% HMPP (UV) |
| Elasthane™ 55D | | 85% acrylic acid | | $H_2O$ | 0.1% MBAA | 0.1% HMPP (UV) |
| Elasthane™ 55D | | 60% acrylic acid | | $H_2O$ | 0.1% MBAA | 0.1% HMPP (UV) |
| Elasthane™ 55D | | 50% acrylic acid | | $H_2O$ | 0.1% MBAA | 0.1% HMPP (UV) |
| Elasthane™ 55D | | 40% acrylic acid | | $H_2O$ | 0.1% MBAA | 0.1% HMPP (UV) |
| Elasthane™ 55D | | 30% acrylic acid | | $H_2O$ | 0.1% MBAA | 0.1% HMPP (UV) |
| Elasthane™ 55D | | 15% acrylic acid | | $H_2O$ | 0.1% MBAA | 0.1% HMPP (UV) |
| Elasthane™ 55D | | 10% acrylic acid | | $H_2O$ | 0.1% MBAA | 0.1% HMPP (UV) |
| Elasthane™ 55D | | 70% acrylic acid | | acetic acid | 0.1% MBAA | 0.1% HMPP (UV) |
| Elasthane™ 55D | | 50% acrylic acid | | acetic acid | 0.1% MBAA | 0.1% HMPP (UV) |
| Elasthane™ 55D | | 30% acrylic acid | | acetic acid | 0.1% MBAA | 0.1% HMPP (UV) |
| Elasthane™ 55D | | 10% acrylic acid | | acetic acid | 0.1% MBAA | 0.1% HMPP (UV) |
| Elasthane™ 55D | | 35% acrylamido methyl propyl sulfonic acid | 35% acrylic acid | $H_2O$ | 0.1% MBAA | 0.1% HMPP (UV) |
| Elasthane™ 55D | | 35% vinyl sulfonic acid | 35% acrylic acid | $H_2O$ | 0.1% MBAA | 0.1% HMPP (UV) |
| Elasthane™ 55D | | 35% vinyl sulfonic acid | 35% acrylic acid | $H_2O$ | 0.1% MBAA | 0.1% ammonium persulfate (thermal) |
| Elasthane™ 55D | | 35% sulfopropyl methacrylate | 35% acrylic acid | $H_2O$ | 0.1% MBAA | 0.1% HMPP (UV) |
| Elasthane™ 55D | | 35% sulfopropyl methacrylate | | acetic acid | 0.1% MBAA | 0.1% HMPP (UV) |
| Elasthane™ 55D | | 35% acrylamido methyl propyl sulfonic acid | | acetic acid | 0.1% MBAA | 0.1% HMPP (UV) |
| Elasthane™ 55D | | 35% N-vinyl pyrrolidone | 35% acrylic acid | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 55D | | 35% 2-hydroxyethyl acrylate | 35% acrylic acid | $H_2O$ | 0.1% MBAA | 0.1% HMPP (UV) |
| Elasthane™ 55D | | 10% acrylamide | 50% acrylic acid | $H_2O$ | 0.1% MBAA | 0.1% HMPP (UV) |
| Elasthane™ 55D | | 70% acrylic acid | 0.5% methacryloxy-Vitamin C | $H_2O$ | 0.1% MBAA | 0.1% HMPP (UV) |
| Elasthane™ 55D | 1% Vitamin E | 70% acrylic acid | | $H_2O$ | 0.1% MBAA | 0.1% HMPP (UV) |
| Elasthane™ 55D | 0.25% Vitamin E | 70% acrylic acid | | $H_2O$ | 0.1% MBAA | 0.1% HMPP (UV) |
| Elasthane™ 55D | 1% methacryloxy-Vitamin E end groups | 70% acrylic acid | | $H_2O$ | 0.1% MBAA | 0.1% HMPP (UV) |
| Elasthane™ 55D | crosslinked via 1% dihydroxybutene chain extender | 70% acrylic acid | | $H_2O$ | 0.1% MBAA | 0.1% HMPP (UV) |
| Elasthane™ 55D | crosslinked via 5% dihydroxybutene chain extender | 70% acrylic acid | | $H_2O$ | 0.1% MBAA | 0.1% HMPP (UV) |
| Elasthane™ 55D | crosslinked via 1% glycerol methacrylate chain extender | 70% acrylic acid | | $H_2O$ | 0.1% MBAA | 0.1% HMPP (UV) |
| Elasthane™ 55D | crosslinked via 5% glycerol methacrylate chain extender | 70% acrylic acid | | $H_2O$ | 0.1% MBAA | 0.1% HMPP (UV) |
| Elasthane™ 55D | crosslinked via dimethacrylate end groups | 70% acrylic acid | | $H_2O$ | 0.1% MBAA | 0.1% HMPP (UV) |
| Elasthane™ 55D | crosslinked via diacrylamide end groups | 70% acrylic acid | | $H_2O$ | 0.1% MBAA | 0.1% HMPP (UV) |
| Elasthane™ 55D | blend of thermoplastic and diacrylamide-crosslinked polymer | 70% acrylic acid | | $H_2O$ | 0.1% MBAA | 0.1% HMPP (UV) |
| Elasthane™ 55D | partially crosslinked via methacrylate end groups | 70% acrylic acid | | $H_2O$ | 0.1% MBAA | 0.1% HMPP (UV) |
| Elasthane™ 55D | partially crosslinked via acrylamide end groups | 70% acrylic acid | | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyether urethanes | | | | | | |
| Elasthane™ 75D | | 70% acrylic acid | | $H_2O$ | 0.1% MBAA | 0.1% HMPP (UV) |
| Elasthane™ 80A | | 70% acrylic acid | | $H_2O$ | 0.1% MBAA | 0.1% HMPP (UV) |
| Elasthane™ 90A | | 70% acrylic acid | | $H_2O$ | 0.1% MBAA | 0.1% HMPP (UV) |
| Pellethane™ 55D | | 70% acrylic acid | | $H_2O$ | 0.1% MBAA | 0.1% HMPP (UV) |
| Pellethane™ 75D | | 70% acrylic acid | | $H_2O$ | 0.1% MBAA | 0.1% HMPP (UV) |
| | | | | | | |
| Polycarbonate urethanes | | | | | | |
| Bionate® 55D | | 70% acrylic acid | | $H_2O$ | 0.1% MBAA | 0.1% HMPP (UV) |
| Bionate® 55D | | 50% acrylic acid | | $H_2O$ | 0.1% MBAA | 0.1% HMPP (UV) |
| Bionate® 55D | crosslinked via dimethacrylate end groups | 70% acrylic acid | | $H_2O$ | 0.1% MBAA | 0.1% HMPP (UV) |
| Bionate® 55D | crosslinked via diacrylamide end groups | 70% acrylic acid | | $H_2O$ | 0.1% MBAA | 0.1% HMPP (UV) |
| Bionate® 55D | partially crosslinked via methacrylate end groups | 70% acrylic acid | | $H_2O$ | 0.1% MBAA | 0.1% HMPP (UV) |
| Bionate® 55D | partially crosslinked via acrylamide end groups | 70% acrylic acid | | $H_2O$ | 0.1% MBAA | 0.1% HMPP (UV) |
| Bionate® 90A | | 70% acrylic acid | | $H_2O$ | 0.1% MBAA | 0.1% HMPP (UV) |
| Bionate® 80A | | 70% acrylic acid | | $H_2O$ | 0.1% MBAA | 0.1% HMPP (UV) |
| Bionate® II 55D | | 70% acrylic acid | | $H_2O$ | 0.1% MBAA | 0.1% HMPP (UV) |
| Bionate® 75D | | 70% acrylic acid | | $H_2O$ | 0.1% MBAA | 0.1% HMPP (UV) |
| | | | | | | |
| Silicon-based polyurethanes | | | | | | |
| CarboSil® 55D | | 70% acrylic acid | | $H_2O$ | 0.1% MBAA | 0.1% HMPP (UV) |
| CarboSil® 80A | | 70% acrylic acid | | $H_2O$ | 0.1% MBAA | 0.1% HMPP (UV) |
| PurSil® 55D | | 70% acrylic acid | | $H_2O$ | 0.1% MBAA | 0.1% HMPP (UV) |
| PurSil® 80A | | 70% acrylic acid | | $H_2O$ | 0.1% MBAA | 0.1% HMPP (UV) |
| | | | | | | |
| Polyurethane urea | | | | | | |
| BioSpan® | | 70% acrylic acid | | $H_2O$ | 0.1% MBAA | 0.1% HMPP (UV) |

FIG. 54 (CONT.)

| HYDROPHOBIC POLYMER | MODIFICATIONS TO HYDROPHOBIC POLYMER | MONOMER | CO-MONOMER | SOLVENT | CROSSLINKER | INITIATOR (CURING METHOD) |
|---|---|---|---|---|---|---|
| Polyurethane urea | | | | | | |
| BioSpan® | | 20% acrylic acid | | $H_2O$ | 0.1% MBAA | 0.1% HMPP (UV) |
| BioSpan® | crosslinked via dimethacrylate end groups | 70% acrylic acid | | $H_2O$ | 0.1% MBAA | 0.1% HMPP (UV) |
| BioSpan® | crosslinked diacrylamide end groups | 70% acrylic acid | | $H_2O$ | 0.1% MBAA | 0.1% HMPP (UV) |
| BioSpan® | partially crosslinked via methacrylate end groups | 70% acrylic acid | | $H_2O$ | 0.1% MBAA | 0.1% HMPP (UV) |
| BioSpan® | partially crosslinked via acrylamide end groups | 70% acrylic acid | | $H_2O$ | 0.1% MBAA | 0.1% HMPP (UV) |
| | | | | | | |
| Other polymers | | | | | | |
| Acrylonitrile Butadiene Styrene | | 100% acrylic acid | | none | 0.1% MBAA | 0.1% HMPP (UV) |
| Acrylonitrile Butadiene Styrene | | 100% acrylic acid | | none | 0.1% MBAA | 0.1% HMPP (UV) |
| Acrylonitrile Butadiene Styrene | | 100% acrylic acid | | none | 0.1% MBAA | 0.1% HMPP (UV) |
| Poly(methyl methacrylate) | | 100% acrylic acid | | none | 0.1% MBAA | 0.1% HMPP (UV) |
| Polyaryletheretherketone (PEEK) | | 50% acrylic acid | | DMAC | 0.1% MBAA | 0.1% HMPP (UV) |
| Polydimethyl siloxane (PDMS) | | 50% acrylic acid | | THF | 0.1% MBAA | 0.1% HMPP (UV) |

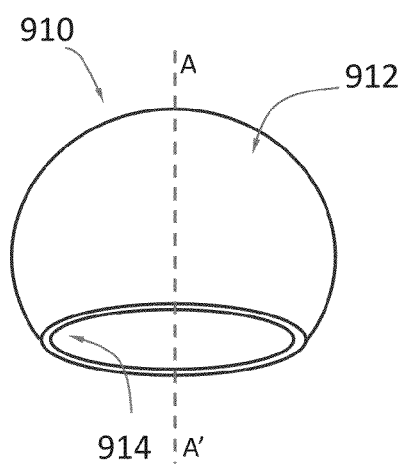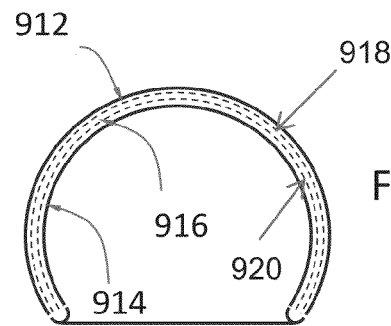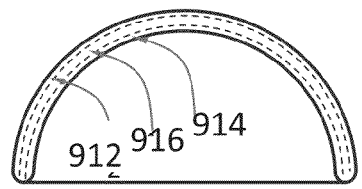
Fig. 59A
Fig. 59B
Fig. 59C

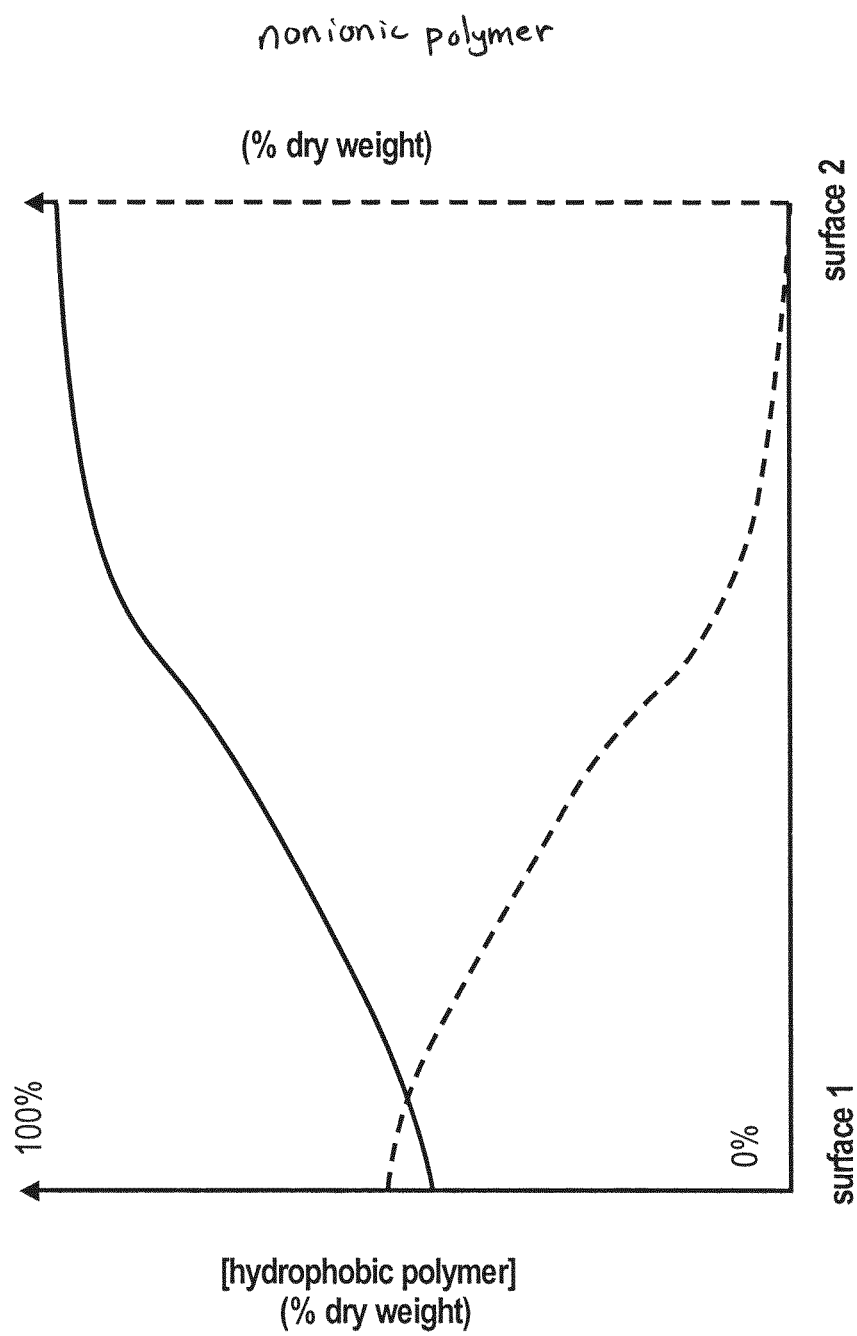

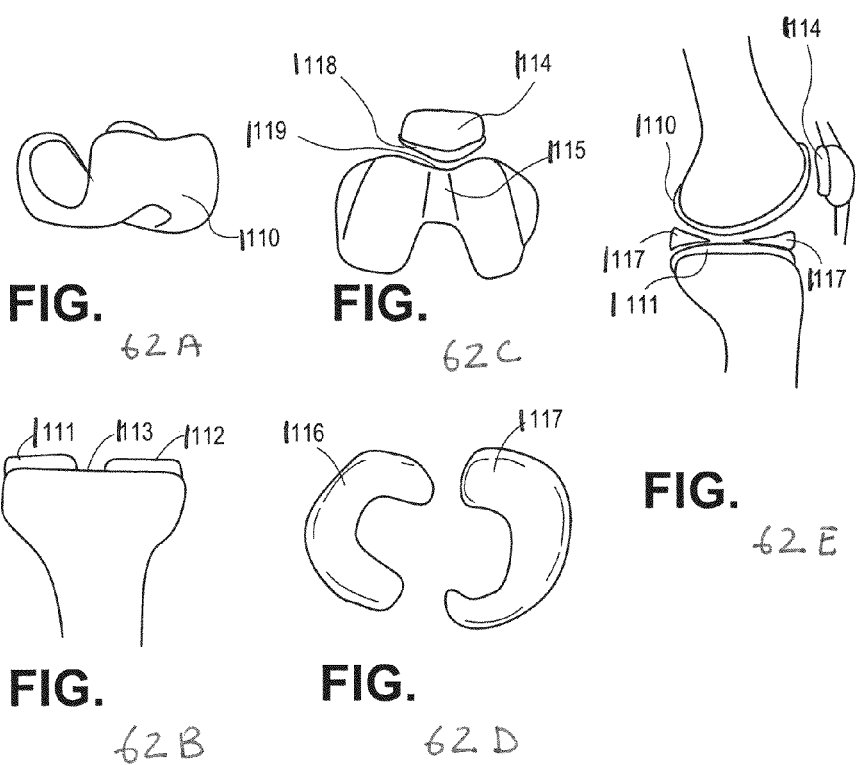

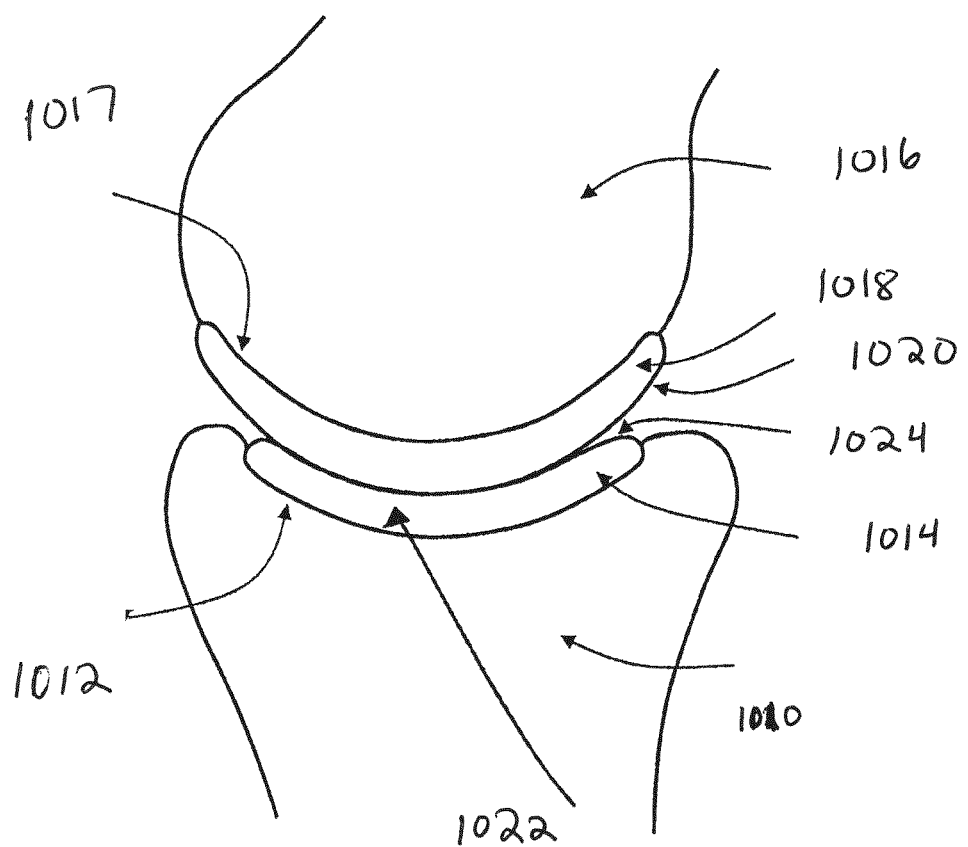

HYDROPHOBIC AND HYDROPHILIC INTERPENETRATING POLYMER NETWORKS DERIVED FROM HYDROPHOBIC POLYMERS AND METHODS OF PREPARING THE SAME

CROSS REFERENCE TO RELATED APPLICATIONS

This application is a continuation-in-part of U.S. application Ser. No. 12/499,041 filed Jul. 7, 2009, now abandoned which application claims the benefit of U.S. Provisional Application No. 61/078,741, filed Jul. 7, 2008; No. 61/079,060, filed Jul. 8, 2008; No. 61/095,273, filed Sep. 8, 2008; and No. 61/166,194, filed Apr. 2, 2009.

This application claims the benefit of U.S. Provisional Application No. 61/377,844 filed Aug. 27, 2010; and U.S. Provisional Application No. 61/383,705 filed Sep. 16, 2010. The disclosures of each of these prior applications is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention pertains to semi- and fully interpenetrating polymer networks, methods of making semi- and fully interpenetrating polymer networks, articles made from such semi- and fully interpenetrating polymer networks, and methods of using such articles.

BACKGROUND

Fully interpenetrating polymer networks (IPN's) and semi-interpenetrating polymer networks ("semi-IPN's") have been created from a variety of starting materials and have been used for a variety of applications. IPN's and semi-IPN's can combine the beneficial properties of the polymers from which they are made and can avoid some of the undesirable properties of their component polymers.

Prior IPN's and semi-IPN's have been proposed for use in biomedical applications, such as a coating for an implant or as artificial cartilage. See, e.g., U.S. Patent Publ. No. 2005/0147685; U.S. Patent Publ. No. 2009/0035344; and U.S. Patent Publ. No. 2009/008846. The utility of prior IPN's and semi-IPN's for their proposed applications is limited by the properties of those compositions, however. In addition, the starting materials and processes of making such prior compositions limit not only the resulting properties of the IPN or semi-IPN but also the commercial viability of the manufacturing processes and the articles made in such processes. Also, the mechanical properties of prior IPNs and semi-IPNs are often limited by the mechanical properties of the component polymers used, which in the case of most intrinsically hydrophilic, water-swellable polymers, are usually quite low. For example, the prior art has not described a viable process for making a water-swellable IPN or semi-IPN from commercially available hydrophobic thermoset or thermoplastic polymers, such as polyurethane or ABS.

Finally, the utility of prior IPN and semi-IPN compositions and the value of the articles formed from such compositions have been limited by the inability to create IPN's and semi-IPN's with desired characteristics, such as strength, lubricity and wear-resistance.

SUMMARY OF THE DISCLOSURE

The mechanical properties desired for certain medical applications is often outside the range of possibility of many hydrophilic starting materials. Hence, one aspect of this invention takes advantage of the high mechanical strength of hydrophobic starting materials and combines those materials with certain ionic polymers as a useful way to achieve the goal of high mechanical strength in addition to other desirable properties. Thus, while the prior art took water-swellable polymers and tried to make them stronger, one aspect of this invention takes strong materials and makes them more water-swellable. A second aspect of this invention is to take materials and make them more adhesive to materials to which they are otherwise not adhesive. Examples of two such materials are polyurethanes and PMMA bone cement. PMMA bone cement is known as a "grouting" compound that acts as an anchoring material for orthopaedic implants to bone by way of mutual mechanical interlocking. One aspect of the invention describes a way of introducing a constituent of bone cement into polyurethane in order to facilitate a direct bond with bone cement rather than just mechanical interlocking. In some embodiments, this bonding eliminates the need for a mechanical interface between a relatively compliant device and bone cement, and causes them to bear loads and transfer loads as a single body rather than as two bodies.

For purposes of this application, an "interpenetrating polymer network" or "IPN" is a material comprising two or more polymer networks which are at least partially interlaced on a molecular scale, but not covalently bonded to each other, and cannot be separated unless chemical bonds are broken. A "semi-interpenetrating polymer network" or "semi-IPN" is a material comprising one or more polymer networks and one or more linear or branched polymers characterized by the penetration on a molecular scale of at least one of the networks by at least some of the linear or branched macromolecules. As distinguished from an IPN, a semi-IPN is a polymer blend in which at least one of the component polymer networks is not chemically crosslinked by covalent bonds.

A "polymer" is a substance comprising macromolecules, including homopolymers (a polymer derived from one species of monomer) and copolymers (a polymer derived from more than one species of monomer). A "hydrophobic polymer" is a pre-formed polymer network having at least one of the following two properties: (1) a surface water contact angle of at least 45° and (2) exhibits water absorption of 2.5% or less after 24 hours at room temperature according to ASTM test standard D570. A "hydrophilic polymer" is a polymer network having a surface water contact angle less than 45° and exhibits water absorption of more than 2.5% after 24 hours at room temperature according to ASTM test standard D570. An "ionic polymer" is defined as a polymer comprised of macromolecules containing at least 2% by weight ionic or ionizable monomers (or both), irrespective of their nature and location. An "ionizable monomer" is a small molecule that can be chemically bonded to other monomers to form a polymer and which also has the ability to become negatively charged due the presence of acid functional groups such carboxylic acid and/or sulfonic acid. A "thermoset polymer" is one that doesn't melt when heated, unlike a thermoplastic polymer. Thermoset polymers "set" into a given shape when first made and afterwards do not flow or melt, but rather decompose upon heating and are often highly crosslinked and/or covalently crosslinked. A "thermoplastic polymer" is one which melts or flows when heated, unlike thermoset polymers. Thermoplastic polymers are usually not covalently crosslinked. "Phase separation" is defined as the conversion of a single-phase system into a multi-phase system; especially the separation of two immiscible blocks of a block co-polymer into two phases, with the possibility of a small interphase in which a small degree of mixing occurs.

The present invention includes a process for modifying common commercially available hydrophobic thermoset or thermoplastic polymers, such as polyurethane or ABS to provide new properties, such as strength, lubricity, electrical conductivity and wear-resistance. Other possible hydrophobic thermoset or thermoplastic polymers are described below. The invention also includes the IPN and semi-IPN compositions as well as articles made from such compositions and methods of using such articles. The IPN and semi-IPN compositions of this invention may attain one or more of the following characteristics: High tensile and compressive strength; low coefficient of friction; high water content and swellability; high permeability; biocompatibility; and biostability.

Applications of the invention are the creation of hydrophilic, lubricious sidings or coatings to reduce the static and dynamic coefficient of friction between two bearing surfaces and to reduce drag and/or biofilm formation and/or barnacle formation in marine vessels, diving or swimming suits, other water crafts or water-borne objects, or pipes. Furthermore, the invention has potential in electrochemical applications that require conduction of electrical current, or permeability of ions such as proton exchange membranes, fuel cells, filtration devices, and ion-exchange membranes. In addition, the invention can be used as a method for making bearings and moving parts for applications such as engines, pistons, or other machines or machine parts. The invention can also be used in numerous biomedical applications including cartilage substitutes, orthopaedic joint replacement and resurfacing devices or components thereof, intervertebral discs, stents, vascular or urinary catheters, condoms, heart valves, vascular grafts, and both short-term and long-term implants in other areas of the body, such as skin, brain, spine, the gastrointestinal system, the larynx, and soft tissues in general. In addition, it can be used as a component of various surgical tools and instruments. In all of these applications drugs can be incorporated into the material for localized drug delivery. These interpenetrating polymer networks can also be used to fabricate specific drug delivery vehicles in which a therapeutic agent is released from the polymer matrix. One aspect of the invention provides compositions of a water-swellable IPN or semi-IPN of a hydrophobic thermoset or thermoplastic polymer and an ionic polymer. In some embodiments, the IPN or semi-IPN exhibits a lower coefficient of friction than the hydrophobic thermoset or thermoplastic polymer. In some embodiments, the IPN or semi-IPN is more water-swellable, exhibits higher resistance to creep, and/or exhibits a higher conductivity and permeability than the hydrophobic thermoset or thermoplastic polymer. Some embodiments of the composition also include an anti-oxidation agent.

In some embodiments, the IPN or semi-IPN is formed by diffusing an ionizable monomer precursor solution into the hydrophobic thermoset or thermoplastic polymer and polymerizing the monomers to form the ionic polymer.

In some embodiments, the composition also includes water, which may form a hydration gradient from a first portion of the composition to a second portion of the composition. An electrolyte may be dissolved in the water. The IPN or semi-IPN may also be negatively charged. In various embodiments, the hydrophobic thermoset or thermoplastic polymer may be physically entangled or chemically crosslinked with the ionic polymer.

In some embodiments, the hydrophobic thermoset or thermoplastic polymer has ordered and disordered domains, and the ionic polymer may be disposed in the disordered domains.

In various embodiments the hydrophobic thermoset or thermoplastic polymer may be selected from the group consisting of polyurethane, polymethyl methacrylate, polydimethylsiloxane, and acrylonitrile butadiene styrene. The ionic polymer may be, e.g., a poly(acrylic acid) or poly(sulfopropyl methacrylate), combinations, or derivatives thereof. The ionic polymer may include carboxylate groups and/or sulfonate groups.

In some embodiments, the ionic polymer forms a concentration gradient from a first portion of the composition to a second portion of the composition. The concentration gradient may, e.g., provide a stiffness and/or hydration gradient within the composition.

Some embodiments include a second hydrophobic thermoset or thermoplastic polymer which may be disposed in a layer separate from the first hydrophobic thermoset or thermoplastic polymer or may be diffused throughout the first hydrophobic thermoset or thermoplastic polymer.

Another aspect of the invention provides a process for producing a water-swellable IPN or semi-IPN from an hydrophobic thermoset or thermoplastic polymer including the following steps: placing an ionizable monomer solution in contact with a solid form of the hydrophobic thermoset or thermoplastic polymer; diffusing the ionizable monomer solution into the thermoset or thermoplastic polymer; and polymerizing the ionizable monomers to form a ionic polymer inside the thermoset or thermoplastic polymer, thereby forming the IPN or semi-IPN.

Some embodiments include the step of adding an anti-oxidation agent. Some embodiments include the step of swelling the IPN or semi-IPN with water, e.g., to form a hydration gradient from a first portion of the composition to a second portion of the composition. The method may also include the step of swelling the IPN or semi-IPN with an electrolyte solution. Various embodiments include the steps of chemically crosslinking or physically entangling the hydrophobic thermoset or thermoplastic polymer with the ionic polymer.

In embodiments in which the hydrophobic thermoset or thermoplastic polymer has ordered and disordered domains, the method may include the step of swelling the disordered domains with the ionizable monomer solution prior to the polymerizing step.

In some embodiments, the hydrophobic thermoset or thermoplastic polymer is selected from the group consisting of polyurethane, polymethyl methacrylate, polydimethylsiloxane, and acrylonitrile butadiene styrene. The ionizable monomer solution may be an acrylic acid solution and may comprise monomers with carboxylate groups and/or sulfonate groups.

In some embodiments, the method includes the step of forming a concentration gradient of the ionic polymer within the IPN or semi-IPN through regioselective diffusion of the ionizable monomer solution through the hydrophobic thermoset of thermoplastic polymer to, e.g., provide a stiffness and/or hydration gradient within the composition.

Some embodiments of the method may include, prior to the polymerizing step, the steps of placing the ionizable monomer solution in contact with a solid form of a second hydrophobic thermoset or thermoplastic polymer; and diffusing the ionizable monomer solution into the second hydrophobic thermoset or thermoplastic polymer. In such embodiments, the second hydrophobic thermoset or thermoplastic polymer may be in a separate layer adjacent to the first hydrophobic thermoset or thermoplastic polymer or may be diffused within the first hydrophobic thermoset or thermoplastic polymer.

Some embodiments include the step of changing the IPN or semi-IPN from a first shape to a second shape, such as by heating the IPN or semi-IPN.

Yet another aspect of the invention provides a medical implant including a water-swellable IPN or semi-IPN including an hydrophobic thermoset or thermoplastic polymer and an ionic polymer, the implant having a bone contact surface shaped to conform to a bone surface. Some embodiments also include a fluid capsule disposed in an interior region of the implant. Some embodiments have an insertion portion adapted to be inserted into a bone and a joint interface portion adapted to be disposed within a joint space, such as bone screws, sutures, or staples engaged with the IPN or semi-IPN and adapted to engage the bone to attach the IPN or semi-IPN to the bone and/or a stem extending from the bone contact surface and adapted to be inserted into the bone. The medical implant may also be incorporated as a bearing component of another device, such as a metal-based prosthesis.

The medical implant may also include a bonding agent adapted to attach the medical implant to a bone, such as a bone ingrowth surface formed on the bone contact surface. In some embodiments, the ionic polymer forms a concentration gradient from a first portion of the implant to a second portion of the implant. Some embodiments have a second hydrophobic thermoset or thermoplastic polymer adjacent to the first hydrophobic thermoset or thermoplastic polymer, the ionic polymer interpenetrating at least the first hydrophobic thermoset or thermoplastic polymer.

In some embodiments, the water-swellable IPN or semi-IPN has properties mimicking stiffness and lubricity properties of natural cartilage and may be adapted and configured to replace cartilage in a joint. The IPN or semi-IPN may have a shape selected from the group consisting of a cap, a cup, a plug, a mushroom, a stem, and a patch, and it may be adapted to fit a condyle, tibial plateau, meniscus, labrum, or glenoid.

Still another aspect of the invention provides a method of repairing an orthopedic joint including the steps of replacing natural cartilage with a water-swellable IPN or semi-IPN having a hydrophobic thermoset or thermoplastic polymer and an ionic polymer and engaging the IPN or semi-IPN with a bone surface defining the joint. The method may also include the steps of bonding, suturing, stapling, and/or screwing the IPN or semi-IPN to the bone surface. The method may also include incorporating the material as a bearing component of another device, such as a metal-based prosthesis. The method may also include the step of inserting a stem portion into the bone surface. The orthopedic joint may be selected from a group consisting of a shoulder joint, a finger joint, a hand joint, an ankle joint, a foot joint, a toe joint, a knee medial compartment joint, a patellofemoral joint, a total knee joint, a knee meniscus, a femoral joint, an acetabular joint, a labral joint, an elbow, an intervertebral facet, and a vertebral joint.

Yet another aspect of the invention provides a marine hull coating including a water-swellable IPN or semi-IPN including a hydrophobic thermoset or thermoplastic polymer and an ionic polymer, the coating having a hull contact surface adapted to attach to a marine hull. The coating may also include an ultraviolet light protection agent and/or an anti-oxidation agent.

Some embodiments of the invention include compositions of matter having an IPN or semi-IPN that includes a hydrophobic thermoset or thermoplastic polymer and a non-ionic polymer where the IPN or semi-IPN is capable of adhering to a material comprising the same non-ionic polymer. Optionally, in any of the preceding embodiments, the non-ionic polymer can be derived from an ethylenically unsaturated monomer such as an acrylic monomer or methacrylic monomer. Optionally, in any of the preceding embodiments, the ethylenically unsaturated monomer does not have an ionizable functional group. Optionally, in any of the preceding embodiments, the non-ionic polymer may be a constituent, component, or ingredient of an interlocking, filler, grouting material or anchoring compound for orthopaedic implants such as bone cement.

Optionally, in any of the preceding embodiments, in further variations, the non-ionic polymer is selected from the group consisting of polymethyl methacrylate and polystyrene. In some embodiments, the hydrophobic thermoset or thermoplastic polymer is a polyurethane polymer.

Optionally, in any of the preceding embodiments, the IPN or semi-IPN exhibits greater adhesiveness, stiffness, shear strength than the hydrophobic thermoset or thermoplastic polymer.

Optionally, in any of the preceding embodiments, the composition can further comprise an anti-oxidation agent.

Optionally, in any of the preceding embodiments, the IPN or semi-IPN is formed by diffusing a non-ionizable monomer precursor into the hydrophobic thermoset or thermoplastic polymer and polymerizing the monomer to form the non-ionic polymer within the hydrophobic thermoset or thermoplastic polymer. Optionally, in any of the preceding embodiments, in some variations, the hydrophobic thermoset or thermoplastic polymer is physically entangled with the non-ionic polymer. In other embodiments, the hydrophobic thermoset or thermoplastic polymer is chemically crosslinked to the non-ionic polymer.

Optionally, in any of the preceding embodiments, the non-ionic polymer forms a concentration gradient from a first portion of the composition to a second portion of the composition. The concentration gradient can provide a modulus, strength, or adhesiveness gradient within the composition.

Another embodiment provides for a composition of matter comprising an IPN or semi-IPN and a bone cement, the IPN or semi-IPN comprising a hydrophobic thermoset or thermoplastic polymer and a non-ionic polymer, and the bone cement comprising the same non-ionic polymer. Optionally, in any of the preceding embodiments, in some embodiments, the IPN exhibits greater adhesiveness with the bone cement than the hydrophobic thermoset or thermoplastic polymer with the bone cement. Optionally, in any of the preceding embodiments, in further embodiments, the non-ionic polymer forms a concentration gradient from a first portion of the composition to a second portion of the composition. In other variations, the concentration gradient provides an adhesiveness gradient within the composition.

Another aspect of the invention provides a process for preparing an IPN or semi-IPN from a hydrophobic thermoset or thermoplastic polymer including the following steps: placing a non-ionizable monomer or a solution of non-ionizable monomer in contact with a solid form of the hydrophobic thermoset or thermoplastic polymer; diffusing the non-ionizable monomer solution into the thermoset or thermoplastic polymer; and polymerizing the non-ionizable monomers to form a non-ionic polymer inside the thermoset or thermoplastic polymer, thereby forming the IPN or semi-IPN. Optionally, in any of the preceding embodiments, the process can also include forming the solid form as a medical implant having a bone interfacing surface and a joint interfacing surface.

In further embodiments, the invention provides for a medical implant comprising a bone interfacing surface, a joint interfacing surface, and an IPN or semi-IPN comprising a hydrophobic thermoset or thermoplastic polymer and a non-ionic polymer, wherein the IPN or semi-IPN is capable of adhering to a material comprising the same non-ionic polymer. Optionally, in any of the preceding embodiments, the IPN is disposed on at least one portion of the bone interfacing surface. Optionally, in any of the preceding embodiments, the non-ionic polymer forms a concentration gradient from a first portion of the medical implant to a second portion of the medical implant. Various embodiments include a medical implant where the concentration gradient provides an adhesiveness, modulus, stiffness, or strength gradient within the medical implant. In other embodiments, the bone interfacing surface and the joint interfacing surface of the implant are configured for a hip joint.

Optionally, in any of the preceding embodiments, the non-ionic polymer in the implant is derived from an ethylenically unsaturated monomer without an ionizable functional group. For example, in some embodiments, the non-ionic polymer is polymethylmethacrylate.

Another aspect of the invention provides for a medical implant comprising a bone interfacing surface, a joint interfacing surface, and an IPN or semi-IPN comprising a hydrophobic thermoset or thermoplastic polymer and an non-ionic polymer, wherein the IPN or semi-IPN is disposed on at least one section of the medical implant and the said section exhibits greater adhesion with a bone cement than the hydrophobic thermoset or thermoplastic polymer.

Various other embodiments include a composition of matter comprising a first IPN or semi-IPN comprising a non-ionic polymer P and a hydrophobic thermoset or thermoplastic polymer T and a second IPN or semi-IPN comprising the same said hydrophobic thermoset or thermoplastic polymer T and a hydrophilic interpenetrating polymer S. Optionally, in any of the preceding embodiments, P can be derived from a non-ionizable, ethylenically unsaturated monomer. Optionally, in any of the preceding embodiments, the ethylenically unsaturated monomer does not have an ionizable functional group. Optionally, in any of the preceding embodiments, T is a polyurethane containing polymer. Optionally, in any of the preceding embodiments, S is an ionic polymer. Optionally, in any of the preceding embodiments, P is polymethylmethacrylate and T is polyurethane.

Optionally, in any of the preceding embodiments, the non-ionic polymer P forms a concentration gradient from a first portion of the composition to a second portion of the composition. Optionally, in any of the preceding embodiments, the non-ionic polymer P forms a concentration gradient from a first portion of the first IPN or semi-IPN to a second portion of the first IPN or semi-IPN. Optionally, in any of the preceding embodiments, the hydrophilic interpenetrating polymer S forms a concentration gradient from a first portion of the composition to a second portion of the composition.

Optionally, in any of the preceding embodiments, the hydrophilic interpenetrating polymer S forms a concentration gradient from a first portion of the second IPN or semi-IPN to a second portion of the second IPN or semi-IPN. Optionally, in any of the preceding embodiments, the composition include at least two concentration gradients, wherein the non-ionic polymer P forms a first concentration gradient from a first portion of the composition to a second portion of composition and the hydrophilic interpenetrating polymer S forms a second concentration gradient from a third portion of the composition to a fourth portion of the composition.

Optionally, in any of the preceding embodiments, the first concentration gradient provides an adhesiveness, lubricious, shear strength, or stiffness gradient within the composition. Optionally, in any of the preceding embodiments, the first concentration gradient provides an adhesiveness gradient and the second concentration gradient provides a lubricious gradient. Optionally, in any of the preceding embodiments, the first concentration gradient and the second concentration gradient partially or fully overlap.

Optionally, in any of the preceding embodiments, the composition further comprises a region of the hydrophobic thermoset or thermoplastic polymer T that is disposed adjacent to an IPN or semi-IPN, wherein the region of the hydrophobic thermoset or thermoplastic polymer T does not contain a polymer P or S.

Yet another aspect of this invention provides for a composition of matter comprising a first IPN or semi-IPN comprising a hydrophobic thermoset or thermoplastic polymer and a non-ionic polymer and a second IPN or semi-IPN comprising the same said hydrophobic thermoset or thermoplastic polymer and a hydrophilic interpenetrating polymer. Optionally, in any of the preceding embodiments, the first IPN or semi-IPN is disposed in a first section of the said hydrophobic thermoset or thermoplastic polymer and the second IPN or semi-IPN is disposed in a second section of the said hydrophobic thermoset or thermoplastic polymer.

Another aspect of this invention provides for a composition of matter comprising at least two IPNs or semi-IPNs, wherein a first IPN or semi-IPN comprises a hydrophobic thermoset or thermoplastic polymer and a non-ionic polymer and a second IPN or semi-IPN comprises a hydrophobic thermoset or thermoplastic polymer and a hydrophilic interpenetrating polymer.

A further embodiment provides for a process for preparing a composition of matter comprising at least two IPNs or semi-IPNs from a hydrophobic thermoset or thermoplastic polymer including steps: placing a first section of a solid form of the hydrophobic thermoset or thermoplastic polymer in contact with a first non-ionizable or ionizable monomer solution; diffusing the first non-ionizable or ionizable monomer solution into the thermoset or thermoplastic polymer; placing a second section of the solid form in contact with a second non-ionizable or ionizable monomer solution; diffusing the second non-ionizable or ionizable monomer solution into the thermoset or thermoplastic polymer; and polymerizing the non-ionizable or ionizable monomers to form at least two IPNs or semi-IPNs inside the solid form.

Another aspect of the invention provides for a process for preparing a composition of matter comprising at least two IPNs or semi-IPNs from a hydrophobic thermoset or thermoplastic polymer including steps: placing a first section of a solid form of a hydrophobic thermoset or thermoplastic polymer in contact with a first non-ionizable or ionizable monomer solution; diffusing the first non-ionizable or ionizable monomer solution into the thermoset or thermoplastic polymer; polymerizing the first non-ionizable or ionizable monomers to form a first IPN or semi-IPN inside the solid form; placing a second section of the solid form in contact with a second non-ionizable or ionizable monomer solution; diffusing the second non-ionizable or ionizable monomer solution into the thermoset or thermoplastic polymer; and polymerizing the second non-ionizable or ionizable monomers to form a second IPN or semi-IPN inside the solid form.

Various embodiments also include a medical implant comprising a bone interfacing surface, a joint interfacing surface, a first IPN or semi-IPN comprising a non-ionic polymer P and a hydrophobic thermoset or thermoplastic polymer T, and a second IPN or semi-IPN comprising the same said hydrophobic thermoset or thermoplastic polymer T and a hydrophilic interpenetrating polymer S. Optionally, in any of the preceding embodiments, the implant can further include at least two concentration gradients, wherein the non-ionic polymer P forms a first concentration gradient from a first portion of the implant to a second portion of the implant and the hydrophilic interpenetrating polymer S forms a second concentration gradient from a third portion of the implant to a fourth portion of the implant. Optionally, in any of the preceding embodiments, the first concentration gradient in the implant provides an adhesiveness gradient and the second concentration gradient provides a lubricious gradient. In other embodiments, the non-ionic polymer P in the implant is derived from an ethylenically unsaturated monomer without ionizable functional groups.

Optionally, in any of the preceding embodiments, in additional embodiments the non-ionic polymer P in the implant is a constituent of a bone cement. Optionally, in any of the preceding embodiments, the non-ionic polymer P in the implant is selected from the group consisting of polymethylmethacrylate and polystyrene. Optionally, in any of the preceding embodiments, the hydrophobic thermoset or thermoplastic polymer T is a polyurethane polymer. Optionally, in any of the preceding embodiments, the first IPN or semi-IPN exhibits greater adhesiveness, stiffness, or shear strength than the hydrophobic thermoset or thermoplastic polymer T. In further embodiments, the first IPN or semi-IPN exhibits greater adhesiveness than the hydrophobic thermoset or thermoplastic polymer T and the second IPN or semi-IPN exhibits greater lubriciousness than the hydrophobic thermoset or thermoplastic polymer T. Optionally, in any of the preceding embodiments, the medical implant includes first and second gradients that partially or fully overlap. Optionally, in any of the preceding embodiments, the medical implant includes a region on the implant wherein the region is adjacent to the first and second IPN or semi-IPN and does not contain an IPN or semi-IPN.

Another aspect of this invention includes a medical implant comprising a bone interfacing surface, a joint interfacing surface, and at least two IPNs or semi-IPNs, wherein a first IPN or semi-IPN comprises a non-ionic polymer disposed in at least one section of a hydrophobic thermoset or thermoplastic polymer, and a second IPN or semi-IPN comprises a non-ionic polymer disposed in at least one section of the said hydrophobic thermoset or thermoplastic polymer.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4B illustrates variation of gradient properties within an IPN according to the invention.

FIG. 4C illustrates the variation of an ionic polymer across a gradient IPN.

FIGS. 6A-B illustrate illustrates shaping of a gradient IPN article.

FIGS. 7A-D illustrate shape heating of an IPN.

FIGS. 8A-D illustrate bonding of a gradient IPN article to a surface.

FIGS. 10A-B illustrate an osteochondral graft having an opening to accommodate a ligament.

FIGS. 11A-E show osteochondral grafts formed from an IPN or semi-IPN of this invention that may be used singly or in any combination needed to replace or augment cartilage within a knee joint.

FIG. 14 shows the use of an IPN or semi-IPN of this invention as a bursa osteochondral graft, labrum osteochondral graft, glenoid osteochondral graft and humeral head osteochondral graft.

FIG. 15 shows the use of an IPN or semi-IPN of this invention as prostheses for resurfacing intervertebral facets.

FIG. 16A shows a prosthetic cartilage plug formed from a gradient IPN composition of this invention.

FIGS. 16B-D show embodiments in which porous surfaces are formed on the cartilage plug. FIG. 16D is a bottom elevational view of the embodiment of FIG. 16C.

FIG. 32 shows the use of a lubricious IPN or semi-IPN composition of this invention to resurface the hull of a marine vessel.

FIG. 33 shows the use of a lubricious thermoplastic or thermoset IPN to modify interfacing surfaces of machine parts that move with respect to each other.

FIG. 34 shows the use of a lubricious thermoplastic or thermoset IPN to reduce fluid drag on the inner surface of a pipe.

FIG. 38 shows the PEU/PAA semi-IPN material subject to Transmission Electron Microscopy analysis with a schematic diagram associated with Example 34.

FIG. 41 shows the results of thermal analysis of the PEU/PAA semi-IPN material analyzed by DSC associated with Example 36.

FIG. 47 shows the swelling behavior of polyether urethane and PEU/PAA semi-IPN in various aqueous and organic solvents associated with Example 40.

FIGS. 48A-B show the results of the swelling of polyether urethane and PEU/PAA semi-IPN in water and acetic acid associated with Example 41.

FIG. 54 shows a partial list of materials that have been made in accordance with the present invention.

FIG. 59A shows an orthopedic implant having a hydrophobic adhesive IPN or semi-IPN and a hydrophilic interpenetrating IPN or semi-IPN according to this invention.

FIGS. 59B-C show cross-sectional views along line A-A' of the orthopedic implant of FIG. 59A.

FIG. 60 illustrates the variation of a non-ionic polymer across a gradient IPN.

FIGS. 62A-E show osteochondral grafts that can be formed with a double concentration gradient.

FIG. 63 shows two sides of a generic articular joint with both sides of the joint replaced with components or devices according to embodiments of this invention.

DETAILED DESCRIPTION

Figure 1A:
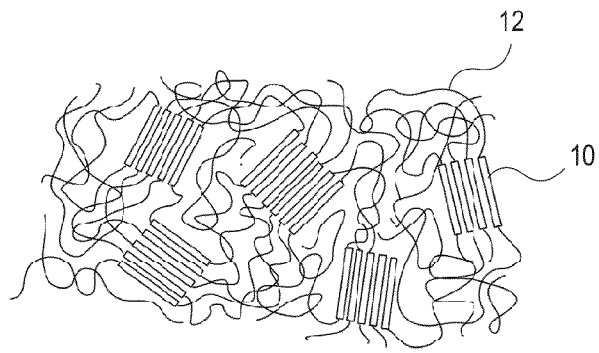
FIGS. 1A-D illustrate a method of forming an IPN or semi-IPN according to one aspect of this invention.

The present invention includes a process for modifying common commercially available hydrophobic thermoset or thermoplastic polymers to confer upon them qualities such as lubricity, permeability, conductivity and wear-resistance. Such hydrophobic polymers ordinarily do not soak up water and are generally useful for their mechanical strength, impermeability and insulating ability. An exemplary list of hydrophobic polymers modifiable by the process of this invention includes the following: Acrylonitrile butadiene styrene (ABS), Polymethylmethacrylate (PMMA), Acrylic, Celluloid, Cellulose acetate, Ethylene-Vinyl Acetate (EVA), Ethylene vinyl alcohol (EVAL), Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polyhydroxyalkanoates (PHAs), Polyketone (PK), Polyester, Polyetheretherketone (PEEK), Polyetherimide (PEI), Polyethersulfone (PES)—see Polysulfone, Polyethylenechlorinates (PEC), Polyimide (PI), Polymethylpentene (PMP), Polyphenylene oxide (PPO), Polyphenylene sulfide (PPS), Polyphthalamide (PPA), Polystyrene (PS), Polysulfone (PSU), Polyvinyl acetate (PVA), Polyvinyl chloride (PVC), Polyvinylidene chloride (PVDC), Spectralon, Styrene-acrylonitrile (SAN), Polydimethylsiloxane (PDMS), and Polyurethanes (PU). A wide variety of polyurethanes can be used with varying hard segment, soft segment, and chain extender compositions, as will be described herein.

One aspect of the invention takes advantage of a characteristic of some modifiable thermoset or thermoplastic hydrophobic polymers: The presence of ordered and disordered (amorphous) domains within the polymer. For example, some hydrophobic thermoset or thermoplastic polymers such as polyurethanes are phase-separated, containing first domains of hard segments and second domains of soft segments, with the two domains exhibiting different solubility properties with respect to interpenetration of monomers. In polyurethanes, the hard segments are disposed primarily within the ordered domains and the soft segments are disposed primarily within the disordered (amorphous) domains. (The starting polymer may contain more than two domains, of course, without departing from the scope of the invention.) This difference in properties between the two domains of the phase-separated polymer enables the process of this invention to impart new properties to the polymer that can extend throughout the bulk of the material or throughout only a portion of the material, e.g., in a particular region or in a gradient. For example, a non-lubricious polymer can be made lubricious; an otherwise non-conductive polymer can be made conductive; and an otherwise non-permeable polymer can be made permeable. Moreover, the process can be performed repeatedly to introduce more than one new property to the starting polymer.

In some embodiments, phase separation in the polymer allows for differential swelling of one or more separated phases within the polymer with, e.g., a solvent and/or monomer, which is then used to impart new properties. According to the invention, for example, lubriciousness can be introduced to an otherwise non-lubricious material by adding and polymerizing ionic monomers. In one embodiment, a polymer material with high mechanical strength and a lubricious surface can be made from an otherwise non-lubricious, hydrophobic polymer and a hydrophilic polymer derived from ionizable, vinyl monomers. By converting otherwise hydrophobic materials into biphasic materials with both solid and liquid (water) phases, the present invention addresses a need in the art for lubricious, high strength materials for use in medical, commercial, and industrial applications.

Figure 1B:
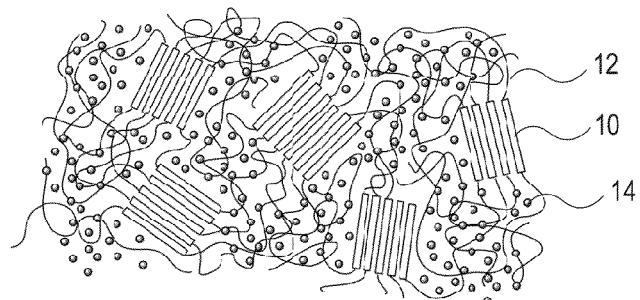
Figure 1C:
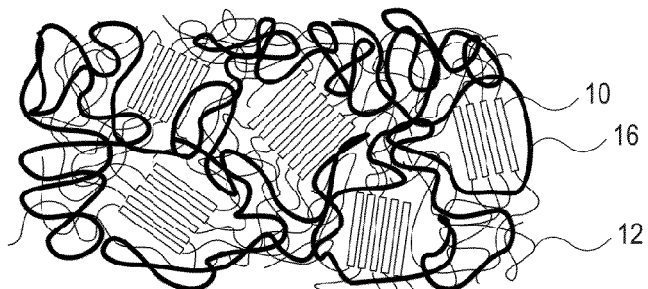

FIGS. 1A-D illustrate the process with respect to a thermoplastic polyurethane-based polymer containing a network of hard segments 10 (shown as open rectangles) and soft segments 12 (shown as lines). In FIG. 1B, the soft segments 12 are swollen with ethylenically unsaturated monomers with or without ionizable functional groups such as vinyl-based monomer 14 (shown as circles) and optional solvent, along with an initiator and cross-linker (not shown), while mostly not affecting the hard segment material. This swelling process is not dissolution of the polymer; the hard segments act as physical crosslinks to hold the material together as the soft segments are imbibed with the monomer(s) and optional solvent(s). After polymerization and cross-linking of the monomers, a second network 16 (shown as dark lines in FIGS. 1C and 1D) is formed in the presence of the first network to create an IPN in which the second polymer (i.e., the polymerized monomer) is primarily sequestered within the soft, amorphous domain of the first polymer. Despite some degree of molecular rearrangement and further phase separation, the hard segments largely remain ordered and crystalline, providing structure and strength to the material.

Figure 1D:
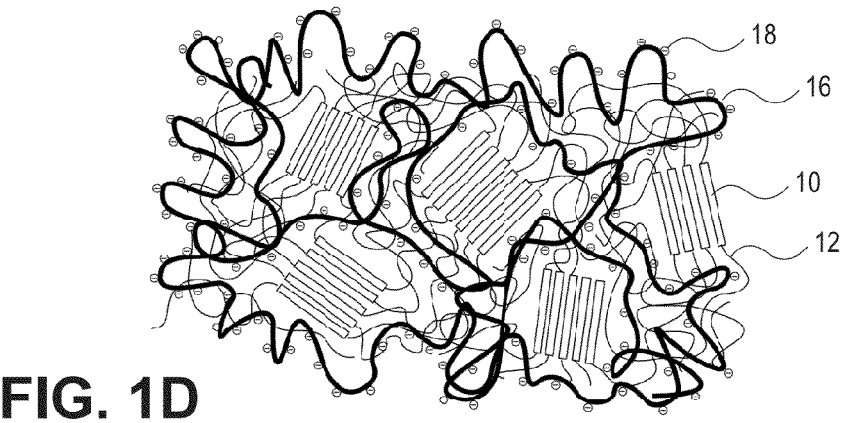

The new properties provided by this IPN depend on the properties of the polymerized monomers that were introduced and on any optional post-polymerization processing. Examples of such new properties include lubriciousness, conductivity, hardness, absorbency, permeability, photoreactivity and thermal reactivity. For example, as shown in FIG. 1D, after optional swelling in a buffered aqueous solution, the second network of the IPN of FIG. 1C becomes ionized 18, and the IPN is water-swollen and lubricious. Thus, hydrophilicity (i.e., water absorbency) can be introduced into an otherwise hydrophobic material. A hydrophobic polymer material such as polyurethane or ABS can be infiltrated with various ionic polymers such as polyacrylic acid and/or poly (sulfopropyl methacrylate) such that it absorbs water.

In addition to absorbency, various levels of permeability (water, ion, and/or solute transport) can be introduced into an otherwise non-permeable material. For example, a hydrophobic polymer material such as polyurethane or ABS can be infiltrated with an ionic polymer such as polyacrylic acid and/or poly(sulfopropyl methacrylate) so that it absorbs water, as described above. This hydration of the bulk of the material allows for the transport of solutes and ions. The transport of solutes and ions and permeability to water is made possible by phase continuity of the hydrated phase of the IPN. This is useful in various applications, including drug delivery, separation processes, proton exchange membranes, and catalytic processes. The permeability can also be utilized to capture, filter, or chelate solutes as a liquid flows over or through the material. Furthermore, because of this permeability, the materials of the present invention can be bestowed with increased resistance to creep and fatigue relative to their component hydrophobic polymers due to their ability to re-absorb fluid after sustained or repetitive loading.

Conductivity can be introduced into an otherwise non-conductive material. For example, an insulating polymer material such as polyurethane can be infiltrated with a conductive polymer (a polyelectrolyte) so that at least part of the hybrid material is conductive to electric current.

The invention also includes the alteration of chemical groups of the second polymer and the use of tethering points in the second polymer for another polymer, molecule or biomolecule. Also, any of the domains can be doped with any number of materials, such as antioxidants, ions, ionomers, contrast agents, particles, metals, pigments, dyes, biomolecules, polymers, proteins and/or therapeutic agents.

The first polymer can be additionally crosslinked or copolymerized with the second polymer if, for example, acryloxy, methacryloxy-acrylamido-, allyl ether, or vinyl functional groups are incorporated into one end or both ends of the polyurethane prepolymer and then cured by UV or temperature in the presence of an initiator. For instance, a polyurethane dimethacrylate or polyurethane bisacrylamide can be used in the first network by curing in the presence of a solvent (such as dimethylacetamide) and then evaporating the solvent. The addition of chemical crosslinks (rather than just physical crosslinks) to the IPN adds a level of mechanical stability against creep or fatigue caused by continuous, dynamic loading.

In addition, a multi-arm (multifunctional) polyol or isocyanate can be used to create crosslinks in the polyurethane. In this case, a fully interpenetrating polymer network is created (rather than a semi-interpenetrating polymer network). The result is a composite material with the high strength and toughness of polyurethane and the lubricious surface and biphasic bulk behavior of the poly(acrylic acid). Alternatively, other crosslinking methods can be used, including but not limited to gamma or electron-beam irradiation. These features are especially important for bearing applications such as artificial joint surfaces, or as more biocompatible, thrombo-resistant, long-term implants in other areas of the body such as the vascular system or the skin. Being swollen with water also allows imbibement with solutes such as therapeutic agents or drugs for localized delivery to target areas of the body.

In another embodiment of the present invention, the first polymer can be linked to the second polymer. For example, polyurethane can be linked through a vinyl-end group. Depending on the reactivity ratio between the end group and the monomer being polymerized, different chain configurations can be yielded. For instance, if the reactivity of the monomer with itself is much greater than the end group with the monomer, then the second polymer will be almost completely formed before the addition of the first polymer to the chain. On the other hand, if the reactivity of the monomer and the end group are similar, then a random grafting-type copolymerization will occur. The monomers and end groups can be chosen based on their reactivity ratios by using a table of relative reactivity ratios published in, for example, The Polymer Handbook. The result of these will be a hybrid copolymer/interpenetrating polymer network.

Any number or combinations of ethylenically unsaturated monomers or macromonomers (i.e., with reactive double bonds/vinyl groups) can be used alone or in combination with various solvents and selectively introduced into one or more of the phases of the polymer as long as at least 2% of such monomers is ionizable, i.e., contains carboxylic acid and/or sulfonic acid functional groups. Ethylenically unsaturated monomers with ionizable function groups include acrylic acid (AA) and other sulfonic acid-based monomers. The ethylenically unsaturated aspect of these includes acrylic, methacrylic, acrylamide, allyl ether, etc., as has been disclosed herein. Other monomers include but are not limited to dimethylacrylamide, acrylamide, NIPAAm, methyl acrylate, methyl methacrylate, hydroxyethyl acrylate/methacrylate, and any vinyl-based monomer containing sulfonic acid groups (e.g. acrylamido methyl propane sulfonic acid, vinyl sulfonic acid, 3-sulfopropyl acrylate (or methacrylate), 2-methyl-2-propene-1-sulfonic acid sodium salt 98%, or any monomers in which sulfonic acid is conjugated (allyl ethers, acrylate/methacrylates, vinyl groups, or acrylamides). The monomer can also include any monomers containing carboxylic acid groups conjugated to allyl ethers, acrylate/methacrylates, vinyl groups, or acrylamides. In addition, the monomers can be used in combination, such as both carboxyl acid and sulfonic acid containing monomers, to create a carboxylate/sulfonate copolymer. The pendant functional groups on polymers resulting from these monomers and monomer combinations can be subject to subsequent chemical reactions to yield other functionalities to the final polymer.

In one embodiment, a preformed, thermoplastic polymer may be immersed in acrylic acid (or in a solution of acrylic acid (1%-100%) or other vinyl monomer solution) along with about 0.1% v/v crosslinker (e.g., triethylene glycol dimethacrylate or N,N methylene bisacrylamide) with respect to the monomer and about 0.1% v/v photoinitiator (e.g. 2-hydroxy-2-methyl propiophenone) with respect to the monomer. The acrylic acid solution can be based on water, salt buffer, or organic solvents such as dimethylacetamide, acetone, ethanol, methanol, isopropyl alcohol, toluene, dichloromethane, propanol, dimethylsulfoxide, dimethyl formamide, or tetrahydrofuran. The polymer may be swollen by the monomer due to solvation of the soft segments in the polymer. The monomer content in the swollen polymer can range from as little as about 1% to up to about 90%.

The monomer-swollen polymer may then be removed, placed in a mold made of glass, quartz, or a transparent polymer, then exposed to UV light (or elevated temperature) to initiate polymerization and crosslinking of the monomers. Alternatively, instead of using a mold, the monomer-swollen polymer can be polymerized while fully or partially exposed to air or an inert atmosphere (e.g., nitrogen or argon), or alternatively in the presence of another liquid such as an oil (e.g., paraffin, mineral, or silicone oil). For medical applications, it is possible that polymerization step can be performed in vivo without a mold.

Depending on the initiator used, exposure to UV light, IR, or visible light, a chemical, electrical charge, or elevated temperature leads to polymerization and crosslinking of the ionizable monomers within the hydrophobic polymer. As an example, acidic monomers (e.g. acrylic acid) are polymerized to form an ionic polymer within a preformed thermoplastic, hydrophobic matrix, forming an interpenetrating polymer network ("IPN"). Solvents can be extracted out by heat and convection or by solvent extraction. Solvent extraction involves the use of a different solvent (such as water) to extract the solvent from polymer, while heat or convection relies upon evaporation of the solvent. Depending on the pKa of the ionic polymer (e.g., pKa of PAA=4.7), an acidic pH would leave the ionic polymer more protonated while a more basic pH would leave it more ionized.

Swelling of the IPN in aqueous solution such as phosphate buffered saline (or other buffered salt solution) at neutral pH will lead to ionization of the poly(acrylic acid) and further swelling with water and salts. The resulting swollen IPN will have a lubricious surface conferred by the hydrophilic, charged poly(acrylic acid) and high toughness and mechanical strength conferred by the thermoplastic. In the case of a polyurethane-based IPN, the IPN will have a structure in which crystalline hard segments in the polyurethane act as physical crosslinks in the first network, while chemical crosslinks will be present in the second network.

The materials can also be crosslinked after synthesis using gamma radiation or electron beam radiation. In one example, polyurethane/polyacrylic acid can be synthesized and then crosslinked by gamma irradiation, for instance with doses of, for example, 5, 10, 15, 20, or 25 kGy. In this case, the polymerization of polyacrylic acid would be done in the absence of a crosslinker, and after formation of the polymer blend (physical IPN), the material would be exposed to gamma radiation. This would have the dual purpose of sterilizing and crosslinking the polyurethane. It is known in the art that crosslinking of poly(acrylic acid) hydrogels using gamma irradiation shows a dose-dependence to the crosslinking of the polymer. This process can also be applied to other combinations of first and second network polymers, e.g., polyurethane and polymethyl methacrylate, ABS and polyacrylic acid, etc.

In addition to the starting thermoset and thermoplastic hydrophobic polymers identified above, modifications to and derivatives of such polymers may be used, such as sulfonated polyurethanes. In the case of the polyurethanes, the polyurethane polymer can be a commercially available material, a modification of a commercially available material, or a new material. Any number of chemistries and stoichiometries can be used to create the polyurethane polymer. For the hard segment, isocyanates used are 1,5 naphthalene diisocyanate (NDI), isophorone isocyanate (IPDI), 3,3-bitoluene diisocyanate (TODI), methylene bis(p-cyclohexyl isocyanate) ($H_{12}MDI$), cyclohexyl diisocyanate (CHDI), 2,6 tolylene diisocyanate or 2,4 toluene diisocyanate (TDI), hexamethyl diisocyanate, or methylene bis(p-phenyl isocyanate). For the soft segment, chemicals used include, for example polyethylene oxide (PEO), polypropylene oxide (PPO), poly(tetramethylene oxide) (PTMO), hydroxy terminated butadiene, hydroxybutyl terminated polydimethylsiloxane (PDMS), polyethylene adipate, polycaprolactone, polytetramethylene adipate, hydroxyl terminate polyisobutylene, polyhexamethylene carbonate glycol, poly (1,6 hexyl 1,2-ethyl carbonate, and hydrogenated polybutadiene. Any number of telechelic polymers can be used in the soft segment, if end-groups that are reactive with isocyanates are used. For instance, hydroxyl- or amine-terminated poly(vinyl pyrrolidone), dimethylacrylamide, carboxylate or sulfonated polymers, telechelic hydrocarbon chains (with hydroxyl and/or amine end groups), dimethylolpropionic acid (DMPA), or these in combination with each other or with other soft segments mentioned above (e.g., PDMS) can be used. Ionic soft segments (or chain extenders) such as dihydroxyethyl propionic acid (DMPA) (or its derivatives) can be used to make a water-dispersible polyurethane, so long as the ionic chain extender does not comprise more than 2% of the material.

Chain extenders include, for example, 1,4 butanediol, ethylene diamine, 4,4'methylene bis(2-chloroaniline) (MOCA), ethylene glycol, and hexane diol. Any other compatible chain extenders can be used alone or in combination. Crosslinking chain extenders can be used containing isocyanate-reactive endgroups (e.g. hydroxyl or amine) and a vinyl-based functional group (e.g. vinyl, methacrylate, acrylate, allyl ether, or acrylamide) may be used in place of some or all of the chain extender. Examples include 1,4 dihydroxybutene and glycerol methacrylate. Alternatively, crosslinking can be achieved through the use of a polyol such as glycerol which contains greater than two hydroxyl groups for reaction with isocyanates.

In some embodiments, at least 2% of the hydrophilic monomers in the second network is ionizable and anionic (capable of being negatively charged). In one such embodiment, poly(acrylic acid) (PAA) hydrogel is used as the second polymer network, formed from an aqueous solution of acrylic acid monomers. Other ionizable monomers include ones that contain negatively charged carboxylic acid or sulfonic acid groups, such as methacrylic acid, 2-acrylamido-2-methylpropanesulfonic acid, sulfopropyl methacrylate (or acrylate), vinyl sulfonic acid, or vinyl-conjugated versions of hyaluronic acid, heparin sulfate, and chondroitin sulfate, as well as derivatives, or combinations thereof. The second network monomer may also be positively charged or cationic. These other monomers can also be in a range of 1%-99% in either water or organic solvent, or be pure (100%). One embodiment of the monomer used to form the second network can be described by the following characteristics: (1) it is capable of swelling the polyurethane, (2) capable of polymerizing, and (3) is ionizable.

Other embodiments use a co-monomer in addition to the ionic polymer that may be non-ionic, such as acrylamide, methacrylamide, N-hydroxyethyl acrylamide, N-isopropylacrylamide, methylmethacrylate, N-vinyl pyrrolidone, 2-hydroxyethyl methacrylate, 2-hydroxyethyl acrylate or derivatives thereof. These can be copolymerized with less hydrophilic species such as methylmethacrylate or other more hydrophobic monomers or macromonomers. These can also be polymerized alone or copolymerized with the aforementioned hydrophilic and/or ionizable monomers.

Crosslinked linear polymer chains (i.e., macromolecules) based on these monomers may also be used in the second network, as well as biomacromolecules (linear or crosslinked) such as proteins and polypeptides (e.g., collagen, hyaluronic acid, or chitosan). The choice of the second material will depend on the target application, for instance in orthopaedic applications, hyaluronic acid may be useful because it is a major component of joint cartilage. In addition, biological molecules may carry certain benefits such as intrinsic biocompatibility or therapeutic (e.g., wound healing and/or antimicrobial) properties that make them useful as material components.

Any type of compatible cross-linkers may be used to crosslink the second network in the presence of any of the aforementioned first networks such as, for example, ethylene glycol dimethacrylate, ethylene glycol diacrylate, diethylene glycol dimethacrylate (or diacrylate), triethylene glycol dimethacrylate (or diacrylate), tetraethylene glycol dimethacrylate (or diacrylate), polyethylene glycol dimethacrylate, or polyethylene glycol diacrylate, methylene bisacrylamide, N,N'-(1,2-dihydroxyethylene)bisacrylamide, derivatives, or combinations thereof. Any number of photoinitiators can also be used depending on their solubility with the precursor solutions/materials. These include, but are not limited to, 2-hydroxy-2-methyl-propiophenone and 2-hydroxy-1-[4-(2-hydroxyethoxy)phenyl]-2-methyl-1-propanone. In addition, other initiators such as benzoyl peroxide, 2-oxoglutaric acid, azobisisobutyronitrile, or potassium persulfate (or sodium persulfate) can be used. For instance, benzoyl peroxide is useful for temperature-initiated polymerizations, while azobisisobutyronitrile and sodium persulfate are useful as radical initiators.

In another embodiment, a solvent can be used as a "trojan horse" to deliver monomers that otherwise would not mix (or solubilize with) the polymer to one (or more) phases of the polymer. The solvent must be carefully chosen based on the specific qualities and phases of the polymer and monomers. For instance, acetic acid is capable of swelling but does not dissolve many polyurethanes. Therefore, acetic acid can be used to carry other monomers such an acrylamide solution, that otherwise would not enter polyurethane, into the bulk of the polyurethane. This allows the acrylamide to be selectively polymerized inside one phase of the polyurethane. The acetic acid can then be washed out leaving behind a polyurethane with one or more new properties. Other solvents that can be used include, but are not limited to, dichloromethane, methanol, propanol, butanol, (or any alkyl alcohol), acetone, dimethylacetamide, dimethylformamide, dimethylsulfoxide, tetrahydrofuran, diethylether, or combinations of these. Taking into account the solubilities in the phases of the polymer, solvents with varying degrees of swelling of one can be chosen. Solubilities of the solvents and components of the material to be swollen can be obtained from polymer textbooks such as The Polymer Handbook or can be measured experimentally.

The present invention can be used to form a bulk-interpenetrated coating on a polymeric material. This coating is inextricably entangled with the underlying polymer matrix, and is in contrast to conventional surface coatings in which a material is grafted or tethered to a surface. In one example of a bulk-interpenetrated coating, a thermoplastic polymer is coated on one or more sides or is immersed in an ionizable monomer such as acrylic acid in the presence of a photoinitiator and a crosslinking agent. The thermoplastic is then placed in a mold and then exposed to an initiator (e.g., UV light or heat) for a predetermined period of time. The mold can be fully or partially transparent and/or masked to facilitate regionally specific curing of the monomer. The modified material is then immersed in buffered saline solution to neutralize the ionic polymer and render the surface lubricious and hydrophilic. The modified plastic can then be further remolded by application of heat, solvent, and/or pressure and then shaped to the desired dimensions. The modified plastic can then be bonded to various surfaces such as metal, glass, plastic, or other materials by applying heat or solvent (such as acetone) to the unmodified plastic surface and bringing the surface in contact with the surface of interest.

Among the applications of the invention are the creation of hydrophilic, lubricious sidings or coatings to reduce drag and/or biofilm formation and/or barnacle formation in marine vessels, diving or swimming suits, other water crafts or waterborne objects, or pipes. In addition, the invention can be used as a method for making bearings and moving parts for applications such as engines, pistons, or other machines or machine parts. The invention can also be used in artificial joints systems or long-term implants in other areas of the body, such stents and catheters for the vascular or urinary system or implants, patches, or dressings for the skin.

Figure 2:
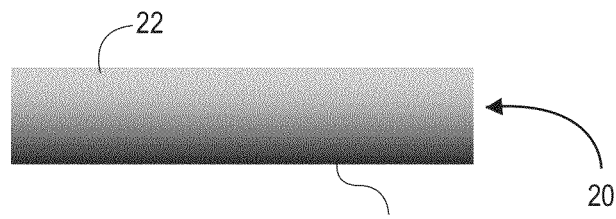
FIG. 2 illustrates a composition gradient formed in an article along a thickness direction
Figure 3:
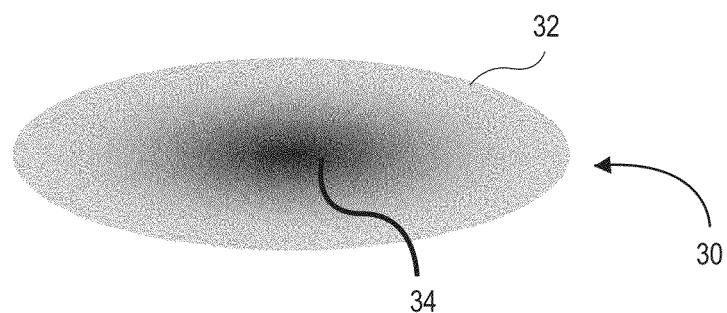
FIG. 3 illustrates a composition gradient formed in an article along a radial direction

FIGS. 2 and 3 illustrate how the invention can be used to create a composition gradient within a starting homopolymer. In FIG. 2, a gradient is formed in material 20 along a thickness direction, with the IPN formed on one side 22 and extending in a diminishing concentration to another side 24, e.g., substantially only homopolymer. In FIG. 3, the IPN concentration gradient is radial within material 30, with the outer surface 32 being the highest concentration of IPN and the center or core 34 having the lowest concentration of IPN. A reverse gradient can also be made in the case of a cylinder or a sphere, with the IPN disposed in the core of the shape and the hydrophobic polymer being disposed in the outer aspect of the shape. This is useful in creating a conductive semi-IPN wire that is encapsulated within an insulating hydrophobic material via a gradient composition.

Figure 4A:
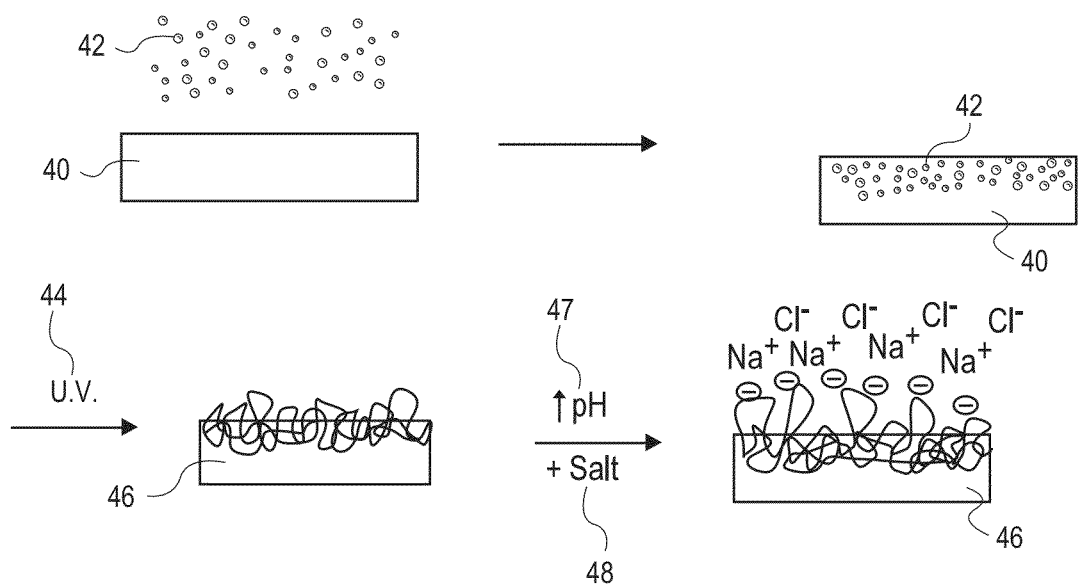
FIG. 4A illustrates a method of fabricating a thermoplastic gradient IPN according to the present invention.

FIG. 4A illustrates a method of fabricating a thermoplastic gradient IPN according to the present invention. One side of the thermoplastic material 40 is imbibed with a monomer solution 42 along with a photoinitiator (not shown) and a crosslinker (not shown), and then the monomer is polymerized and crosslinked (e.g., with UV light 44) within the thermoplastic to form a gradient IPN 46. Increasing the pH to neutral 47 and introducing salt 48 into the surrounding fluid leads to ionization of the 2nd polymer network. Alternatively, non-ionic monomers can be used as the basis in a part (to form a copolymer). The non-ionic polymer would not be ionized by the buffer solution, but would still create a hydrophilic surface. Either type of monomer system can be used in conjunction with either water or an organic solvent.

In one embodiment, a TP/PAA IPN can be created in a gradient if polyurethane ("PU") is swollen in AA on one side only or if the swelling time is limited such that diffusion of the monomers through the bulk of the TP is not complete. This is especially useful in the creation of osteochondral grafts for orthopaedic joint replacement materials. For instance, in the case of a cartilage replacement material, one side of the material is made lubricious and water swollen, while the other remains a solid (pure thermoplastic). In between is a transition between a TP/PAA IPN and TP, with decreasing PAA content from one surface to the other. Alternatively, bulk materials with a TP/PAA IPN outer aspect and PU-only "core" can be made if the diffusion of AA into the TP is precisely controlled by timing the infiltration of the monomers into the bulk. The differential swelling that results from this configuration can lead to remaining stresses (compressive on the swollen side, tensile on the non-swollen side) that can help enhance the mechanical and fatigue behavior of the material. In the case of a material with a thickness gradient, the base of thermoplastic-only material can be used for anchoring, adhering, or suturing the device to the anatomical region or interest. This base can be confined to a small area or be large (e.g., a skirt) and can extend outward as a single component or multiple components (e.g., straps). The internal stresses built up within the thermoplastic during processing or after swelling can be reduced by temperature-induced annealing. For instance, temperatures of 60-120 degrees Celsius can be used for various times (30 minutes to many hours) to anneal the polymer, and the heat can be applied in an oven, by a hot surface, by radiation, or by a heat gun. The thermoplastic can later be crosslinked using, for example, gamma or electron beam radiation.

FIG. 4B illustrates how the properties of gradient IPN's can vary to produce the desired composition. FIG. 4C illustrates how the concentration gradient of the hydrophobic polymer and the ionic polymer can vary across the thickness (between the two surfaces) of a gradient IPN. The composition gradient yields a property gradient in which the IPN is hydrated and more compliant on one side, and less hydrated (or not hydrated) and stiff on the other.

Figure 5:
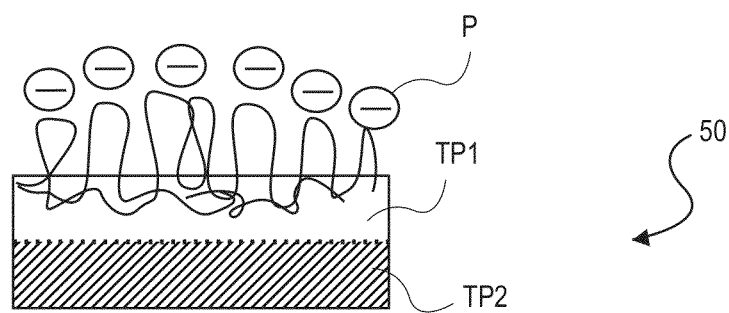
FIG. 5 illustrates a laminate structure or an IPN or semi-IPN.

Articles made from the IPN's and semi-IPN's of this invention may also be formed in a laminate structure, as illustrated in FIG. 5. In one example, the IPN structure 50 is comprised of a hydrophilic polymer (P) such as poly(acrylic acid) that is interpenetrating a first thermoplastic (TP1) such as polyether urethane, which is formed on top of a second thermoplastic (TP2) such as polycarbonate urethane. Both TP1 and TP2 can be themselves comprised of multiple layers of various hardnesses and properties. In addition, many more than two thermoplastic layers can be used, and one or more of the thermoplastics can be crosslinked. Finally, non-thermoplastic elements can be incorporated into this construct.

Articles formed from the gradient or homogeneous IPN's and semi-IPN's of this invention may be shaped as desired. FIG. 6 illustrates shaping of a gradient IPN article. This process may also be used to shape a homogeneous IPN or semi-IPN.

As shown in FIG. 6A, heat 61 can be used to re-anneal the physical crosslinks in the polymer (e.g., the hard segments in the polyurethane) in the thermoplastic side 50 of the gradient IPN to lead to different desired curvatures after bending (e.g., over a mold or template) and cooling. FIG. 6B illustrates both convex 62 and concave 64 curvatures on the thermoplastic side of the gradient IPN. Other shapes may be formed, of course, as desired. The use of thermoplastic facilitates molding of a device to a desired shape by, for example, injection molding, reactive injection molding, compression molding, or alternatively, dip-casting. The molded device can then be subjected to subsequent network infiltration and polymerization steps to yield the new IPN material.

Shaping of IPN and semi-IPN articles according to this invention may be formed in situ, such as within a human body. For example, FIGS. 7A-B illustrate heating 71 of a thermoplastic gradient IPN 70 to enable it to wrap around the curvature of a femoral head 72. FIGS. 7C-D illustrate the application of heat 74 to a thermoplastic gradient IPN 73 to enable it to adapt to the curvature of a hip socket 75.

Shaped or unshaped IPN and semi-IPN articles made according to this invention may be attached to other surfaces. FIG. 8A-D shows how a bonding agent 81 such as a solvent, cement, or glue can be used to attach the thermoplastic gradient IPN article 80 to a surface 82 at a bonded interface 83. Addition of the solvent, for example, causes the material to dissolve locally, and after contact with a surface and drying of the solvent, the thermoplastic adheres to the surface. This method can be used to create "paneling" of the present invention of various objects, including but not limited to marine vessel hull surfaces. A "coating" can be applied by vacuum forming the material over the contours of the vessel or a part of the vessel. A similar approach can be used to attach a gradient IPN to bone surfaces in joints.

The composition of this invention, formed, e.g., by the method of this invention, may be used in a variety of settings. One particular use is as artificial cartilage in an osteochondral graft. The present invention provides a bone-sparing arthroplasty device based on an interpenetrating polymer network that mimics the molecular structure, and in turn, the elastic modulus, fracture strength, and lubricious surface of natural cartilage. Emulating at least some of these structural and functional aspects of natural cartilage, the semi-IPNs and IPNs of the present invention form the basis of a novel, bone-sparing, "biomimetic resurfacing" arthroplasty procedure. Designed to replace only cartilage, such a device is fabricated as a set of flexible, implantable devices featuring lubricious articular surfaces and osteointegrable bone-interfaces.

In principle, the device can be made for any joint surface in the body. For example, a device to cover the tibial plateau will require an analogous bone-preparation and polymer-sizing process. For a device to cover the femoral head in the hip joint, a cap shaped device fits snugly over the contours of the femoral head. For a device to line the acetabulum, a hemispherical cup-shaped device stretches over the lip and can be snapped into place in the socket to provide a mating surface with the femoral head. In this way, both sides of a patient's hip joint can be repaired, creating a cap-on-cap articulation. However, if only one of the surfaces is damaged, then only one side may be capped, creating a cap-on-cartilage articulation. In addition, the materials of the present invention can be used to cap or line the articulating surfaces of another joint replacement or resurfacing device (typically comprised of metal) to serve as an alternative bearing surface.

To create a cap-shaped device using the present invention for the shoulder joint (also a ball-and-socket joint), a process similar to that of the hip joint is used. For instance, a shallow cup can be created to line the inner aspect of the glenoid. Furthermore, devices for other joints in the hand, fingers, elbow, ankles, feet, and intervertebral facets can also be created using this "capping" concept. In one embodiment in the distal femur, the distal femur device volume follows the contours of the bone while sparing the anterior and posterior cruciate ligaments.

In one embodiment of prosthetic cartilage formed according to this invention, a polyether urethane device pre-formed with shore hardness of 75D is injection molded. This device is then solution casted in a Vitamin E-containing solution containing polyether urethane formulated to a dry shore hardness of 55D (e.g., 25% Elasthane™ 55D in dimethylacetamide). The casted layer may then be dried in a convection oven to remove the solvent. The device may then be immersed in a solution of acrylic acid, photoinitiator, and crosslinker for 24 hours, and then placed over a glass mold and exposed to UV light. The resulting device may then be soaked and washed in phosphate buffered saline. This process is used to create either convex or concave devices for arthroplasty applications. The injection-molded pre-form has on one of its sides a plurality of spaces (pores or features) that make capable of being anchored to bone with traditional orthopaedic bone cement.

Although a commercially available polyurethane product, Elasthane, Bionate, Pursil, or Sylgard, was used in some examples, it is understood in the art that any suitable hydrophobic thermoset/thermoplastic polymer or material may be used and there is no limitation as to the particular commercial products/tradenames described herein.

In another embodiment of the device, a polycarbonate urethane pre-formed with surface features on one side is fabricated, followed by dip-casting of one of its sides in a solution of polyether urethane and then subjected to a process similar to the one above. In still another embodiment, a polyether urethane pre-form of shore hardness 55D (e.g., Elasthane™ 55D) is injection molded, followed by immersion in a monomer solution as above. After curing of the second polymer network, the device is dip-casted on one side with polycarbonate urethane of shore hardness 75D. In any of these embodiments, additional surface features can be added to the bone interface side of the device through a number of means, including but not limited to machining (lathe and end-mill), solution casting, solvent-welding, ultrasonic welding, or heat-welding.

Porous polycarbonate urethane IPN and semi-IPN structures may be made according to this invention. Particles (size range: 250-1500 μm) of polycarbonate urethane, including but not limited to Bionate® 55D, Bionate® 65D, and Bionate® 75D, may be sintered in a mold using heat (220-250° C.), pressure (0.001-100 MPa), and/or solvent for 10-30 min. The structures will have a final pore size of 50-2000 μm, porosity of 15-70%, and a compressive strength exceeding 10 MPa. The final structures will have porosity to promote tissue ingrowth/integration for, medical and veterinary applications. This construct can be used alone or with an overlying bearing surface made from any of the lubricious polymers described in this invention. This material could be used as a cartilage replacement plug in joints of the body where cartilage has been damaged, as described below.

The composition of this invention, made, e.g., according to the method of this invention, may be used as a fully or partially synthetic osteochondral graft. The osteochondral graft consists of a lubricious, cartilage-like synthetic bearing layer that may be anchored to porous bone or a synthetic, porous bone-like structure. The bearing layer has two regions: a lubricious surface layer and a stiff, bone anchoring layer. In one embodiment, the top, lubricious region of the bearing layer consists of an interpenetrating polymer network that is composed of two polymers. The first polymer may be a hydrophobic thermoplastic with high mechanical strength, including but not limited to polyether urethane, polycarbonate urethane, silicone polyether urethane, and silicone polycarbonate urethanes, or these materials with incorporated urea linkages, or these materials with incorporated urea linkages (e.g. polyurethane urea). The second polymer may be a hydrophilic polymer derived from ionizable, vinyl monomers, including but not limited to acrylic acid and/or sulfopropyl methacrylate. The bottom region of the bearing layer (bone anchoring layer) may be a stiff, non-resorbable thermoplastic that can be caused to flow with ultrasonic welding vibration, ultrasonic energy, laser energy, heat, RF energy and electrical energy. The bone anchoring layer is used to anchor the bearing layer to bone or a bone-like porous structure. If porous bone is used, it can be cancellous bone from a human or animal. If a synthetic bone-like material is used, it can consist of porous calcium-phosphate (and/or other materials, including but not limited to porous carbonated apatite, beta-tricalcium phosphate, or hydroxyapatite), or a porous resorbable or non-resorbable thermoplastic as described above, including but not limited to polycarbonate urethane, polyether urethane, PLA, PLLA, PLAGA, and/or PEEK. The bearing layer is anchored to the porous bone or bone-like structure via application of pressure combined with energy that cause the bone anchoring material to melt and flow into the pores or spaces of the bone or bone-like structure, after which the energy source is removed and the material resolidifies. The energy source can include but is not limited to vibration, ultrasonic energy, laser energy, heat, RF energy, and electrical energy.

The following figures illustrate various embodiments of the present invention as a device to partially or completely resurface damaged joints in the body of mammals (animals or human). These devices can be fixated to bone through any number of means, such as a press-fit, screws (metal or plastic, either resorbable or nonresorbable), sutures (resorbable or nonresorbable), glue, adhesives, light-curable adhesives (e.g. polyurethane or resin-based), or cement (such as polymethylmethacrylate or calcium phosphate, or dental cements).

Figure 9A:
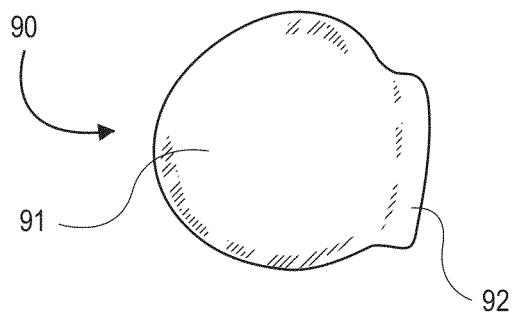
FIGS. 9A-D illustrate how an osteochondral graft implant formed from an IPN or semi-IPN of this invention can be used to replace or augment cartilage within a joint.
Figure 9B:
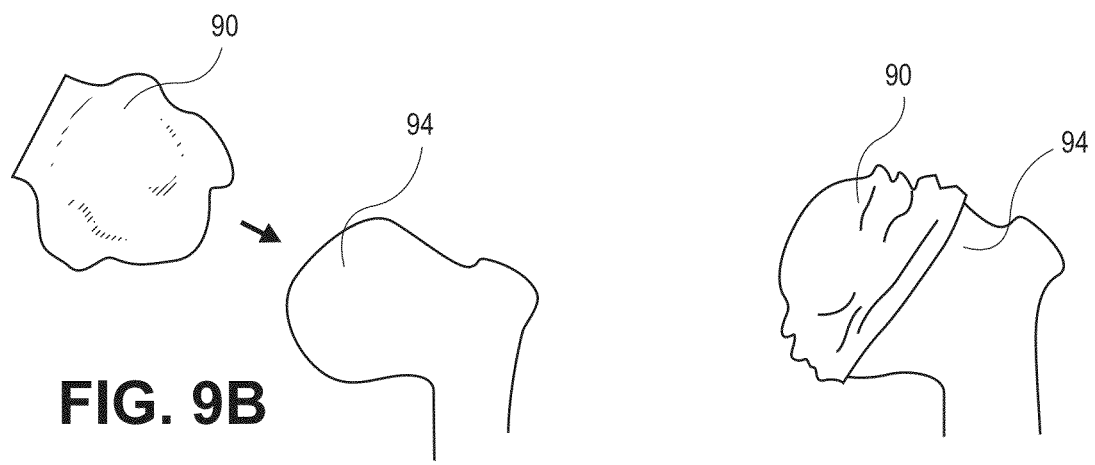
Figure 9C:
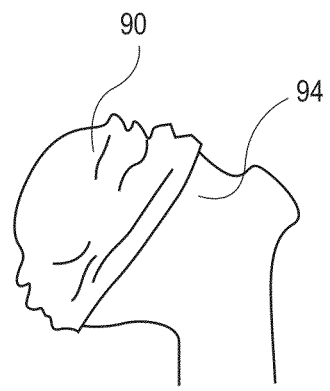
Figure 9D:
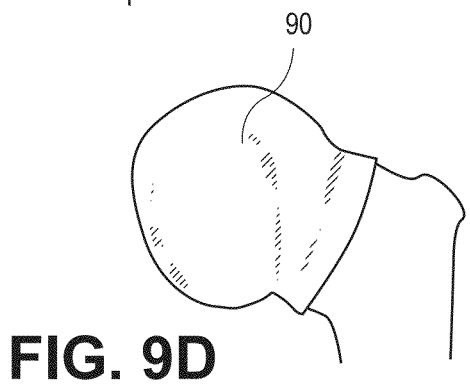

FIGS. 9A-D illustrate how an osteochondral graft implant formed from an IPN or semi-IPN of this invention can be used to replace or augment cartilage within a joint, such as a hip or shoulder joint. As shown in FIG. 9A, the prosthetic cartilage 90 is formed as a sock having a cap portion 91 and an optional collar 92. The prosthesis 90 may be inverted, as shown in FIG. 9B, and slipped over the head 94 of the humerus or femur. In an alternative embodiment shown in FIGS. 10A-B, the prosthesis 90 may include an opening 95 to accommodate a ligament 96 or other anatomical structure.

Implants and other articles may be made in a variety of complex shapes according to the invention. FIGS. 11A-E show osteochondral grafts formed from an IPN or semi-IPN of this invention that may be used singly or in any combination needed to replace or augment cartilage within a knee joint. FIG. 11A shows a osteochondral graft 110 adapted to engage the femoral condyles (or alternatively, just one condyle). FIG. 11B shows osteochondral grafts 111 and 112 adapted to engage one or both sides of the tibial plateau 113. FIG. 11C shows an osteochondral graft 118 adapted to engage the patella 114 and to articulate with an osteochondral graft 119 adapted to engage the patellofemoral groove 115. FIG. 11D show osteochondral grafts 116 and 117 adapted to engage the lateral and medial menisci. FIG. 11E shows how some of these prostheses may be assembled in place within the knee joint.

Figures 12A, 12B:
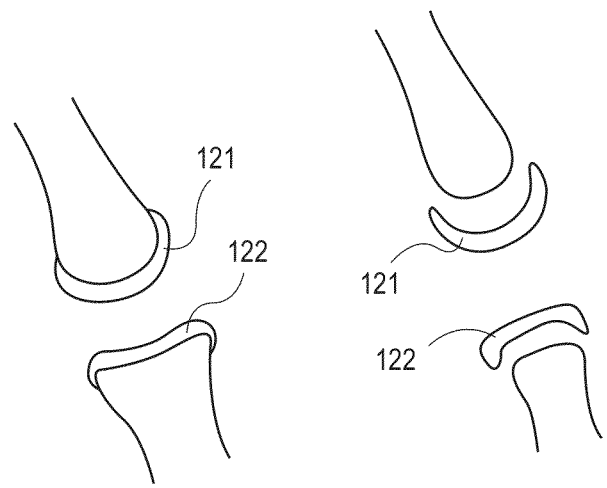
FIGS. 12A-B show osteochondral grafts formed from the IPN's or semi-IPN's of this invention and shaped for use in a finger joint.
Figure 13A:
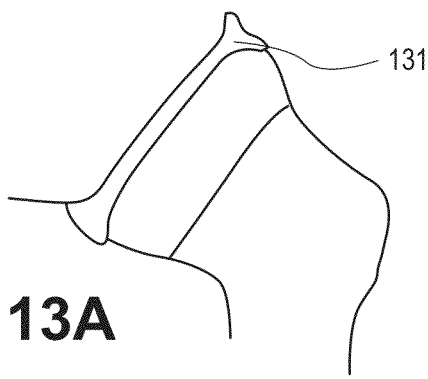
FIGS. 13A-B show a labrum prosthesis formed from an IPN or semi-IPN of this invention for use in replacing or resurfacing the labrum of the shoulder or hip.
Figure 13B:
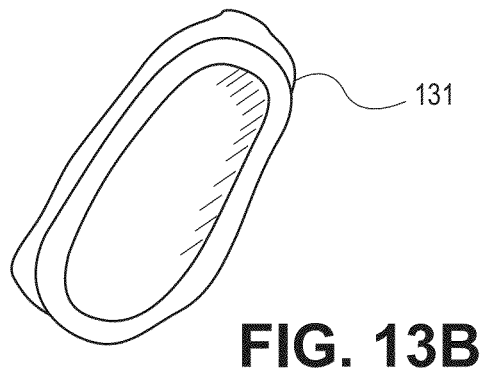

Osteochondral grafts may also be used in other joints, such as in the finger, hand, ankle, elbow, feet or vertebra. For example, FIGS. 12A-B show osteochondral grafts 121 and 122 formed from the IPN's or semi-IPN's of this invention and shaped for use in a finger joint. FIGS. 13A-B show a labrum prosthesis 131 formed from an IPN or semi-IPN of this invention for use in replacing or resurfacing the labrum of the shoulder or hip. FIG. 14 shows the use of an IPN or semi-IPN of this invention as a bursa osteochondral graft 141, labrum osteochondral graft 142, glenoid osteochondral graft 143 and humeral head osteochondral graft 144. FIG. 15 shows the use of an IPN or semi-IPN of this invention as prostheses 151 and 152 for resurfacing intervertebral facets.

The IPN's and semi-IPN's compositions of this invention may be formed as prosthetic cartilage plugs for partial resurfacing of joint surfaces. FIG. 16A shows a prosthetic cartilage plug 160 formed from a gradient IPN composition of this invention. Plug 160 has a stem portion 161 formed on a thermoplastic side of the article and adapted to be inserted into a hole or opening in a bone. The head 162 of the plug is formed to be a lubricious IPN or semi-IPN, as described above. FIG. 16B shows a variation in which porous surfaces are formed on the underside 163 of head 162 and on the base 164 of stem 161. In the embodiment of FIGS. 16C-D, the porous surface is formed only in the center portion 165 of base 164. In all embodiments, stem 161 may be press fit into a hole or opening in the bone, leaving the lubricious IPN surface to be exposed to act as prosthetic cartilage.

Figures 17, 18A, 18B, 19, 20, 21, 22:
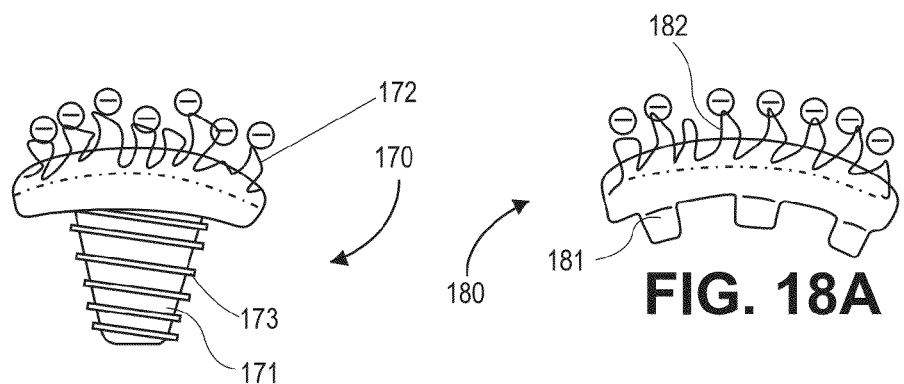
FIG. 17 shows an embodiment of a prosthetic cartilage plug in which the stem is provided with helical ridges to form a screw for fixation of the plug to bone.
FIGS. 18A-B are side and bottom elevational views of an embodiment of a prosthetic cartilage plug having three stems for press fit insertion into holes in the bone for fixation.
FIG. 19 shows an embodiment of a prosthetic cartilage plug in which the exposed head portion is substantially the same diameter as the stem.
FIG. 20 shows an embodiment of a prosthetic cartilage plug in which the exposed head portion is narrower than the stem, and the stem widens toward the base.
FIG. 21 shows an embodiment of a prosthetic cartilage plug in which the stem has circumferential ridges to aid fixation.
FIG. 22 shows an embodiment similar to that of FIG. 19 that adds a rough porous surface to the stem.

FIG. 17 shows an embodiment of a prosthetic cartilage plug 170 in which the stem 171 is provided with helical ridges 173 to form a screw for fixation of the plug to bone. The top surface of the head 172 is a lubricious IPN or semi-IPN, as above.

FIG. 18A-B show an embodiment of a prosthetic cartilage plug 180 having three stems 181 for press fit insertion into holes in the bone for fixation. The top surface of plug head 182 is a lubricious IPN or semi-IPN, as above.

FIG. 19 shows an embodiment of a prosthetic cartilage plug 190 in which the exposed head portion 192 is substantially the same diameter as the stem 191. Stem 191 may be press fit into a hole in the bone for fixation. The top surface of plug head 192 is a lubricious IPN or semi-IPN, as above.

FIG. 20 shows an embodiment of a prosthetic cartilage plug 200 in which the exposed head portion 202 is narrower than stem 201, and stem 201 widens toward base 203. Stem 201 may be press fit into a hole in the bone for fixation. The top surface of plug head 202 is a lubricious IPN or semi-IPN, as above.

FIG. 21 shows an embodiment of a prosthetic cartilage plug 210 in which the stem 211 has circumferential ridges to aid fixation. Stem 211 may be press fit into a hole in the bone for fixation. The top surface of plug head 212 is a lubricious IPN or semi-IPN, as above.

FIG. 22 shows an embodiment similar to that of FIG. 19 that adds a rough porous surface to stem 221. The top surface of plug head 222 is a lubricious IPN or semi-IPN, as above.

Figure 23:
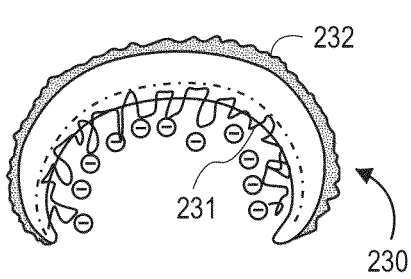
FIG. 23 shows an embodiment of an osteochondral graft formed to physically grip the bone without additional fixation, such as screws or stems.

FIG. 23 shows an embodiment of an osteochondral graft 230 formed to physically grip the bone without additional fixation, such as screws or stems. In this embodiment, the lubricious IPN or semi-IPN portion of the prosthesis is on a concave surface 231 of the device. The opposite convex surface 232 of the device is shaped to match the shape of the bone to which prosthesis 230 will be attached. Surface 232 is porous to facilitate bony ingrowth. The porous material in this case can be fabricated from a porogen method as described in the present invention, with the porogen being sodium chloride, tricalcium phosphate, hydroxyapatite, sugar, and derivatives or combinations thereof. Alternatively, the porosity can be derived from sintering polymer beads (e.g. polyether urethane or polycarbonate urethane) together using heat or solvent.

Figure 24:
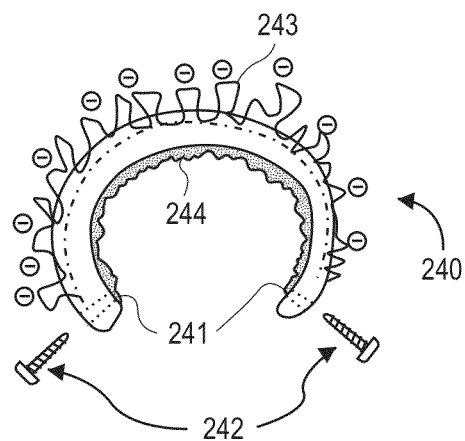
FIG. 24 shows an embodiment of an osteochondral graft having screw holes for screw fixation.

Screw holes may be provided to the osteochondral graft for fixation to the bone. In FIG. 24, prosthesis 240 is provided with two holes 241 for screws 242. The bone-contacting concave side 244 of prosthesis 240 is porous (as above) to promote bony ingrowth and has a shape adapted for physically gripping the bone. The outer convex surface 243 of the prosthesis is a lubricious IPN or semi-IPN, as above.

Figure 25:
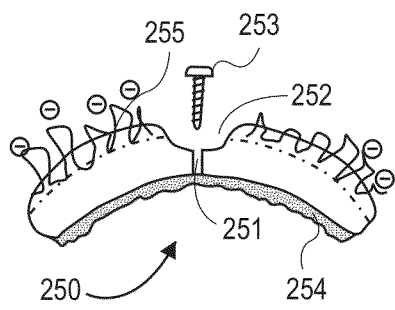
FIG. 25 shows an embodiment of an osteochondral graft having a screw hole and a screw head depression for screw fixation.

In FIG. 25, the osteochondral graft 250 is provided with a screw hole 251 as well as a depression 252 for accommodating the head of a screw 253. The bone-contacting concave side 254 of prosthesis 250 is porous (as above) to promote bony ingrowth and has a shape adapted for physically gripping the bone. The outer convex surface 255 of the prosthesis is a lubricious IPN or semi-IPN, as above.

Figure 26:
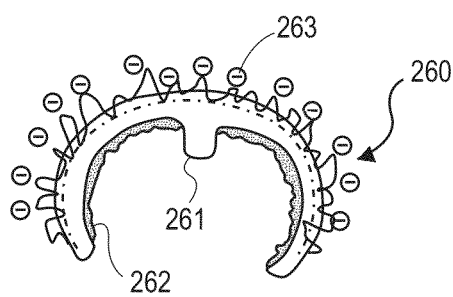
FIG. 26 shows an embodiment of an osteochondral graft having a stem for insertion into a hole in the bone.

FIG. 26 shows an embodiment of an osteochondral graft 260 having a stem 261 for insertion into a hole in the bone. The bone-contacting concave side 262 of prosthesis 260 is porous (as above) to promote bony ingrowth and has a shape adapted for physically gripping the bone. The outer convex surface 263 of the prosthesis is a lubricious IPN or semi-IPN, as above.

Figure 27A:
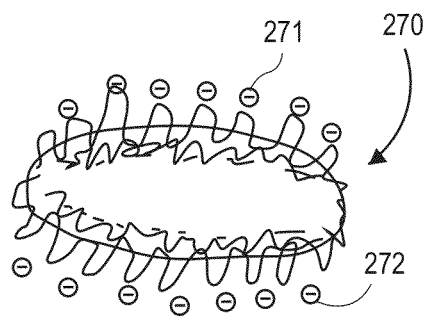
FIGS. 27A-B show embodiments of the composition of this invention used to make two-sided lubricious implants.
Figure 27B:
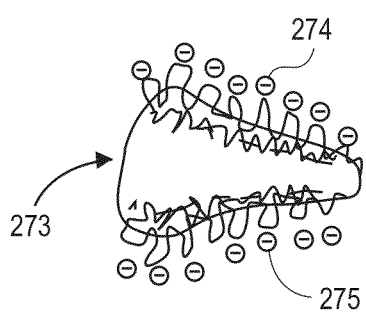

FIGS. 27A-B show embodiments of the composition of this invention used to make two-side lubricious implants. In FIG. 27A, implant 270 is sized and configured to replace an intervertebral disc. Implant 270 has lubricious IPN or semi-IPN surfaces 271 and 272 (formed, e.g., as described above) on its upper and lower sides. FIG. 27B shows a knee spacer 273 having a wedge-shaped cross-section. As with disc prosthesis 270, spacer 273 also has lubricious IPN or semi-IPN surfaces 274 and 275 on its upper and lower sides.

Figure 28:
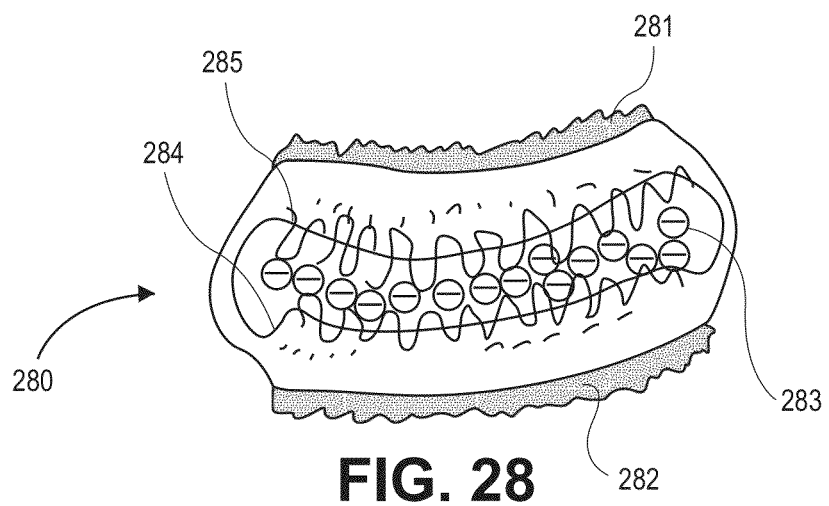
FIGS. 28 and 29 show orthopedic implants that are attached to surfaces of two bones or other anatomic elements that move with respect to each other, such as in a joint.
Figure 29:
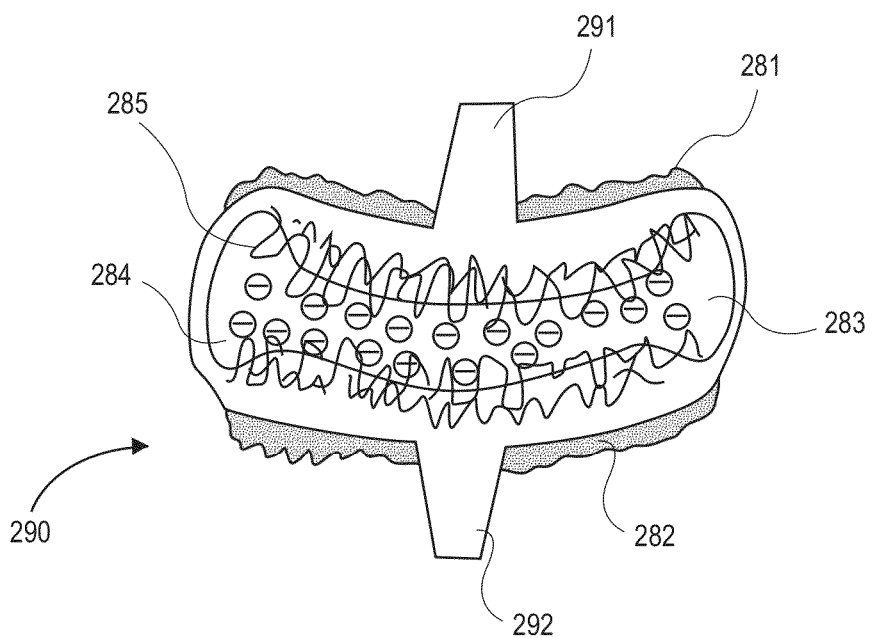

Many of the osteochondral grafts and other implants described above are affixed to a single bone surface. FIGS. 28 and 29 show orthopedic implants that are attached to surfaces of two bones or other anatomic elements that move with respect to each other, such as in a joint. In FIG. 28, implant 280 has upper and lower bone contacting regions 281 and 282 formed to be porous (as described above) to promote bony ingrowth. The interior of implant 280 is a fluid-filled capsule 283. Inwardly facing bearing surfaces 284 and 285 are lubricious IPN or semi-IPN surfaces (as above). Implant 280 can be used, e.g., as an interpositional spacer and as a replacement for the synovial capsule and cartilage of a joint. The implant 290 of FIG. 29 is similar to that of FIG. 28, but adds upper and lower stems 291 and 292 for insertion and fixation in corresponding holes in the bones defining the joint.

Figure 30A:
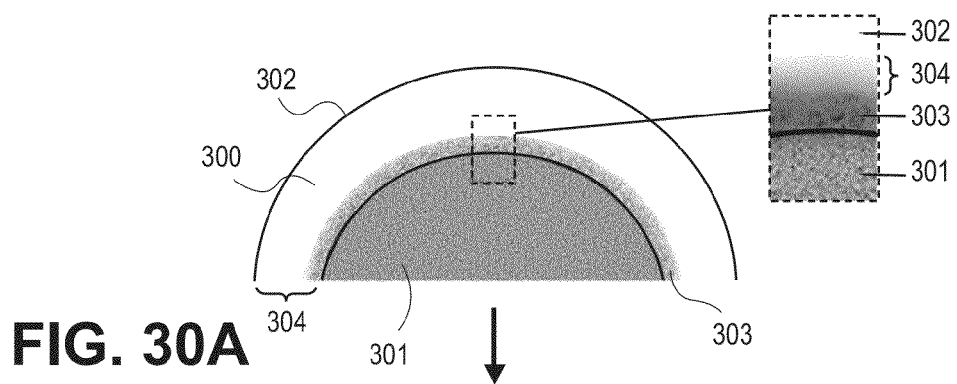
FIGS. 30A-B illustrate the integration of osteochondral grafts and other implants of this invention into bone over time.
Figure 30B:
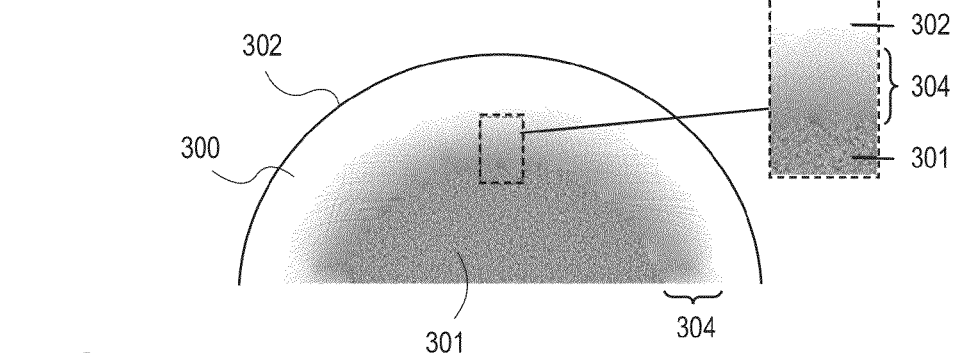

FIGS. 30A-B illustrate the integration of osteochondral grafts and other implants of this invention into bone over time. In FIG. 30A, an osteochondral graft implant 300 formed as described above is placed over bone 301. Implant 300 has a lubricious IPN or semi-IPN surface 302 and a bone interface surface 303 formed from a thermoset or thermoplastic hydrophobic polymer alone, which is optionally porous as described above. Between surface 302 and surface 303 is a gradient or transition zone 304 between the IPN or semi-IPN and the hydrophobic polymer. Over time, bone tissue will grow from bone 301 into and through the bone contacting surface 303, as illustrated in FIG. 30B.

Figure 31A:
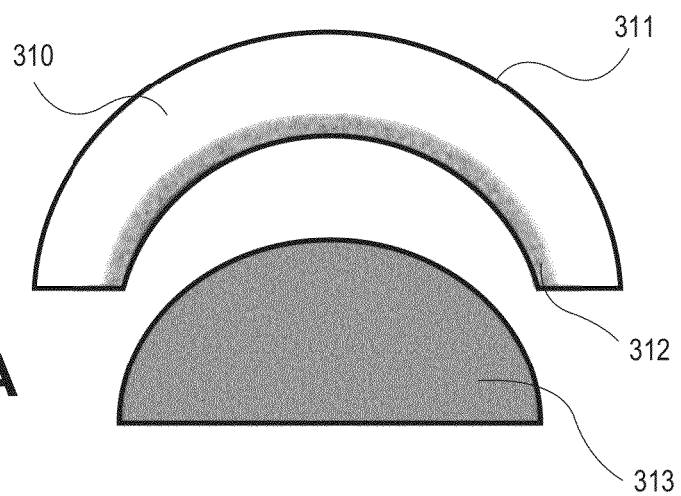
FIGS. 31A-C illustrate three possible configurations of osteochondral implants to repair cartilaginous joint surface according to this invention.
Figure 31B:
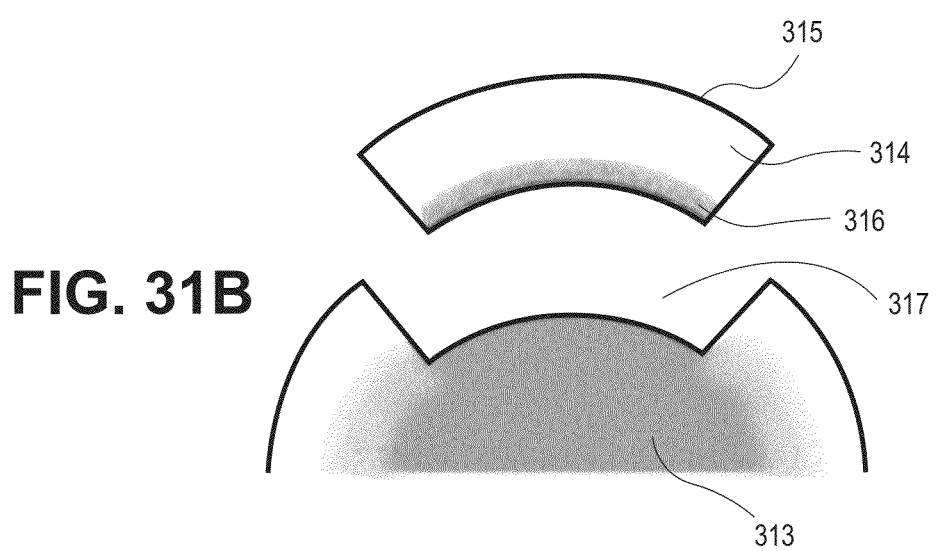
Figure 31C:
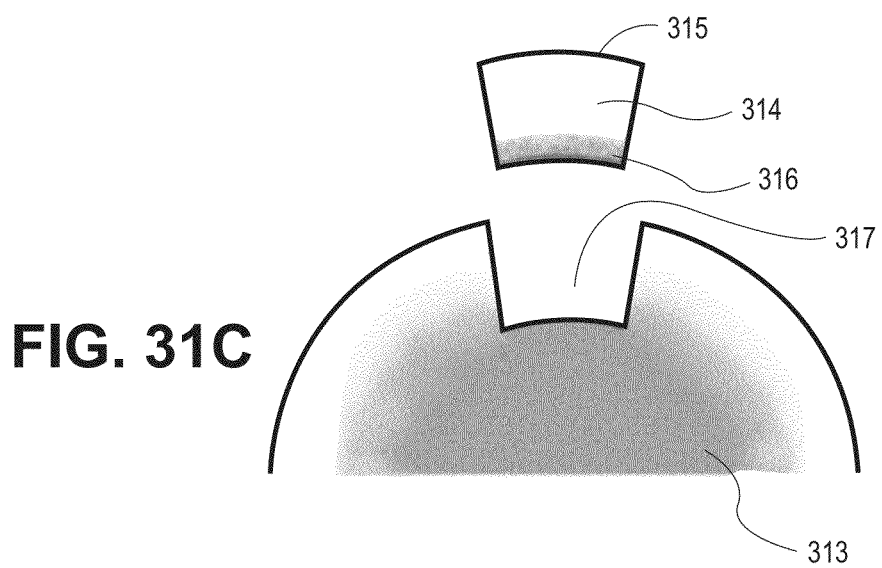

FIGS. 31A-C illustrate three possible configurations of osteochondral implants to repair cartilaginous joint surface according to this invention. In FIG. 31A, implant 310 is formed as a cap having a lubricious IPN or semi-IPN surface 311 transitioning to a bone-contacting surface 312 formed from a thermoset or thermoplastic hydrophobic polymer, as described above. When implanted, implant 310 covers the outer surface of bone 313.

FIGS. 31B and 31C show configurations in which implant 314 is formed as a patch or plug (respectively) having a lubricious IPN or semi-IPN surface 315 transitioning to a bone-contacting surface 316 formed from a thermoset or thermoplastic hydrophobic polymer, as described above. When implanted, implant 314 fits within a prepared opening 317 of bone 313.

The invention has non-medical applications. For example, FIG. 32 shows the use of a lubricious IPN or semi-IPN composition of this invention to resurface the hull of a marine vessel. Panels 320 of a thermoplastic gradient IPN (as described above) have been attached to the surface of hull 322 to reduce drag and biofilm formation. Alternatively, the IPN material can be in some embodiments painted on the hulls as a liquid and allowed to cure or harden. The gradient IPN can be negatively charged on its surface or uncharged and can be made from one or more types of monomer species. Various UV protection and anti-oxidizing agents or other additives can also be incorporated into these materials to improve their performance.

FIG. 33 shows the use of a lubricious thermoplastic or thermoset IPN (as described above) to modify interfacing surfaces of machine parts that move with respect to each other, such as surface 331 of rotating and translating part 330 and surface 333 of stationary part 332. FIG. 34 shows the use of a lubricious thermoplastic or thermoset IPN (as described above) to reduce fluid drag on the inner surface 340 of a pipe 342.

The materials of the present invention have utility in applications requiring electrochemical conductivity. The conductivity of the IPNs and semi-IPNs is based on the flow of ions through the hydrated matrix of the material. Thin films of polyetherurethane were swelled with four different compositions of an acrylic acid and water mixture (15, 30, 50, and 70% acrylic acid in water). Each swelled film was then cured in UV light to form the semi-IPN. The films were then neutralized in PBS. The electrical resistance of the materials was measured using an ohm meter. To measure resistance, the IPN film was lightly patted with a paper towel to remove excess PBS and the ohm meter probes were clipped to the film across a film width of 60-70 mm. The initial and steady-state resistance values were recorded. In addition, the resistances of an unmodified polyetherurethane film and liquid PBS were measured. The resistance of PBS was measured by placing the ohm meter probes directly into a PBS bath at an approximate distance of 60 mm between the probes. Resistance measurements are in the following Table.

TABLE 1

| Material | Lowest resistance reading (kΩ) | Steady-state resistance reading (kΩ) |
|---|---|---|
| PEU alone (0% AA) | out of range (dielectric) | out of range (dielectric) |
| PEU/PAA (15% AA) | 175 | 200 |
| PEU/PAA (30% AA) | 132 | 177 |
| PEU/PAA (50% AA) | 150 | 161 |
| PEU/PAA (70% AA) | 110 | 141 |
| PBS bath | 300 | 600 |

The results show that the resistances of the semi-IPNs are lower than (but within the same order of magnitude as) pure PBS fluid alone. The limit of the ohm meter was 40,000 ohms. Typical values for insulators (including polyurethanes) are $10^{14}$-$10^{16}$ ohms; therefore, the resistance values of the PEU alone were outside the range of the meter used. Permeability of the PEU/PAA semi-IPN was measured using a device similar to the one described by Maroudas et al. in *Permeability of articular cartilage*. Nature, 1968. 219 (5160): p. 1260-1. The permeability was calculated according to Darcy's Law ($Q=KA\Delta p/L$), where Q is the flow rate [mm$^3$/sec], A the cross-sectional area of the plug [mm$^2$], $\Delta p$ the pressure gradient applied [MPa] (pressurized fluid), L is the thickness of the hydrogel. The permeability of the PEU/PAA semi-IPN prepared from 70% acrylic acid was found to be $K=1.45\times 10^{-17}$ m$^4$/N*sec. For natural cartilage, literature values range from $1.5\times10^{-16}$ to $2\times10^{-15}$ m$^4$/N*sec. Therefore, the PEU/PAA is 10-100 times less permeable than cartilage, which may make it less prone to dehydration under prolonged compressive loads compared to natural cartilage. The permeability of the IPN can be tuned by varying the concentration of AA in the swelling solution; the higher the AA content, the higher the permeability. In contrast, the unmodified PEU material alone is effectively impermeable to solutes; although it retains some moisture (~1%), in practice it does not act as a solute-permeable matrix.

Other variations and modifications to the above compositions, articles and methods include:

The first polymer can be one that is available commercially or custom-made and made by a number of ways (e.g., extruded, injection molded, compression molded, reaction injection molded (RIM) or solution-casted.) The first polymer can be uncrosslinked or crosslinked by various means. Either polymer can be crosslinked by, e.g., gamma radiation or electron beam radiation.

Any number or combinations of ethylenically unsaturated monomers with ionizable groups or macromonomers (e.g., containing reactive double bonds) can be used as the basis of the second or subsequent network so long as the total contains at least 2% by weight ionizable chemical groups. These include but are not limited those containing vinyl, acrylate, methacrylate, allyl ether, or acrylamide groups. Any number of pendant functional groups can be conjugated to these ethylenically unsaturated groups including but not limited to carboxylic acid, sulfonic acid, acetates, alcohols, ethers, phenols, aromatic groups, or carbon chains.

The polyurethane-based polymer can be (but is not limited to) the following: polyether urethane, polycarbonate urethane, polyurethane urea, silicone polyether urethane, or silicone polycarbonate urethane. Other polyurethanes with other hard segments, soft segments, and chain extenders are possible.

Other polymers can be used in the first network, such as homopolymers or copolymers of silicone (polydimethylsiloxane) or polyethylene.

When a polyurethane-based polymer is used as the first polymer, the extent of physical and chemical crosslinking of the polyurethane-based polymer can be varied between physical crosslinking-only (thermoplastic) to extensive chemical crosslinking. In the case of chemical crosslinking, the crosslinkable polyurethane can be used alone or as a mixture with thermoplastic (uncrosslinked) polyurethane.

The conditions of polymerization (i.e., ambient oxygen, UV intensity, UV wavelength, exposure time, temperature) may be varied.

The orientation and steepness of the composition gradients can be varied by various means such as time and/or method of immersion in the monomer, and the application of external hydrostatic positive or negative pressure.

The thermoplastic can be made porous by various techniques such as foaming or salt-leaching. After swelling of the porous polymer (such as PU) with a monomer (such as AA) followed by polymerization or AA, a porous IPN is formed.

Additional layers of thermoplastics can be added to material on either the IPN side or the thermoplastic side-only by curing or drying the new thermoplastic to the surface. The layers can all be the same material or be different materials (e.g. ABS+polyurethane, polyether urethane+polycarbonate urethane, etc.

A number of different solvents can be used during the synthesis of the polyurethane, the second network, or both, including but not limited to dimethylacetamide, tetrahydrofuran, dimethylformamide, ethanol, methanol, acetone, water, dichloromethane, propanol, methanol, or combinations thereof.

Any number of initiators can be used such as photoinitiators (e.g., phenone-containing compounds and Irgacure® products), thermal initiators, or chemical initiators. Examples of thermal initiators include but are not limited to azo-compounds, peroxides (e.g., benzoyl peroxide), persulfates (e.g., potassium persulfate or ammonium persulfate), derivatives, or combinations thereof.

Variations of the crosslinking identity and density (e.g. 0.0001%-25% by mole crosslinking agent with respect to the monomer), initiator concentration (e.g. 0.0001%-10% by mole with respect to the monomer) molecular weight of precursor polymers, relative weight percent of polymers, light wavelength (UV to visible range), light intensity (0.01 mW/cm$^2$-1 W/cm$^2$), temperature, pH and ionic strength of swelling liquid, and the level of hydration.

The second network material can be synthesized in the absence of a crosslinking agent.

The water content of these materials can range between 2% to 99%.

Different components of the IPN can be incorporated in combination with ionizable monomers, such as poly(vinyl alcohol), poly(ethylene glycol)-acrylate, poly(2-hydroxyethylacrylate), poly(2-hydroxyethylmethacrylate), poly (methacrylic acid), poly(2-acrylamido-2-methyl propane sulfonic acid), other vinyl-group containing sulfonic acids, poly (acrylamide), poly(N-isopropylacrylamide) poly (dimethacrylamide), and combinations or derivatives thereof. For instance, a copolymer of acrylic acid and vinyl sulfonic acid or 2-acrylamido-2-methyl propane sulfonic acid can be created for the second network to form a polyurethane first network and a poly(acrylic acid-co-acrylamido-methyl-propane sulfonic acid) copolymeric second network. Any monomer or combination of monomers can be used in conjunction with a suitable solvent as long as they contain at least 2% by weight ionizable monomer and are able to enter (swell) the first polymer.

The IPN can have incorporated either chemically or physically within its bulk or its surface certain additives such as antioxidants (e.g., Vitamin C, Vitamin E, Irganox®, or santowhite powder) and/or anti-microbial agents (e.g., antibiotics). These can be chemically linked to the material by, for example, esterification of the anti-oxidant with any vinyl-group containing monomer such as methacrylate, acrylate, acrylamide, vinyl, or allyl ether.

More than two networks (e.g., three or more) can also be formed, each of which are either crosslinked or uncrosslinked.

The polyurethane itself can be modified in a number of ways, such as by sulfonation at the urethane group by reaction of 1,3 propane sulfone in the presence of sodium hydride, or the formation of allophanate linkages at the urethane group by reaction with excess isocyanate groups. For instance, excess isocyanatoethyl methacrylate can be reacted with polyurethane in toluene in the presence of dibutyltin dilaurate for 2.5 hours to yield a methacryloxy-conjugated polyurethane surface. The methacryloxy groups can then be used subsequently tether other methacryloxy (or other vinyl group)-containing monomers or macromonomers via free radical polymerization. Such modifications can be carried out before or after the formation of the second network of the IPN. Other modifications will be apparent to those skilled in the art.

EXAMPLES

Example 1

In one example, a polycarbonate urethane (Bionate 55D) was immersed in 70% acrylic acid in water containing 0.1% v/v 2-hydroxy-2-methyl propiophenone and 0.1% v/v triethylene glycol dimethacrylate with respect to the monomer overnight. The polycarbonate urethane was removed from the solution, placed between two glass slides, and exposed to UV light (2 mW/cm$^2$) for 15 minutes. The resulting semi-IPN was removed, and washed and swollen in phosphate buffered saline. The material swelled and became lubricious within hours. In other examples, segmented polyurethane urea, as well as silicone polyether urethane and silicone polycarbonate urethanes were placed in acrylic acid solutions and polymerized and washed in the same fashion to yield a lubricious IPN.

Example 2

In another example, a polyether urethane (Elasthane™ 55D) was immersed in 70% acrylic acid in water containing 0.1% v/v 2-hydroxy-2-methyl propiophenone and 0.1% v/v triethylene glycol dimethacrylate with respect to the monomer overnight. The polyether urethane was removed from the solution, placed between two glass slides, and then exposed to UV light (2 mW/cm$^2$) for 15 minutes. The resulting semi-IPN was removed and then washed and swollen in phosphate buffered saline. The material swelled and became lubricious within hours. In other examples, polycarbonate urethane, segmented polyurethane urea, as well as silicone polyether urethane and silicone polycarbonate urethanes were placed in acrylic acid solutions and polymerized and washed in the same fashion to yield lubricious IPNs.

Example 3

In another example, silicone polyether urethane and silicone polycarbonate urethanes were separately placed overnight in 100% acrylic acid solutions, to which were added 0.1% v/v 2-hydroxy-2-methyl propiophenone and 0.1% v/v triethylene glycol dimethacrylate with respect to the monomer. After polymerization and crosslinking, the semi-IPNs swelled and became lubricious. The addition of silicone (polydimethylsiloxane) in the polyurethane adds an extra level of biostability to the material as well as potentially useful surface chemistry and properties.

Example 4

In another example, a methacryloxy-functionalized polycarbonate urethane was exposed to UV light to crosslink the polycarbonate urethane, and then swollen in 70% acrylic acid with 0.1% v/v 2-hydroxy-2-methyl propiophenone and 0.1% v/v triethylene glycol dimethacrylate with respect to the monomer overnight. The material was removed from the solution, placed between two glass slides, and then exposed to UV light (2 mW/cm$^2$) for 15 minutes to yield a fully interpenetrating polymer network of the polycarbonate urethane and poly(acrylic acid.) The IPN was then washed in an aqueous salt solution to neutralize the poly(acrylic acid), achieve equilibrium swelling, and remove any unreacted monomers.

Example 5

In another example, a methacryloxy-functionalized polyether urethane was exposed to UV light (in the presence of 0.1% 2-hydroxy-2-methyl propiophenone and 0.1% triethylene glycol dimethacrylate) to crosslink the polyetherurethane, and then was swollen in 70% acrylic acid with the aforementioned photoinitiator and crosslinker followed by UV-initiated crosslinking to yield a fully interpenetrating polymer network of the polyetherurethane and poly(acrylic acid.) The IPN was then washed in an aqueous salt solution to neutralize the poly(acrylic acid), achieve equilibrium swelling, and remove any unreacted monomers.

Example 6

In another example, a 25% solution of methacryloxy-functionalized polycarbonate urethane in DMAC along with 0.1% of the aforementioned photoinitiator was exposed to UV light to crosslink the polycarbonate urethane. After removing the solvent in a heated (60° C.) convection oven, an additional layer of polycarbonate urethane was then cast on one side of the crosslinked polycarbonate urethane to yield a laminate structure and then only the crosslinked side was swollen in 70% acrylic acid with the 0.1% 2-hydroxy-2-methyl propiophenone and 0.1% triethylene glycol dimethacrylate followed by UV-initiated crosslinking to yield a fully interpenetrating polymer network of the polycarbonate urethane and poly(acrylic acid.) The IPN was then washed in an aqueous salt solution to neutralize the poly(acrylic acid), achieve equilibrium swelling, and remove any unreacted monomers.

Example 7

In another example, a 25% solution of methacryloxy-functionalized polycarbonate urethane in DMAC along with 0.1% of the aforementioned photoinitiator was exposed to UV light to crosslink the polyether urethane. After removing the solvent in a heated (60° C.) convection oven, an additional layer of polyether urethane was then cast on one side of the crosslinked polycarbonate urethane to yield a laminate structure and then only the crosslinked side was swollen in 70% acrylic acid with 0.1% 2-hydroxy-2-methyl propiophenone and 0.1% triethylene glycol dimethacrylate followed by UV-initiated crosslinking to yield a fully interpenetrating polymer network of the polyether urethane and poly(acrylic acid.) The IPN was then washed in an aqueous salt solution to neutralize the poly(acrylic acid), achieve equilibrium swelling, and remove any unreacted monomers.

Example 8

In another set of examples, a layer of methacroxy-functionalized polyether urethane was cast onto a layer of injection molded polyether urethane, and separately, another layer was cast onto a layer of injection molded polycarbonate urethane. Each was exposed to UV light, to yield laminate structures. Only the crosslinked sides were swollen in 70% acrylic acid with 0.1% 2-hydroxy-2-methyl propiophenone and 0.1% triethylene glycol dimethacrylate followed by UV-initiated crosslinking to yield a fully interpenetrating polymer networks. The IPNs were then washed in an aqueous salt solution to neutralize the poly(acrylic acid), achieve equilibrium swelling, and remove any unreacted monomers.

Example 9

In one example, acrylonitrile butadiene styrene (ABS) was exposed to 100% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by dropcasting the monomer solution on the surface of the ABS for 30 minutes. The ABS was then placed between two glass slides, and then exposed to UV light (2 mW/cm$^2$) for 15 minutes. The resulting ABS/PAA gradient IPN was removed and then washed and swollen in phosphate buffered saline. The IPN was washed in an aqueous salt solution to neutralize the poly(acrylic acid), achieve equilibrium swelling, and remove any unreacted monomers. The material swelled and became lubricious within hours.

Example 10

To reshape the thermoplastic gradient IPNs, heat was applied. An ABS/PAA gradient IPN was heated using a heat gun and then laid on a cylindrical polypropylene tube. After letting the material cool to room temperature, acetone was injected between the ABS/PAA and the polypropylene. After applying manual pressure and allowing the sample to dry, the result was a thermoplastic gradient IPN wrapped around and bonded to a polypropylene tube.

Example 11

In another example, a thermoplastic gradient ABS/PAA IPN was attached to polycarbonate urethane by injecting acetone between the ABS and polycarbonateurethane and applying manual pressure to yield a thermoplastic gradient IPN bonded to a polycarbourethane.

Example 12

In another example, a curved polycarbonate urethane IPN was made straight again by applying heat on the polyurethane side using a heat gun, manually reversing the curvature of the material, and cooling the IPN in water.

Example 13

In another example, a polyether urethane solution (e.g. 20% in dimethylacetamide ("DMAC")) was cast on top of a polycarbonate urethane in a laminate structure, allowed to dry in a heated (60° C.) convection oven, and then only the polyether urethane surface was exposed to 70% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by laying the laminate material polyether urethane-side down on a bed of fabric that was soaked in the aforementioned monomer solution. The material was removed from the fabric mat, placed between two glass slides, and then exposed to UV light (2 mW/cm$^2$) for 15 minutes. The resulting gradient semi-IPN was removed, washed and swollen in phosphate buffered saline. The material swelled and became lubricious within hours. In other examples, polyether urethane, segmented polyurethane urea, silicone polyether urethane, and silicone polycarbonate urethane were handled the same way to yield a lubricious semi-IPNs.

Example 14

In another example, a layer of polycarbonate urethane (20% in DMAC) containing 50% by weight sodium chloride was solution cast on a premade polyether urethane-polycarbonate urethane and dried at 80° C. under convection. The salt was washed away in water to yield a porous side on the laminated polyurethane. Other materials have been made with sodium chloride concentrations varying between 10% and 80%

Example 15

In another example, a layer of polycarbonate urethane (20% in DMAC) containing 20% tricalcium phosphate was solution cast on a premade polyether urethane-polycarbonate urethane and dried at 80° C. under convection. The tricalcium phosphate was left embedded within the polyurethane as an osteoconductive agent. Other materials have been made with tricalcium phosphate concentrations varying from 0.001%-20%

Example 16

In another example, a polyurethane urea (e.g. 20% in dimethylacetamide) was cast on top of a polycarbonate urethane in a laminate structure, and then only the polyurethane urea surface was exposed to 70% acrylic acid in water containing 0.1% v/v 2-hydroxy-2-methyl propiophenone and 0.1% v/v triethylene glycol dimethacrylate with respect to the monomer for 15 minutes. The surface-exposure was accomplished by laying the laminate material polyurethane urea-side down on a bed of fabric that was soaked in the aforementioned monomer solution. The polycarbonate urethane was removed from the fabric mat, placed between two glass slides, and then exposed to UV light (2 mW/cm$^2$) for 15 minutes. The resulting gradient semi-IPN was removed and then washed and swollen in phosphate buffered saline. The material swelled and became lubricious within hours. The material was washed in PBS to neutralize the poly(acrylic acid), achieve equilibrium swelling, and remove any unreacted monomers.

Example 17

In another example, a methacryloxy-functionalized polyether urethane mixed with a thermoplastic polyether urethane in solution (25% in dimethylacetamide) was exposed to UV light to crosslink the polycarbonate urethane. An additional layer of polyether urethane was then cast on one side of the crosslinked polyether urethane to yield a laminate structure and then only the crosslinked side was swollen in 70% acrylic acid with the aforementioned photoinitiator and crosslinker, followed by UV-initiated crosslinking to yield a fully interpenetrating polymer network of the polyether urethane and poly(acrylic acid.) The IPN was then washed in an aqueous salt solution to neutralize the poly(acrylic acid), achieve equilibrium swelling, and remove any unreacted monomers.

Example 18

In one example, flat sheets were created by solution casting of thermoplastic polyurethanes in (dimethylacetamide (DMAC). Polyurethane solutions of polyether urethane (Elasthane™), polycarbonate urethane (Bionate), polyether urethane urea (Biospan), silicone polycarbonate urethane (Carbosil), and silicone polyether urethane (Pursil) were synthesized in dimethylacetamide (DMAC) at solids concentrations of about 25% by the manufacturer.

Example 19

Spherical shapes were cast by dip-coating glass as well as silicone spheres in polyurethane solutions (in DMAC). Polycarbonate urethane (20% in DMAC) was dip coated onto a spherical glass mold (49.5 mm outer diameter), and separately, onto a silicone sphere. The solvent was removed by drying at 80° C. in a convection oven. This process was repeated two more times to create three total coatings. Then, the sphere was dip coated in polyether urethane (20% in DMAC) and then dried at 80° C. under convection. This process was also repeated two more times. The resulting capped-shaped, laminate polyurethane was removed from the mold, and its outer side immersed in a 70% acrylic acid solution in water, with 0.1% 2-hydroxy-2-methyl-propiophenone and 0.1% triethylene glycol dimethacrylate for 1.5 hours. The cap was inverted, placed back over a spherical glass mold, and exposed to UV light (2 mW/cm$^2$) for 15 minutes. Next the cap was removed from the mold and placed in phosphate buffered saline. The result was a spherical, gradient IPN with one lubricious surface and one pure thermoplastic surface. Other temperatures and other solvents can also be used to carry out this process, as well as other mold materials and polymer components.

Example 20

In another example, a polyether urethane was swollen in 70% acrylic acid with 0.1% 2-hydroxy-2-methyl propiophenone and 0.1% methylene bisacrylamide. One side of the material was dabbed dry, and then exposed to air and treated with UV light. The resulting gradient semi-IPN was then washed in an aqueous salt solution to neutralize the poly (acrylic acid), achieve equilibrium swelling, and remove any unreacted monomers. In other experiments, the material was exposed to nitrogen or argon during curing.

Example 21

In another example, a polyether urethane (Elasthane™ 55D) was injection molded and then swollen in 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 22

In another example, a polyether urethane (Elasthane™ 75D) was injection molded, dip-casted (solution casted) on one side in a polyether urethane solution (Elasthane™ 55D in 25% DMAC) and dried in a convection oven to remove the DMAC solvent. The dried material was swollen in 70% acrylic acid with the 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 23

In another example, a polycarbonate urethane (Bionate 75D) was injection molded, dip-casted (solution casted) on one side in a polyether urethane solution (Elasthane™ 55D in 25% DMAC) and dried in a convection oven to remove the DMAC solvent. The dried material was swollen in 70% acrylic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 24

In another example, a polyether urethane (Elasthane™ 75D) was injection molded and then dip-casted (solution casted) in a methacryloxy-functionalized polyether urethane solution (Elasthane™ 55D in 25% DMAC) along with the aforementioned photoinitiator and then was exposed to UV light to crosslink the methacryloxy-functionalized polyether urethane. The material was then dried in a convection oven to remove the DMAC solvent. The dried material was then swollen in 70% acrylic acid with the 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 25

In another example, a polycarbonate urethane (Bionate 75D) was injection molded and then dip-casted (solution casted) in a methacryloxy-functionalized polyether urethane solution (Elasthane™ 55D in 25% DMAC) and then was exposed to UV light to crosslink the methacryloxy-functionalized polyether urethane. The material was then dried in a convection oven to remove the DMAC solvent. The dried material was then swollen in 70% acrylic acid with the 0.1% v/v 2-hydroxy-2-methyl propiophenone and 0.1% v/v triethylene glycol dimethacrylate followed by UV-initiated crosslinking to yield a fully interpenetrating polymer network of the polyether urethane and poly(acrylic acid). The IPN was then washed in an aqueous salt solution to neutralize the poly(acrylic acid), achieve equilibrium swelling, and remove any unreacted monomers.

Example 26

In another example, a polyether urethane (Elasthane™ 55D) solution casted and then swollen in 35% sulfopropyl methacrylate in acetic acid with 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The semi-IPN was then washed with water to remove the acetic acid, and then in an aqueous salt solution to neutralize the poly(acrylic acid), achieve equilibrium swelling, and remove any unreacted monomers.

Example 27

In another example, a polyether urethane (Elasthane™ 55D) solution casted and then swollen in 35% sulfopropyl methacrylate and 35% acrylic acid in water with the 0.1% v/v 2-hydroxy-2-methyl propiophenone and 0.1% w/w methylene bisacrylamide followed by UV-initiated crosslinking to yield a fully interpenetrating polymer network of the polyether urethane and poly(acrylic acid). The semi-IPN was then washed in an aqueous salt solution to neutralize the poly (acrylic acid)/poly(sulfopropyl methacrylate) copolymer, achieve equilibrium swelling, and remove any unreacted monomers.

Example 28

In another example, a rectangular sample of PMMA (plexiglass) was swollen briefly in 100% acrylic acid in water with the 0.1% v/v 2-hydroxy-2-methyl propiophenone and 0.1% w/w methylene bisacrylamide followed by UV-initiated crosslinking to yield a fully interpenetrating polymer network of the PMMA and poly(acrylic acid). The IPN was then washed in an aqueous salt solution to neutralize the poly (acrylic acid), achieve equilibrium swelling, and remove any unreacted monomers.

Example 29

In another example, a rectangular specimen of polydimethyl sulfoxide (PDMS, Sylgard® 184) was prepared according to the manufacturer's specifications and then was swollen briefly in a 35% acrylic acid solution in tetrahydrofuran along with 0.1% v/v 2-hydroxy-2-methyl propiophenone and 0.1% v/v triethylene glycol dimethacrylate, followed by UV-initiated crosslinking to yield a fully interpenetrating polymer network of the PDMS and poly(acrylic acid). The IPN was washed in an aqueous salt solution to neutralize the poly (acrylic acid), achieve equilibrium swelling, and remove any unreacted monomers.

Example 30

Figure 35:
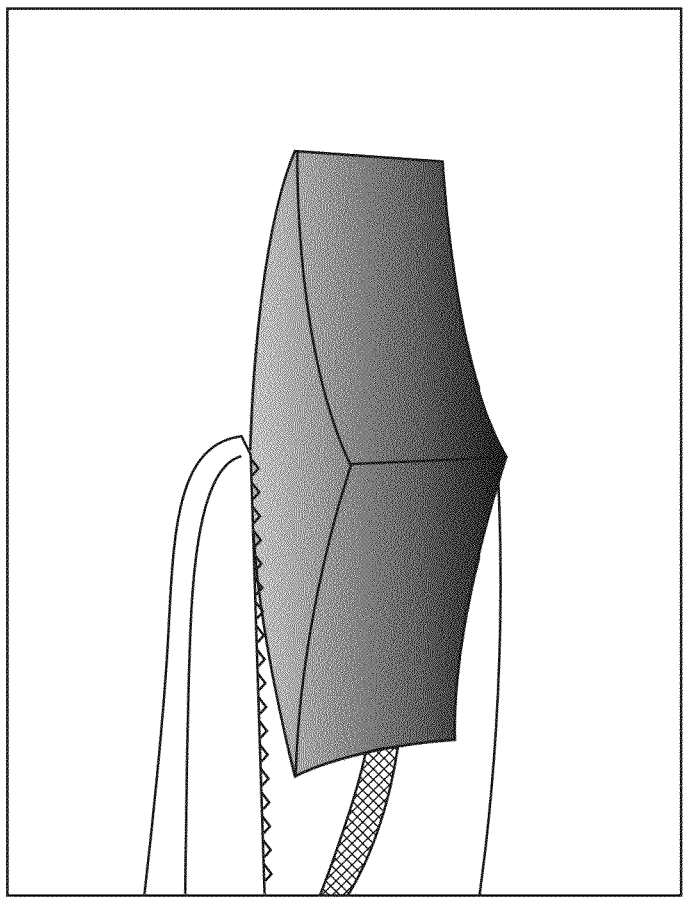
FIG. 35 is a photograph of a hydrated PEU/PAA semi-IPN gradient material being held by a forceps.

FIG. 35 is a cross-section of a hydrated arthroplasty device and shows that the arthroplasty device is, in effect, a synthetic version of an osteochondral graft that emulates the structure, elastic modulus, fracture strength, and lubricious surface of natural cartilage on one side and the stiffness, strength, and porosity of trabecular bone on the other side. The device is comprised of a composite gradient material featuring a lubricious, cartilage-like polymer that smoothly transitions into a stiff, porous, bone-like anchoring surface. The gradient was designed to mimic the compositional gradient inherent to natural joints, in which compliant, slippery cartilage becomes progressively more hard and bone-like from superficial to deep along the thickness direction. In practice, this "biomimetic" gradient should yield a physiologic stress distribution over the underlying bone while also minimizing micromotion at the bone interface by effectively matching the stiffnesses of the device and bone at their point of contact. Suitable materials are described, e.g., in the following, the disclosures of which are incorporated herein by reference: U.S. Patent Appl. Ser. No. 61/079,060 (filed Jul. 8, 2008); U.S. Patent Appl. Ser. No. 61/095,273 (filed Sep. 8, 2008); and U.S. patent application Ser. No. 12/148,534 (filed Apr. 17, 2008).

Example 31

Figure 36:
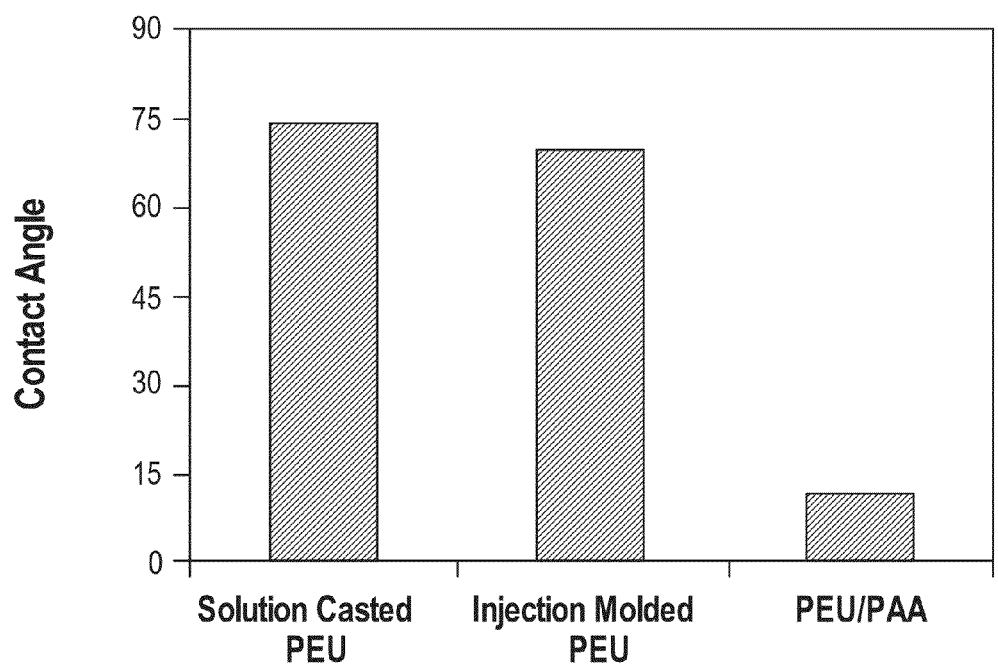
FIG. 36 shows contact angle analysis in association with Example 32.

FIG. 36 shows contact angle analysis indicating that the material of this invention is very hydrophilic. When a drop of water is placed on a surface, the shape the drop takes is dependent on the composition of the surface. A hydrophilic surface attracts the water and creates a flatter drop, while a hydrophobic surface repels the water and creates a rounder drop. The degree of hydrophilicity of the surface is inferred by measuring the angle created between the surface and the drop of water, referred to as the contact angle. Typically, a more hydrophilic surface will have a contact angle of about 0-45° with water, while a more hydrophobic surface will have a contact angle greater than 45° with water.

The contact angle between the charged hydrogel IPN made by this invention and water was determined. Briefly, a sheet of Elasthane™ 55D (polyetherurethane) was soaked in acrylic acid with initiator and cross-linker, and cured to form a semi-IPN (PEU/PAA semi IPN). After curing, the charged PEU/PAA semi IPN was hydrated in phosphate buffered saline. The material was removed from the solution and its surface briefly dabbed to remove any residual liquid. A drop of water was placed on the surface of the material, and the contact angle read using a Goniometer. The results showed a contact angle of approximately 8°. For comparison, readings taken on starting materials of solution-casted polyurethanes and injection-molded polyurethane had contact angles of approximately 72° and 69°, respectively. This result demonstrates that the incorporation of a poly(acrylic acid) network into polyurethane according to the current invention dramatically increases surface hydrophilicity.

Example 32

The differences in the structures of the charged hydrogel IPN and polyurethane are shown by Transmission Electron Microscopy (TEM). TEM creates a highly magnified image of a material. TEM was performed on samples of polyetherurethane/poly(acrylic) acid semi IPN (PEU/PAA semi IPN) of the current invention and of unmodified polyetherurethane. Briefly, a sheet of Elasthane™ 55D (polyetherurethane) was soaked in acrylic acid with initiator and cross-linker, and cured. It was stained with osmium tetroxide per standard procedures to perform TEM analysis. FIG. 37A shows a 34 k× magnification image of PEU while FIG. 37 B shows the PEU/PAA semi-IPN. The sizes of light and dark regions, corresponding to the amorphous (soft) and ordered (hard) domains, are increased in the TEM images of the PEU/PAA semi-IPN relative to the unmodified PEU. The PAA appears sequestered within the PEU soft segments. on the basis of the larger domain sizes in the PEU/PAA sample compared to the PEU sample, the degree of phase separation is greater in the PEU/PAA sample compared to the unmodified PEU.

Example 33

Figure 37B:
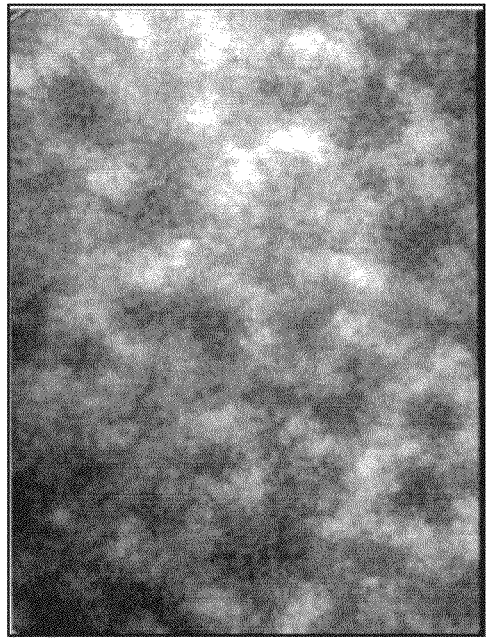
FIGS. 37A-B show the PEU/PAA semi-IPN material subject to Transmission Electron Microscopy analysis as associated with Example 33.
Figure 37A:
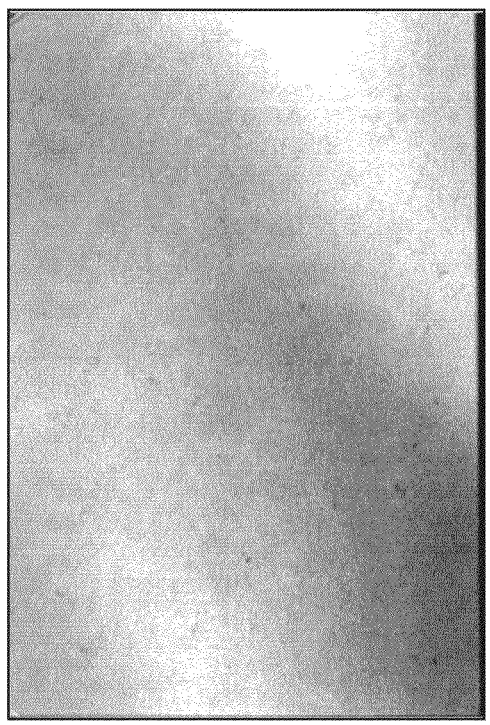

FIG. 38 shows a TEM of the same PEU/PAA semi-IPN material as FIG. 37 at 12.4 k× magnification. The schematic illustrates how the hard segments are phase separated from the soft segments of the interpenetrated polymer network.

Example 34

Figure 39:
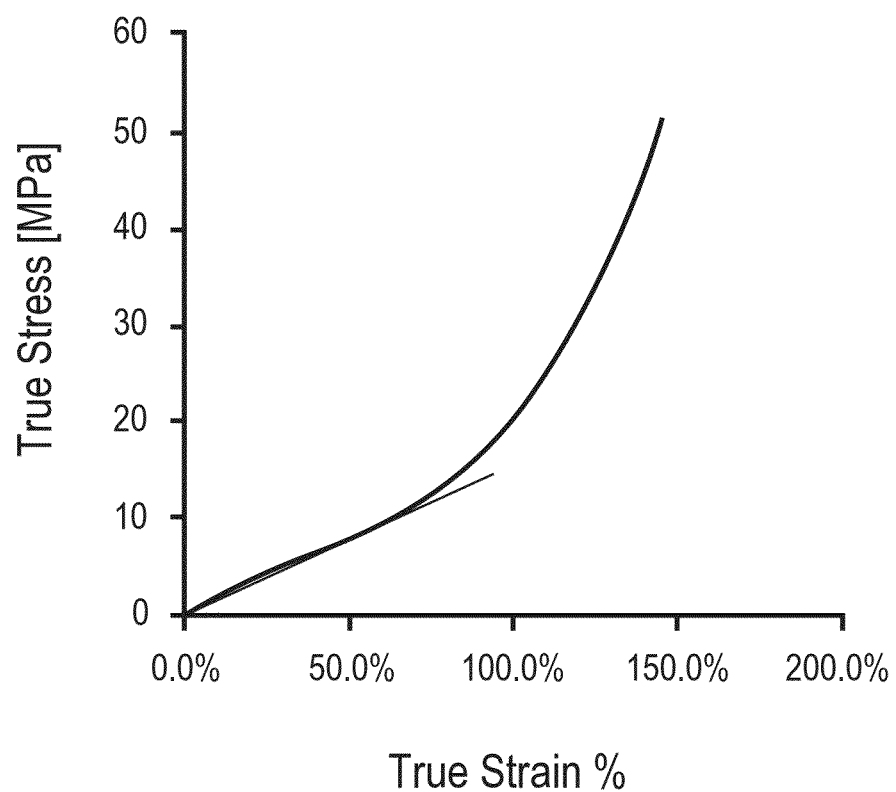
FIG. 39 shows the tensile stress-strain behavior of the PEU/PAA semi-IPN material associated with Example 35.

FIG. 39 shows the static mechanical properties of the PEU/PAA IPN which comprises an exemplary joint interface surface of an orthopaedic implant. Uniaxial tensile tests were conducted to determine the initial Young's modulus in tension, the strain-at-break, and stress-at-break of the materials. Dog bone specimens were tested according to ASTM D638, at a strain rate of 0.3%/sec. The average true stress—true strain curve for the material of the joint interface material is presented in FIG. 40. In the linear portion of the curve, the elastic modulus (as provided from the true stress, true strain curve) is E=15.3 MPa which is very close to the tensile properties reported for natural cartilage. The ultimate true stress was found to be at approximately $\sigma_{ult}$=52 MPa at $\epsilon_{ult}$=143% true strain (of note, cartilage is found to fail at around 65% strain). Strain hardening under tension was observed for true strains of 80% and higher. The Poisson's ratio (equilibrium) was estimated by measuring the lateral contraction of the dog bone neck region and was found to be consistent along the strain range at v=0.32. The bulk modulus was therefore calculated from the equation K=E/3(1−2v) and was found to be 18.3 MPa. Unconfined compression plug tests according to ASTM D695 reveal that PEU/PAA semi-IPN has excellent compressive properties, with a compressive stiffness modulus of 15.6 MPa (same as the tensile modulus, based on true stress-strain) and a failure strength that is higher than 50 MPa.

Example 35

Figure 40:
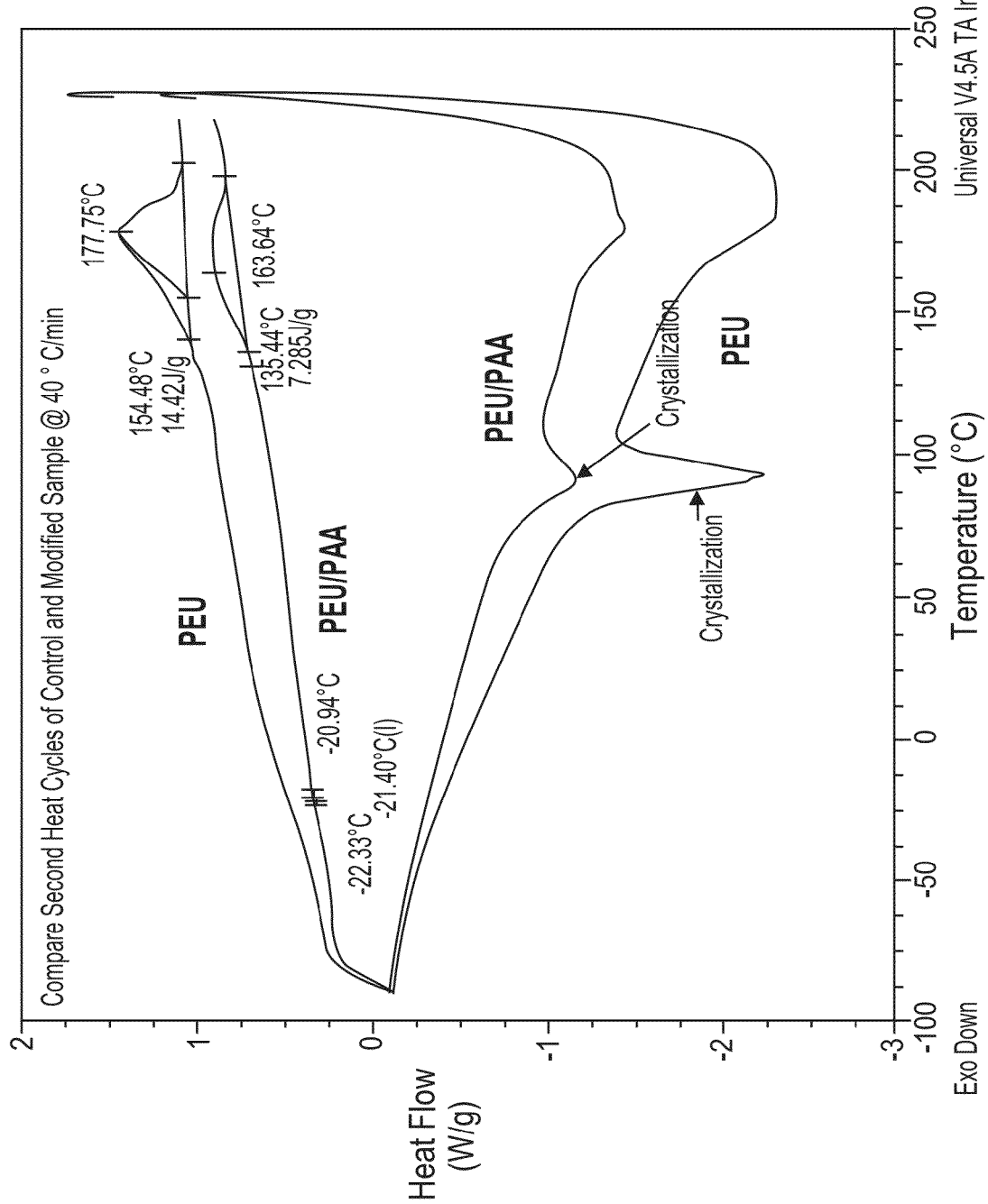
FIG. 40 shows the thermagram of the PEU/PAA semi-IPN material analyzed by DSC associated with Example 36.

FIG. 40 shows the thermal curves of PEU and PEU/PAA semi-IPN samples evaluated by Differential Scanning calorimetry (DSC) at a heating rate of 40° C. per minute. FIG. 41 compares the thermal transitions of PEU and PEU/PAA semi-IPN samples evaluated by DSC at two different heating rates. The thermal transition temperatures including the glass transition temperature $T_g$, the crystallization temperature, and the melting temperature Tm were determined. Below its $T_g$, the heat capacity of the polymer is lower and the polymer is harder or glassier. Above the $T_g$, the heat capacity of the polymer increases and the polymer becomes more flexible. Above this temperature, for some polymers is the crystallization temperature and at least some of the domains of the molecule become more organized, and essentially crystalline. At a higher temperature is the melting temperature when the crystalline portions completely melt. The procedure was done following ASTM D3418-03 test method using a TA Instruments Q200 DSC system with a Modulated Differential Scanning calorimeter and Refrigerated Cooling System (RCS90). Briefly, a sheet of Elasthane™ 55D (polyetherurethane) was soaked in acrylic acid with an initiator and cross-linker and then cured. A small amount (2-6 mg) of PEU/PAA semi-IPN sample was placed into a first aluminum pan. A cover was placed on the top of the pan and crimped with a Universal Crimping press to sandwich the sample between pan and cover. Heat was applied to the first pan and, separately, to a reference pan, and the current flow to each was changed to keep the temperatures of the two materials the same. The heat flow of the material being tested was graphed against the temperature and the slopes of the curves indicate the thermal transition temperatures (FIG. 40). Several tests were performed, using different rates of heating (10° C. and 40° C. per minute). By performing the tests at different rates of heating, different resolution is obtained for the thermal transitions, as seen in FIG. 41. Because the $T_g$ can depend on the previous thermal history of the material, the material is subjected to two heat cycles. The first heat cycle is used to standardize the conditions under which the polymer arrives at its test state, and the second test cycle is used to generate transition temperatures. The glass transition temperatures, $T_g$, for both the PEU/PAA semi IPN and the PEU were around 21° C. when the rate of heating was kept at 10° C. per minute. The crystallization and melting temperatures were lower in the PEU/PAA compared with the PEU. At a heating rate of 40° C. per minute, the crystallization temperatures were 90° C. for the PEU/PAA compared with 93° C. for the PEU. When the heating rate was slowed to 10° C. per minute, the crystallization temperatures observed were 79° C. for the PEU/PAA compared with 92° C. for the PEU. Finally, at a heating rate of 40° C. per minute, the Tm temperatures were 164° C. for the PEU/PAA compared with 178° C. for the PEU. When the heating rate was slowed to 10° C. per minute, the $T_m$ temperatures observed were 154° C. for the PEU/PAA with 176 and 186° C. for the PEU. In some analyses of the PEU, two $T_m$'s were observed (176° C. and 186° C.), which may be due to different segments in the polymer. The change of the $T_m$ is due at least in part to an increase in polymer volume caused by the addition of the PAA, leading to fewer hard segments per volume of polymer.

Example 36

Figure 42:
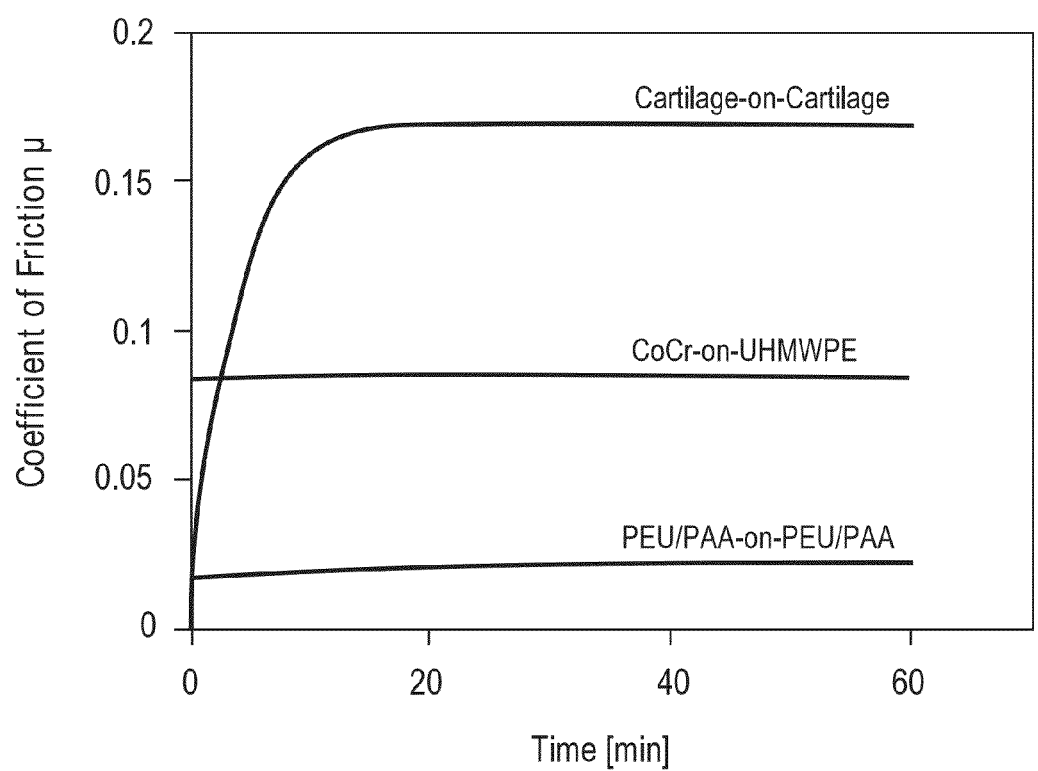
FIG. 42 shows the coefficient of friction of the PEU/PAA semi-IPN material on PEU/PAA under static load associated with Example 37.
Figure 43:
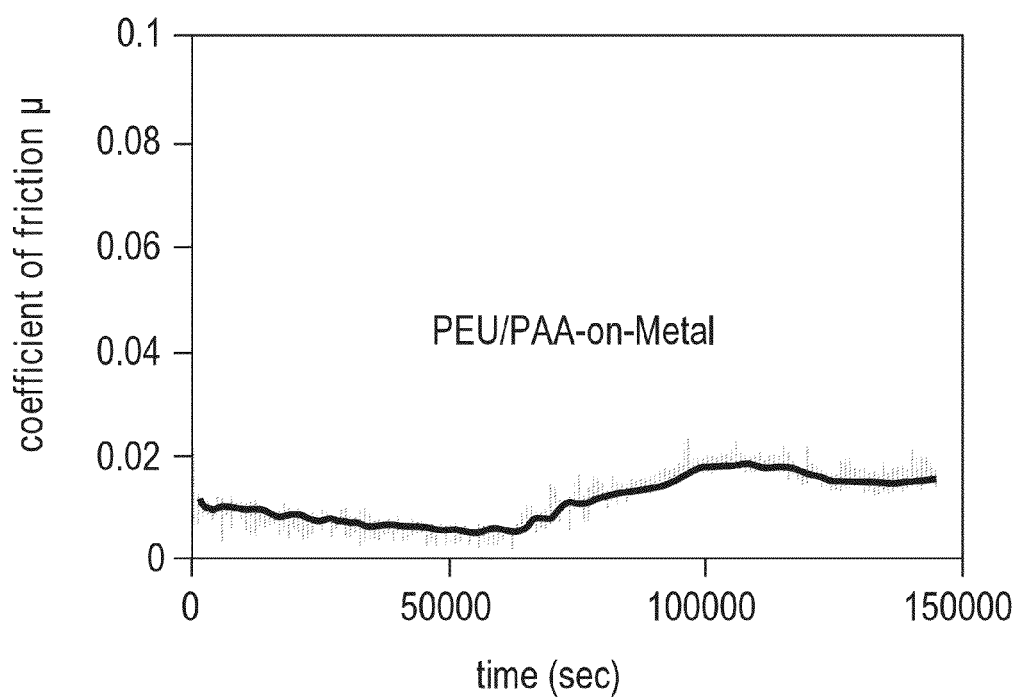
FIG. 43 shows the coefficient of friction of the PEU/PAA semi-IPN material on metal under static load associated with Example 38.

The coefficient of friction μ of a PEU/PAA semi-IPN of this invention against itself was measured real-time during a wear test using a built-in torque cell, and was found to range between 0.015 to 0.06, and as shown in FIG. 42, is similar to cartilage-on-cartilage μ values. Because of its lower (compared to cartilage) permeability, the PEU/PAA semi-IPN of this invention can preserve a lower coefficient of friction for longer and at higher contact pressures. FIG. 42 shows the effective coefficient of friction during a wear test of the joint interface material (labeled "PEU/PAA-on-PEU/PAA" in the graph) under 2.4 MPa of continuous (static) contact pressure. Literature reports on natural cartilage values and experimental data/literature reports on UHMWPE on CoCr are also presented in the plot (Mow, 2005; Wright 1982). As expected, the coefficient of friction was found to remain unchanged over the course of time when the load was applied in cycles of 1 Hz; similar results are reported for cartilage. The low coefficient of friction in the material can be explained in terms of (a) hydroplaning action, (b) load sharing between the solid and the fluid phases of the material (c) thin film lubrication as water persists on the surface of the material. The small increase of μ under static load can be explained by a small partial dehydration of the material under the pressure. In comparison, natural cartilage will lose most of its water under static load and therefore its coefficient of friction increases rapidly and to higher levels. Removal of the load and subsequent rehydration restores the initial coefficient of friction for natural cartilage.

Example 37

The coefficient of friction is a number that indicates the force resisting lateral motion of an object. It is expressed as a unitless ratio of the frictional force to the normal force. The dynamic coefficient of friction for the polyether urethane/polyacrylic acid (PEU/PAA) semi-IPN on was tested on metal, and the dynamic coefficient of friction is shown as a function of time. Briefly, a piece of Elasthane™ 55D (polyetherurethane) was soaked in acrylic acid with an initiator and cross-linker, and cured to form a water swellable semi-IPN of the present invention. Plugs 8.8 mm in diameter and 1 mm thick were cut, swollen in PBS, and then rotated at a frequency of 1 Hz against a 3/16" stainless steel disc at a contact stress of 2.0 MPa while being submerged in PBS. Using a custom-made wear tester made according to ASTM F732 standards equipped with both a force load cell and a torque load cell, the dynamic coefficient of friction was measured real-time during the wear test experiment. The dynamic coefficient of friction of the material varied between 0.005 and 0.015 over a period of 36 hours.

Example 38

Figure 44B:
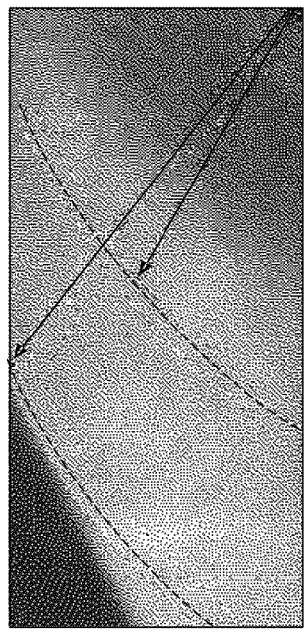
FIGS. 44A-C show the results of wear testing of the PEU/PAA semi-IPN material associated with Example 39 compared to UHMWPE sample from a metal-on-UHMWPE wear test.
Figure 44A:
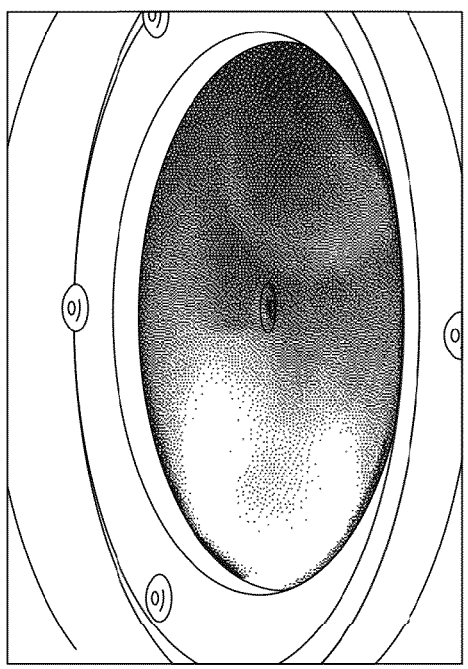
Figure 44C:
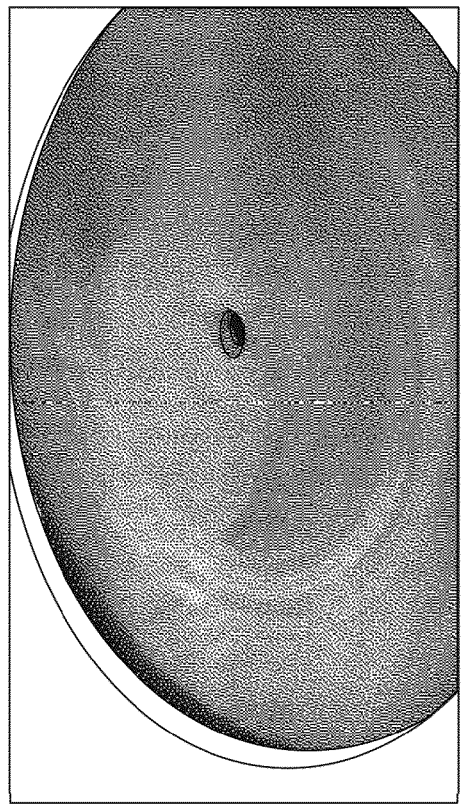
Figure 45A:
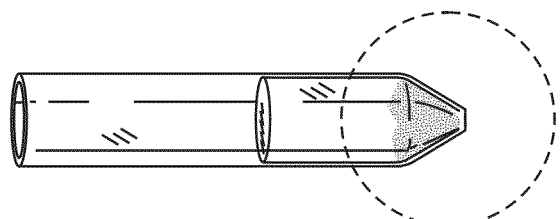
FIGS. 45A-C show the results of wear testing of the PEU/PAA semi-IPN material associated with Example 39.

Wear experiments of the PEU/PAA semi-IPN of this invention were conducted according to ASTM F732 using a pin-on-disc configuration. Results are shown in FIGS. 44, 45, and 45. Discs and pins formed from the joint interface material were tested to 2,500,000 cycles. As a basis for comparison to industry standard materials, a CoCr pin-on-UHMWPE (Cobalt chrome on ultra-high molecular weight polyethylene) disc configuration was also tested for 1,000,000 cycles.

In the test of the PEU/PAA semi IPN of this invention, the pins were 8.8 mm in diameter, 2.5 mm in thickness. The disc was 88 mm in diameter and 2.5 mm in thickness. The pins were rotated over the disc at a radius of 24 mm and at a rate of 1.33 Hz under a pneumatically applied cyclic load. A pressure regulator was used to adjust the air pressure so that the desired force was applied. The load was measured using a load cell (Sensotec Honeywell, CA) directly under the disc. The disc and the pins were mechanically isolated so that the torque caused by the friction generated between them can be measured by a torque cell (Transducer Techniques, CA) connected to a computer equipped with a data acquisition card (National Instruments, TX). The pin and discs were contained in a chamber filled with PBS. The temperature was controlled and kept constant at 37° C. using a thermocouple-resistor-fan system. Using the equation $\mu = T/r*F$, where T is the measured torque, r is the radius of rotation (=24 mm) and F being the total force applied on the pins, the coefficient of friction was constantly monitored. The coefficient of friction was found to be 0.016 and independent of the contact pressure (range tested 0.1-3.5 MPa) and slightly increased to 0.021 under heavy static contact load, but returned to the original value after fluid recovery. The wear was measured using the gravimetric method every million cycles: the disc and the pins were weighed separately after vacuum drying for 3 days. The wear test solution (PBS) was collected and visually examined; no signs of visible wear particles were noted at all steps of the tests. The wear test PBS solution was vacuum filtered using a 2.5 μm pore filter to capture any wear particles, flushed with deionized water to remove remaining PBS salts and then dried overnight under vacuum and desiccant. As a control, a similar test was performed using CoCr pins (Fort Wayne Metals, IN) on UHMWPE (Orthoplastics, UK). Three polished (Ra<1.6 μm) CoCr flat pins of OD=7 mm were tested in the same instrument against a polished UHMWPE disc of 2.5 mm thickness and OD=88 mm (rotation radius=24 mm), rotating at 1.2 Hz under 3.4 MPa static contact load and at 37° C. isolated environment.

Observation of the disc formed from the PEU/PAA semi-IPN of this invention after the test (FIG. 44A) revealed no macroscopically perceptible wear track along the pin-on-disc articulation surface. (FIG. 44B is a close-up view of the location of the wear track. Dashed lines have been added to indicate the path; the radial arrows start from the center of the disc.) In comparison, as shown in FIG. 44C, the UHMWPE disc after 2.0 M cycles of wear against CoCr pins has a visible track 126 μm deep.

Weighing of the wear test solution filtrate using a scale with a 0.01 mg resolution (Mettler Toledo, Ohio) showed that the volumetric wear rate of the PEU/PAA semi-IPN was approximately 0.6 mg/$10^6$ cycles or 0.63 mm$^3$/106 cycles or 0.63 mm$^3$/150×$10^3$ m. This value, however is close to the resolution of the methods. A schematic of the wear test solution from the wear test of the inventive joint interface material comprised of PEU/PAA semi-IPN is shown in FIG. 45 A, demonstrating an absence of particles in the PBS solution. Compare FIG. 45 A to schematics of the wear test solution of the UHMWPE disc shown in FIGS. 45 B and 45 C, which show substantial wear debris particles generated during the CoCr-on-UHMWPE wear test.

Although attention was paid to eliminate external factors such as dust, moisture and static in order to increase the accuracy of the results, the wear values are well near the statistical and practical detection limits of the methods available. These results are consistent with the hypothesis that since the PEU/PAA semi IPN according to the present invention—like natural cartilage—is comprised of mostly water, and the surface is persistently lubricated with a film of water, there is little, if any, contact between solid matrices.

Figure 45B:
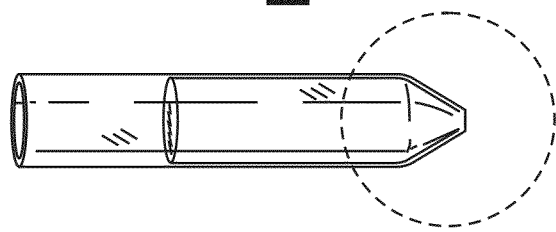
Figure 45C:
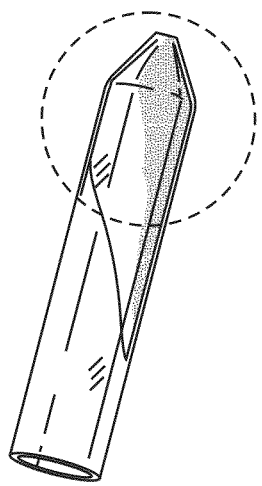
Figure 46:
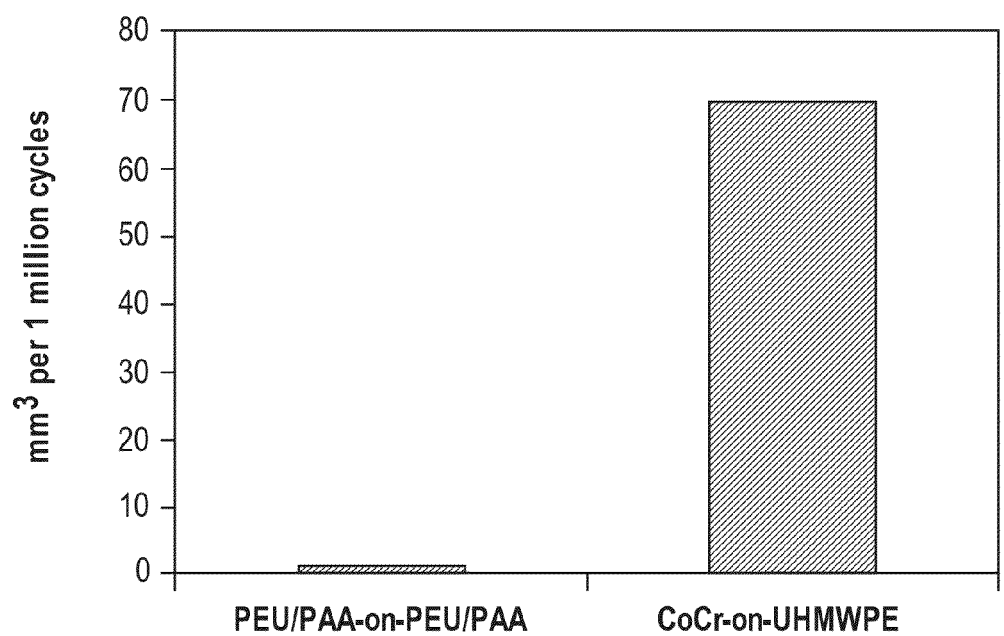
FIG. 46 shows quantification of the results of wear testing of the PEU/PAA semi-IPN material associated with Example 39.

Wear particle measurements were also taken for the CoCr-on-UHMWPE experiments, which not only created a visible wear track (FIG. 44B) on the UHMWPE disc, but generated substantial macroscopic wear debris (FIGS. 45B and C). The UHMWPE disc was weighed and the difference in weight yielded an average wear rate of 64 mg/$10^6$ cycles or 69 mm$^3$/150×$10^3$ m (FIG. 46). This study points that the joint interface material of this invention (labeled "PEU/PAA-on-PEU/PAA") is at least more than 100 more resistant to wear than the traditional combination of CoCr-UHMWPE, widely used in total joint replacements.

Example 39

FIG. 47 shows the swelling behavior of PEU/PAA and PEU in various aqueous and organic solvents. Briefly, a sheet of Elasthane™ 55D (polyether urethane) was soaked in acrylic acid with initiator and cross-linker, and cured to form a semi IPN. A small piece of the IPN or Elasthane™ 55D was obtained and weighed. The sample was soaked for 20 hours in a solution containing the solvent indicated in the Figure. (The samples were swollen, but did not dissolve). The sample was removed from the solvent, briefly dabbed dry, and then weighed again. The change in weight due to swelling is expressed as the % difference. While Elasthane™ 55D on its own does not take up water, the IPN of the present invention readily swells with water to form a lubricious, hydrated IPN. In addition, other solvents can be used to swell the starting polymer to create the IPN of the current invention. In the case of polyurethanes, the ability of various solvents to swell the material depends on the properties of the solvent (such as its polarity, acidity, and molecular weight) as well as the relative solubility of the polymer components (e.g. hard and soft segments) in the solvent.

Example 40

The swelling of polyetherurethane by acrylic acid in water and acetic acid was tested. Swelling solutions were prepared containing 10, 30, 50, and 70% acrylic acid monomer in deionized water (FIG. 48A) and in acetic acid (FIG. 48B). Small pieces of Elasthane™® 55D (polyetherurethane) were obtained and measured. A sample of the Elasthane™ was placed in each solution. The samples were removed from the solvent, the surface briefly dabbed dry, and then measured again. The change due to swelling is expressed as the final length of the specimen after equilibrium swelling ($L_f$) divided by the original length ($L_o$) minus 1; in this way, the fractional increase in length relative to the initial state (y=0) is plotted versus time. Swelling of the Elasthane™ 55D was observed using either water or acetic acid as a solvent. More swelling was observed when a higher amount of acrylic acid was used in the swelling solution. Of note, the concentration dependence of acrylic acid on the swelling of the Elasthane™ samples was different depending on whether water or acetic acid was used as the solvent.

Example 41

Figure 49:
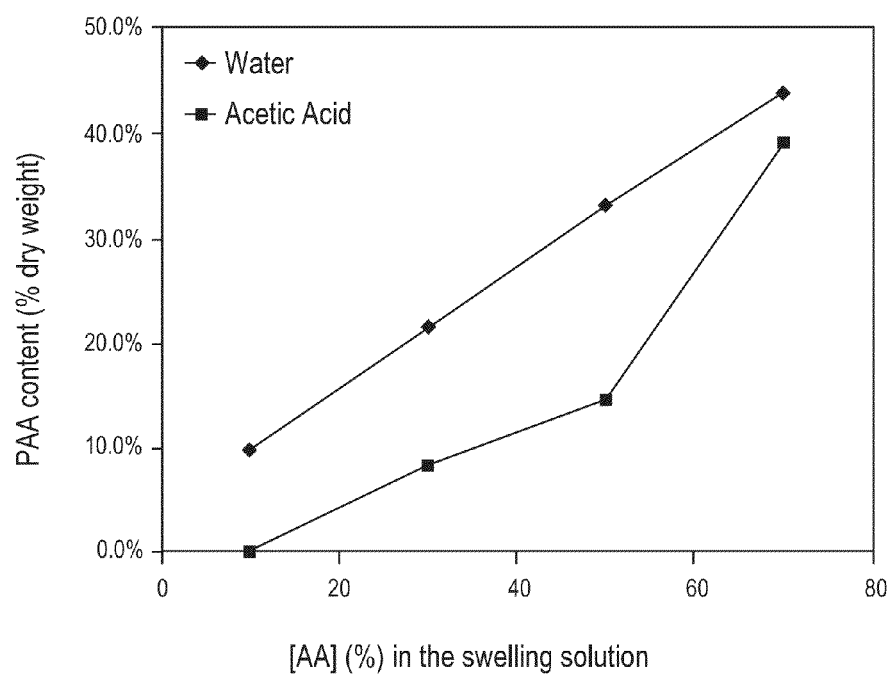
FIG. 49 shows polyacrylic acid content in the PEU/PAA semi-IPN as a function of the amount of acrylic acid in the swelling solution associated with Example 42.
Figure 50:
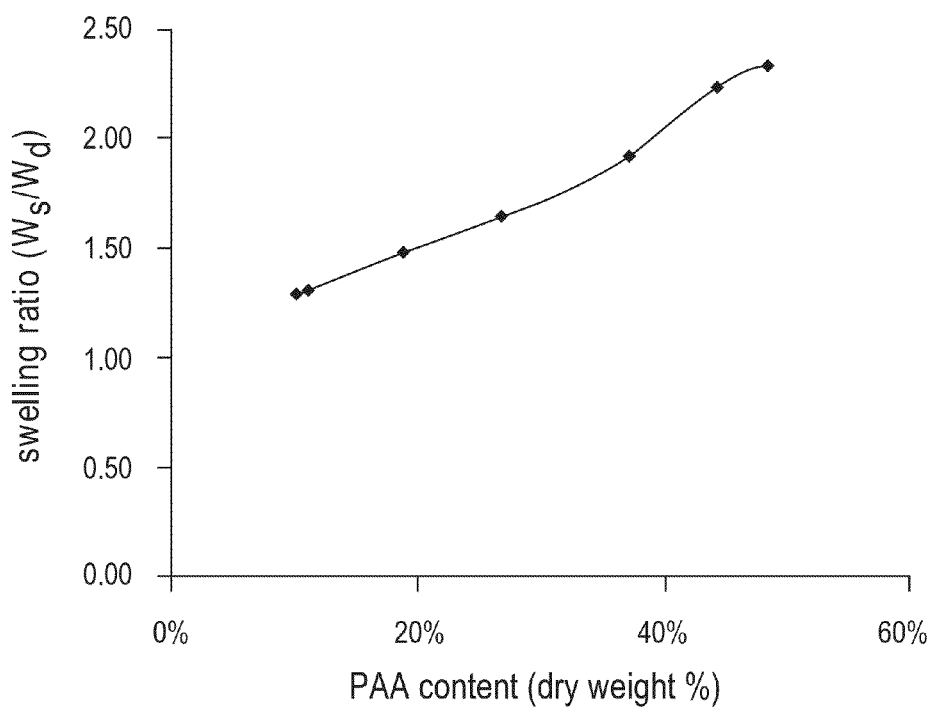
FIG. 50 shows the swelling of PEU/PAA semi-IPN as a function of the amount of polyacrylic acid in the semi-IPN associated with Example 43.

FIG. 49 shows the amount of poly(acrylic acid) present in the PEU/PAA semi-IPN after curing is plotted as a function of the starting concentration of acrylic acid monomer in different swelling solutions.

Swelling solutions were prepared containing 10, 30, 50, and 70% acrylic acid monomer in deionized water and in acetic acid. Small pieces of Elasthane™ 55D (polyetherurethane) were obtained and weighed. Samples were placed in each of the water/acrylic acid or acetic acid/acrylic acid solutions along with cross-linker and initiator. The samples were cured, swollen in acrylic acid in either water or acetic acid, removed from the solution, dried, and then weighed again. Incorporation of acrylic acid into the Elasthane™ 55D to form a semi-IPN was observed using either water or acetic acid as solvent. More incorporation of acrylic acid was observed when a higher concentration of acrylic acid was present in the swelling solution.

Example 42

Semi IPNs were prepared essentially as described in FIG. 49, and the polyacrylic acid content of the IPNs was determined. The dried materials were weighed, swollen in saline until equilibrium was reached, and weighed again. The change in weight of the semi IPN is expressed as a ratio of the weight of the swollen material/weight of the dry material (Ws/Wd) for each concentration of polyacrylic acid. An increased amount of polyacrylic acid in the polymer correlates with an increased uptake of saline into the water-swellable semi-IPN. Since the semi-IPNs in these experiments were neutralized to pH 7.4, in these experiments, the dry weight of the semi-IPN included the salts present in the saline swelling solution, since the monovalent cations (predominantly sodium, which has a MW of 23 g/mol) are counterions to the carboxylate groups in the material.

Example 43

FIGS. 51-54 show the results of creep and stress relaxation/compression testing. Tests were performed on PEU/PAA semi IPNs formed from Elasthane™ 55D (polyetherurethane) soaked in acrylic acid with initiator and cross-linker, and cured.

FIG. 51 shows the results of cyclic compression testing. The behavior of the PEU/PAA semi IPN was tested under dynamic compression conditions to determine permanent creep and creep recovery. Permanent creep is the time-dependent deformation of a material under a constant load. Creep recovery measures the rate of decrease in the applied deformation after a load is removed. Experimental setup of the compression test followed the ASTM standard D695, Standard Test Method for Compressive Properties of Rigid Plastics, with the samples being subjected to a sinusoidal loading scheme designed to mimic the physiologic, cyclic compressive loads seen in a gait cycle.

Figure 51A:
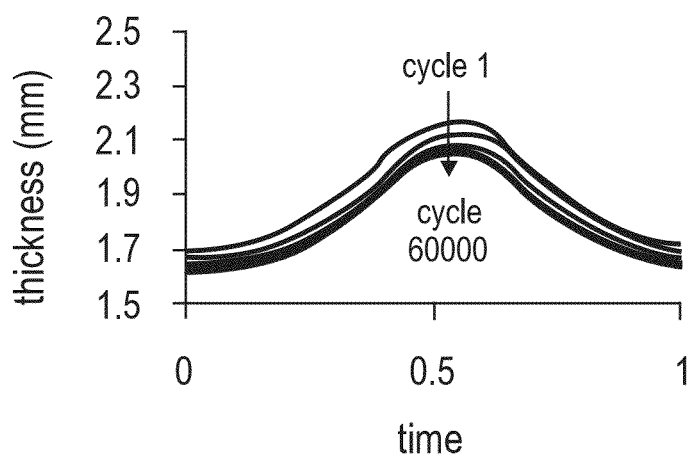
FIGS. 51A-B show the results of Dynamic Compression testing of the PEU/PAA semi-IPN material as associated with Example 44.
Figure 51B:
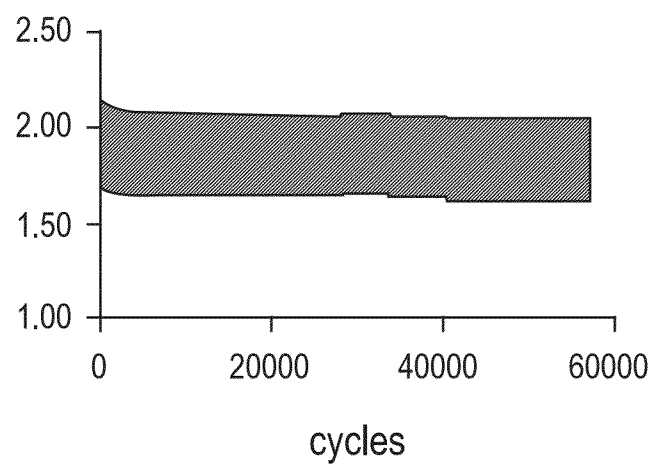

A sample of the PEU/PAA semi IPN was removed and measured in the direction of its thickness, subject to cycles of compressive stress from 0-3 MPa at a frequency of 1 Hz for over 60,000 cycles, measured again in the direction of its thickness, re-equilibrated (relaxed) in PBS to allow for recovery from creep, and measured again in the direction of its thickness. FIG. 51A shows the results of thickness measurements on representative samples subject to one-second long cycles of tests (at the 1st, 1000th, 10,000th, 20,000$^{th}$, 40,000$^{th}$, and 60,000$^{th}$ cycles) superimposed in one figure. FIG. 51B shows how the thickness of the material changes over all cycles of testing. The thickness of the material, as measured after load was removed during the cycle, dropped from an initial value of 2.160 mm at the first cycle to about 2.000 mm by the 60,000$^{th}$ cycle. However, after re-equilibration (relaxation) in PBS and creep recovery at the last cycle, the material returned to a thickness of 2.135 mm, a total loss of thickness of only 1.1% due to permanent creep.

Figure 52:
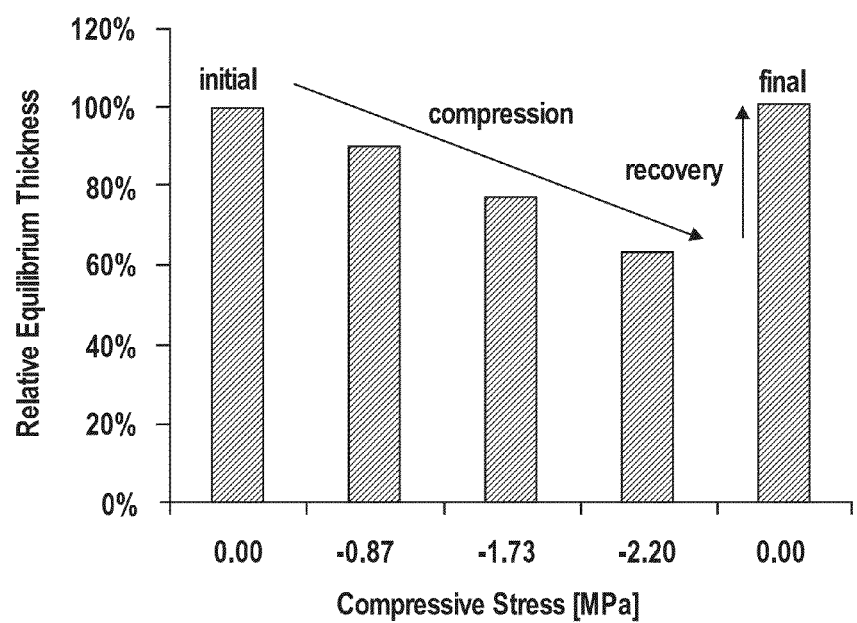
FIG. 52 shows the results of the application of a multistep stress relaxation compressive stress test to the PEU/PAA semi-IPN material followed by relaxation as associated with Example 44.

FIG. 52 presents the equilibrium compressive behavior of the PEU/PAA semi IPN as determined through a multiple-step stress relaxation test, in which a given displacement is applied and then the material is allowed to relax (equilibrate). Notably, under these test conditions, the material fully recovered to its equilibrium value after removal of the load, as shown by the last data point in FIG. 52, indicating full creep recovery. The stress of 2.20 MPa (4th data point) is 15% higher than the maximum functional stress in a hip device (total load through the hip of 3 times body weight) that is predicted by finite element models.

A static creep test was also performed (data not shown). Creep is the time-dependent deformation of a material under a constant load. The behavior of the PEU/PAA semi IPN tested under static compression was tested following ASTM D2290-01 "Standard Test Methods for Tensile, Compressive, and Flexural Creep and Creep-Rupture of Plastics". A plug of the PEU/PAA semi IPN with an initial diameter of 9.525 mm and a thickness of 1.115 mm was put under an initial stress 4 MPa in a fluid PBS bath. After applying the stress for approximately 20,000 seconds (to a total strain of 14.29%), the load was released and the material allowed to relax (re-equilibrate) in PBS. The final thickness of the plug was 1.109 mm. The final unrecovered creep after more than 40,000 cycles was 2.7%.

Figure 53:
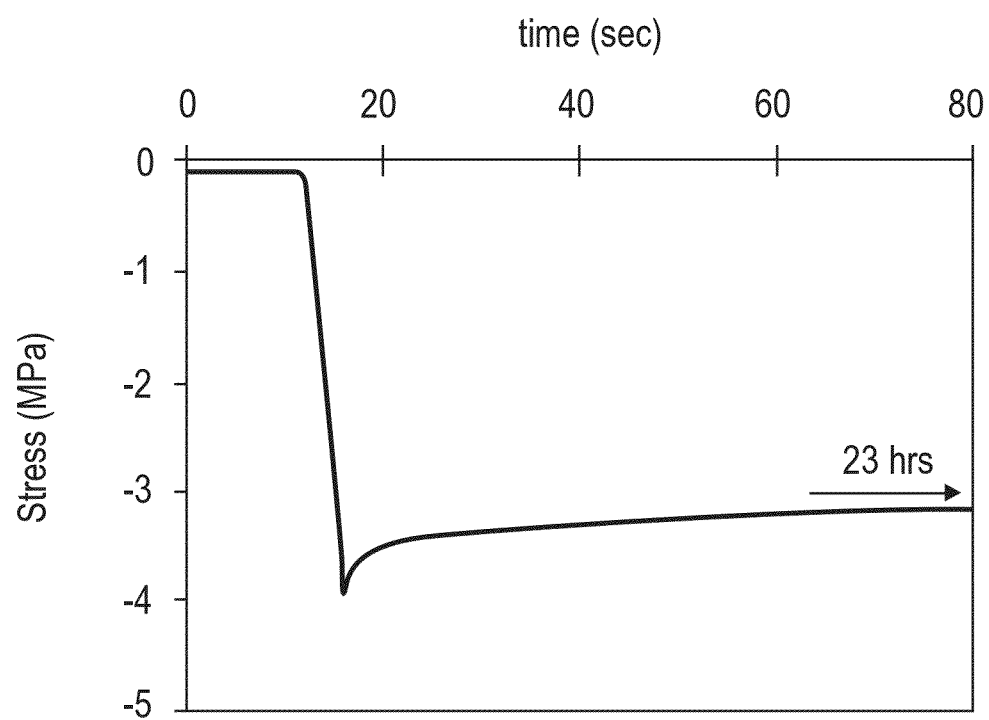
FIG. 53 shows the results of the application of application of compressive stress to the PEU/PAA semi-IPN material associated with Example 44.

FIG. 53 shows the results of a compression set test according to ASTM D395. In this test, a plug of PEU/PAA with an initial diameter of 9.525 mm and a thickness of 2.13 mm was subjected to a constant compressive strain of 15% for 23 hours at room temperature in a fluid bath filled with PBS. After allowing the material to relax and re-equilibrate in PBS, the final thickness of the plug was 2.08 mm. This yields a compression set value of 9.5%. As a basis of comparison, PEU (Elasthane™ 55D) alone exhibits a compression set value of about 45% under the same conditions (22 hrs, room temperature). Therefore, the presence of the polyelectrolyte in the PEU/PAA semi-IPN provides a way for the PEU material to resist permanent creep through rehydration of the matrix with water due to the hydrophilicity and high swellability of the negatively charged polyelectrolyte.

Example 44

FIG. 54 shows a list of some of the materials made in accordance with the present invention. The first column shows the hydrophobic polymer used. If a modification was made to the hydrophobic polymer as indicated in the second column, the material for the modification was cast with the material, or, if the modification was crosslinking functionality, the modification was added and the material prepared and crosslinked and used thereafter with the crosslinks reacted.

The monomer, comonomer (if any), crosslinker and initiator were added in the indicated solvent as indicated in the figure in order to swell the prepared hydrophobic polymer. Each hydrophobic polymer sample was allowed to swell for up to 2 days, removed from the solution, and cured using the indicated method following standard procedures. The material was washed and swollen in PBS. The abbreviations used are as follows: MBAA=methylene bisacrylamide, HMPP=2-hydroxy-2-methyl propiophenone, TEGDMA=triethylene glycol dimethacrylate, and $H_2O$=water.

Example 45

Figure 69:
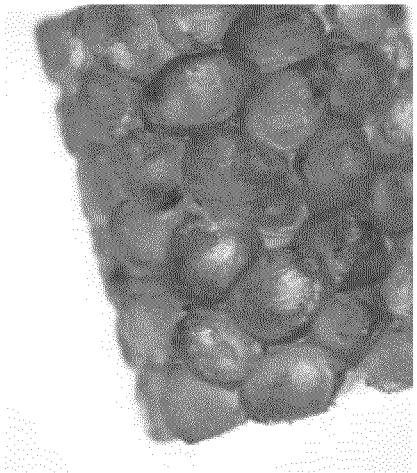
FIG. 69 illustrates a porous bone-interface material.
Figure 71:
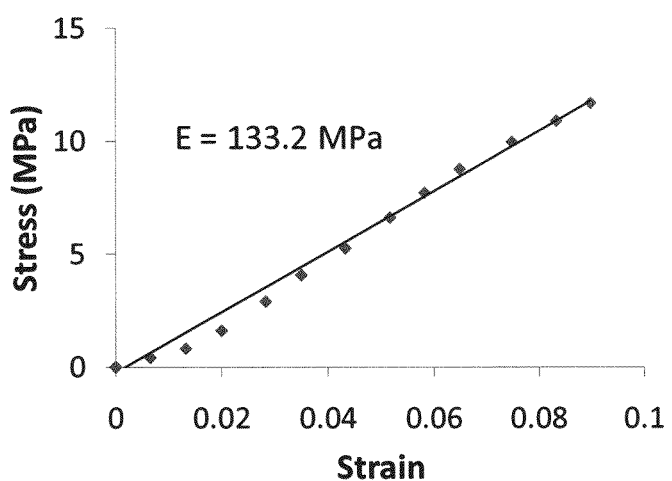
FIG. 71 illustrates the results of compressive test of the porous bone-interface material of FIG. 69.

FIG. 69 shows a porous bone-interface material that can be placed on a surface of a device such as an osteochrondral plug to facilitate bone ingrowth. The osteochrondral plug shown is a polycarbonate urethane material with a shore hardness of 75D and a compressive modulus of 2.2 GPa. To form the porous bone-interface material shown in FIG. 69, polyurethane beads ((size≈700-1300 μm) were manufactured. Porous cylinders (porosity=20-30%; pore size: 100-400 μm) were then created from the beads by heat-sintering them together. Compressive mechanical testing of the porous cylinders showed a modulus of 100-150 MPa, depending on the material porosity (see FIG. 71).

Figure 70:
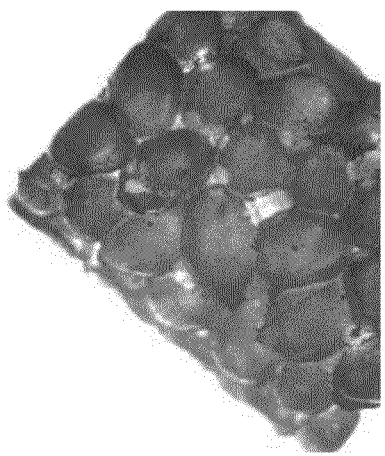
FIG. 70 illustrates red-stained portions of the bone-interface material of FIG. 69 indicating material osteoconductivity.

The bone-interface material of FIG. 69 was also found to be osteoconductive, i.e. support bone formation directly on the material surface. An osteoconductive material will facilitate calcium-phosphate (CaP) formation on the material surface when incubated in Simulated Body Fluid (SBF). To test osteoconductivity, the porous bone-interface cylinders were incubated in 1.5×SBF for 20 days. Alizarin red staining shows widespread deposition of CaP on the material surface (see FIG. 70), indicating the osteoconductivity of the bone-interface material.

An additional embodiment of the present invention takes advantage of the high mechanical strength of hydrophobic thermoset or thermoplastic polymers high mechanical strength of hydrophobic thermset or thermoplastic polymers and combines those materials with certain non-ionic polymers as a useful way to achieve increased mechanical strength with greater adhesiveness. Because of their mechanical strength, it has been desirable to use hydrophobic thermoset or thermoplastic polymer containing materials in load bearing or structural support components for a variety of purposes. For example, as discussed above, hydrophobic thermoset or thermoplastic polymers such as polyurethane can be formed into medical implants such as those used for joint arthroplasty.

This use, however, is often limited by the ability to securely attach the hydrophobic thermoset or thermoplastic polymer containing materials to a destined location or substrate. For example, a femoral head cap implant for hip replacement must be fixed to a patient's femoral head in the hip joint. To ensure patient safety and proper operation of the implant, the implant must be properly adhered to the surface of the femoral head.

In cases with high stiffness devices such as cobalt chrome, titanium, or hard plastic-ultra-high-molecular-weight polyethylene (UHMWPE), bone cements have been used as bonding/adhesive agents to fix these devices to bone. Such bone cements generally fill the meeting spaces between and on the surfaces of the device and the bone, thereby fixing the device to the bone. However, with more compliant materials that can be made from hydrophobic thermoset or thermoplastic polymers (such as polyurethane), the mechanical strength of the material and the adhesiveness between the bone cement and the implant is of particular importance in that compliant materials may conform their shapes under load.

For example, failure to provide adequate adhesion could result in sliding, dislodgement, loosening, and general movement of the implant from its proper placement. Such movement can cause pain, weaken and render the implant inoperable, and require corrective surgeries.

Various formulations and developments of cements, adhesives, fillers, bonding agents, and mechanical fixation components such as mating pegs, screws, and grooves have been suggested to address this concern. However, these approaches focus on the bonding agents or the mechanical attachment components rather than on the composition and characteristics of the compliant materials containing hydrophobic thermoset or thermoplastic polymers. One embodiment of this invention introduces materials and articles that comprise IPNs or semi-IPNs which exhibit strong adhesion with other materials such as orthopaedic anchoring compounds while also providing high mechanical strength or stiffness. The terms interlocking agent, grouting agent, anchoring compound, adhesive agent, and/or bonding agent refer broadly and interchangeably to materials that are capable of binding, fusing, adhering, filling, cementing, affixing, or otherwise attaching one material, article, object, component etc. to another.

As discussed previously, hydrophobic thermoset or thermoplastic polymers can be infused with various monomers that are polymerized to form an IPN or a semi-IPN. In some instances, the IPN or semi-IPN can extend throughout the bulk of the material or throughout only a portion of the material, e.g. a particular region or in a gradient. Depending on the selection of the monomer, the resulting IPN or semi-IPN can exhibit a variety of properties (e.g. stiffness, lubriciousness, strength, conductivity, etc.) and variability of range within each property.

The property or properties imparted depend on several factors including, but not limited to, the monomer(s) selected, the degree of monomer penetration into the hydrophobic thermoset or thermoplastic polymers prior to monomer polymerization, the grade of the hydrophobic thermoset or thermoplastic polymers, whether the hydrophobic thermoset or thermoplastic polymers are phase-separated, whether the monomer penetration is in a single region or multiple portions of the hydrophobic thermoset or thermoplastic polymers etc.

As discussed above, FIGS. 1A-C illustrate the process with respect to a thermoplastic polyurethane-based polymer containing a network of hard segments 10 (shown as open rectangles) and soft segments 12 (shown as lines). In FIG. 1B, the soft segments 12 are swollen with ethylenically unsaturated monomers with or without ionizable functional groups such as vinyl-based monomer 14 (shown as circles) and optional solvent, along with an initiator and cross-linker (not shown), while mostly not affecting the hard segment material. This swelling process is not dissolution of the polymer; the hard segments act as physical crosslinks to hold the material together as the soft segments are imbibed with the monomer(s) and optional solvent(s). After polymerization and cross-linking of the monomers, a second network 16 (shown as dark lines in FIG. 1C) is formed in the presence of the first network to create an IPN in which the second polymer (i.e., the polymerized monomer) is primarily sequestered within the soft, amorphous domain of the first polymer. Despite some degree of molecular rearrangement and further phase separation, the hard segments largely remain ordered and crystalline, providing structure and strength to the material.

The new properties provided by this IPN depend on the properties of the polymerized monomers that were introduced and on any optional post-polymerization processing. Examples of such new properties include lubriciousness, conductivity, hardness, absorbency, permeability, photoreactivity and thermal reactivity. In some embodiments, an adhesiveness property can be achieved by introducing a non-ionic polymer into hydrophobic thermoset or thermoplastic polymers to form an IPN or semi-IPN. In these embodiments, the non-ionic polymer can be selected based on the presence of the non-ionic polymer in the material to be adhered to the IPN or semi-IPN.

By way of example, in some embodiments, a material containing polyurethane may be destined for use as a joint implant that will be attached to a bone's surface with bone cement. The majority of load bearing orthopaedic bone cements comprise non-ionic polymers derived from ethylenically unsaturated monomers without ionizable functional groups, like methyl methacrylate (MMA) and styrene, or combinations thereof. Many commercially available bone cements contain a polymethylmethacrylate (PMMA) polymer or copolymer.

Typically, for PMMA bone cements, MMA monomers are initially present in a liquid state prior to bonding. To activate the bone cement, the MMA is cured (polymerized) in situ to act like a grout or filler that interdigitates with the bone trabecular space and the features of the device to be implanted. This forms an interlock between the device, PMMA bone cement, and the bone that secures device fixation.

For materials containing hydrophobic thermoset or thermoplastic polymers, bonding through interdigitation can be complemented by adhesion between an IPN or semi-IPN in the material and the bonding agent. Where a PMMA bone cement is used, PMMA can be employed as the non-ionic polymer component of a IPN or semi-IPN with hydrophobic thermoset or thermoplastic polymers. MMA monomers can be introduced by infusion/diffusion into the hydrophobic thermoset or thermoplastic polymers and polymerized to form an IPN or semi-IPN within the starting material. Once formed, the PMMA in the IPN or semi-IPN is fused and compositionally continuous with the PMMA in the bone cement.

Without being bound to any theory, it is believed that the non-ionic polymer present in the bonding agent (e.g. as a constituent/ingredient) fuses to the non-ionic polymer phase of the IPN or semi-IPN, thereby providing actual adhesion between the bonding agent and the material containing the IPN. It is further believed that adding one or more layer(s) of the bonding agent to the IPN will result in strong adhesion between the IPN containing material and the bonding agent, which serves to facilitate a strong adhesion between the IPN containing material and a destination location (e.g. bone surface).

Figure 55:
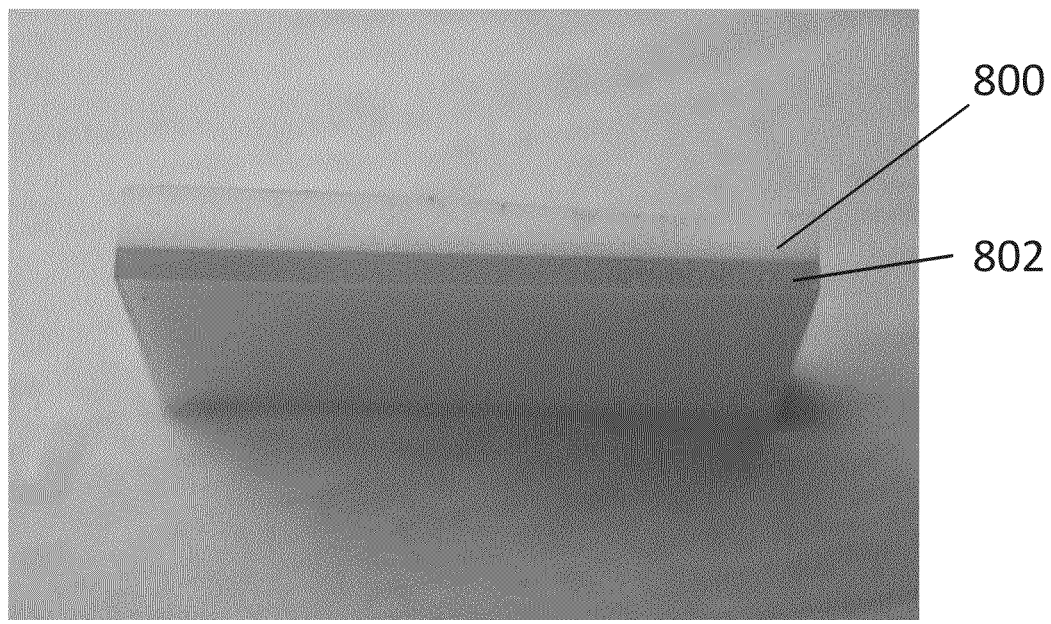
FIG. 55 is a photograph that shows an orthopedic bone cement cured on a polyurethane-PMMA IPN plate.

FIG. 55 is a photograph illustrating one embodiment where an orthopaedic PMMA bone cement (Stryker Simplex) 800 was cured (according to the company's directions) on a PMMA-polyurethane-IPN 802. To form the PMMA-polyurethane-IPN 802, the original polyurethane plate was infused by swelling a polyurethane plate with MMA. Subsequently, the MMA was polymerized to PMMA inside the polyurethane. PMMA bone cement was then applied to the IPN 802 to form layer 800.

Stiffness, adhesion, and shear strength tests were conducted on the resulting PMMA-polyurethane-IPN 802. Test results show that the PMMA-polyurethane-IPN exhibited increased stiffness, greater adhesiveness, and greater shear strength compared to the original polyurethane plate without the IPN.

With regard to stiffness, compressive tests in a universal testing machine revealed that an Elasthane™ 55D plug of OD=10 mm and 4 mm thickness had a stiffness modulus of 80 MPa whereas after the formation of a PMMA-polyurethane-IPN (at 70%-30% proportions) the stiffness modulus increase to approximately 1.5 GPa.

Although a commercially available polyurethane product, Elasthane, Bionate, Pursil, or Sylgard was used in some examples as a hydrophobic thermoset/thermoplastic polymer, it is understood in the art that any suitable hydrophobic thermoset/thermoplastic polymer may be used and there is no limitation as to the particular commercial products/tradenames described herein.

Figure 56A:
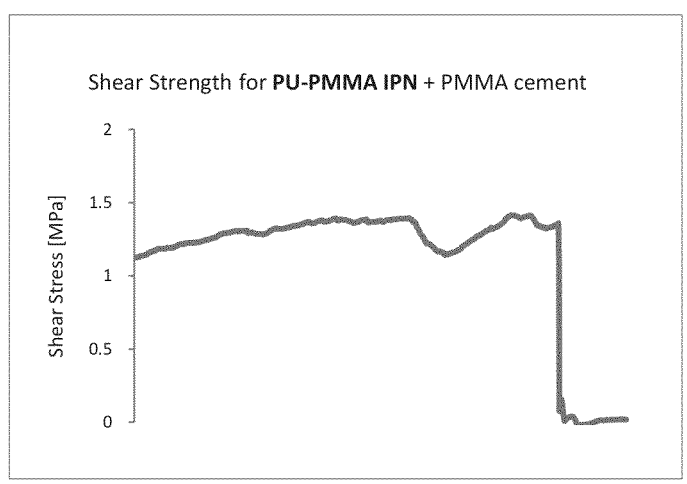
FIGS. 56A-B show the results of shear testing on a polyurethane plate compared to a polyurethane-PMMA IPN plate.
Figure 56B:
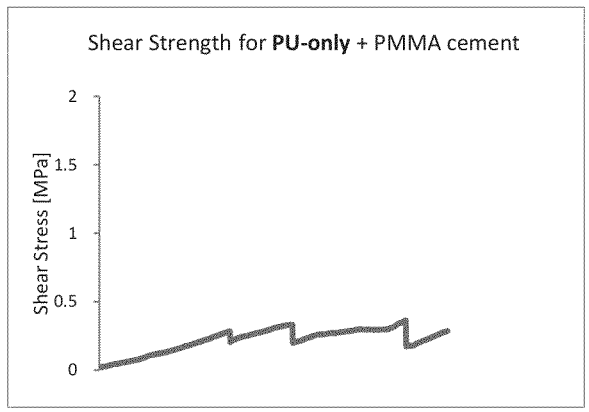

FIGS. 56A-B show the shear strength properties of the PMMA-polyurethane-IPN compared to the original polyurethane material. The adhesion between the PMMA-polyurethane-IPN and the PMMA cement was tested using a universal mechanical testing machine. As shown in FIG. 56A, shear tests of the PMMA-polyurethane-IPN with a PMMA cement layer demonstrated average shear strength of 1.35 MPa, which far exceeds the requirements for a total hip replacement system. In comparison, as shown in FIG. 56B, the shear strength of the polyurethane alone with a PMMA cement layer was approximately 0.25 MPa. This data indicates that use of the PMMA-polyurethane IPN increased the stiffness of the starting material while also improving the adhesion between the starting material and the PMMA cement.

Although the examples above illustrate the use of the MMA monomer to form a PMMA-polyurethane-IPN, it can appreciated that any number of suitable monomers can be used to form an IPN or semi-IPN which imparts properties such as stiffness, strength, or adhesiveness to a thermoset/thermoplastic polymer starting material. This can be understood more generally as an IPN or a semi-IPN formed in a material containing a hydrophobic thermoset or thermoplastic polymer T by introducing a monomer P' into thermoset or thermoplastic polymer T, which is then polymerized from monomer P' to penetrating polymer P.

In other embodiments, an exemplary list of monomer P' suitable for this process include any number or combinations of ethylenically unsaturated monomers that are not ionizable, i.e. do not have chemical groups that can bear positive or negative charge such as (but not limited to) methyl acrylate, methyl methacrylate, hydroxyethyl acrylate/methacrylate, and styrene. In further embodiments, suitable non-ionic polymers P include polymethylmethacrylate, polystyrene, or a PMMA-polystyrene copolymer.

In further embodiments an exemplary list of hydrophobic polymers modifiable by the process of this invention includes the following: Acrylonitrile butadiene styrene (ABS), Polymethylmethacrylate (PMMA), Acrylic, Celluloid, Cellulose acetate, Ethylene-Vinyl Acetate (EVA), Ethylene vinyl alcohol (EVAL), Kydex, a trademarked acrylic/PVC alloy, Liquid Crystal Polymer (LCP), Polyacetal (POM or Acetal), Polyacrylates (Acrylic), Polyacrylonitrile (PAN or Acrylonitrile), Polyamide (PA or Nylon), Polyamide-imide (PAI), Polyaryletherketone (PAEK or Ketone), Polyhydroxyalkanoates (PHAs), Polyketone (PK), Polyester, Polyetheretherketone (PEEK), Polyetherimide (PEI), Polyethersulfone (PES)—see Polysulfone, Polyethylenechlorinates (PEC), Polyimide (PI), Polymethylpentene (PMP), Polyphenylene oxide (PPO), Polyphenylene sulfide (PPS), Polyphthalamide (PPA), Polystyrene (PS), Polysulfone (PSU), Polyvinyl acetate (PVA), Polyvinyl chloride (PVC), Polyvinylidene chloride (PVDC), Spectralon, Styrene-acrylonitrile (SAN), Polydimethylsiloxane (PDMS), and Polyurethanes (PU).

As discussed, to impart adhesiveness, any number or combination of hydrophobic thermoset or thermoplastic polymers and non-ionic polymers can be employed to form a suitable IPN or semi-IPN. In some instances, the non-ionic polymer P for forming the IPN or semi-IPN is selected based on its presence as an ingredient or constituent in a material to be adhered to by the IPN or semi-IPN (i.e. the material also contains some amount of non-ionic polymer P.) In other alternative embodiments, the non-ionic polymer P is selected based on its affinity to the material where the non-ionic polymer P may not be a constituent of the material. For example, non-ionic polymer P may exhibit affinity to other constituents present in a bonding agent. The formulation of a commercially available bone cement is provided below as an example of non-ionic polymer components present in an anchoring material that can be used to form an IPN:

| Stryker Simplex P: | |
|---|---|
| Liquid component (20 mL): | |
| Methyl methacrylate (monomer) | 97.4% v/v |
| N,N-dimethyl-p-toluidine | 2.6% v/v |
| Hydroquinone | 75 ± 15 ppm |
| Powder component (40 g): | |
| Polymethyl methacrylate | 15.0% w/w |
| Methyl methacrylate-styrene-copolymer (contains 1.7% Benzoyl Peroxide) | 75.0% w/w |
| Barium sulfate, U.S.P. | 10.0% w/w |

Additionally, in some embodiments, the adhesive force between an anchoring compound or bonding material and a hydrophobic thermoset or thermoplastic-non-ionic polymer-IPN device can be increased by adding roughness (micron-to-millimeter level) to the device or/and by adding anchoring features such as grooves, pegs, protrusions, recessions, etc. The roughness or the features can added to the device by construction (during for example injection molding) or at a later stage by addition (gluing, solution casting, etc.)

Moreover, the IPN can incorporate either chemically or physically within its bulk or its surface certain additives such as antioxidants (e.g., Vitamin C, Vitamin E, Irganox®, or santowhite powder) and/or anti-microbial agents (e.g., antibiotics). These can be chemically linked to the material by, for example, esterification of the anti-oxidant with any vinyl-group containing monomer such as methacrylate, acrylate, acrylamide, vinyl, or allyl ether.

Another aspect of this invention provides a process for preparing the IPN or semi-IPNs as described. As discussed above, a process of preparing an IPN or a semi-IPN includes placing a monomer solution in contact with a hydrophobic thermoset or thermoplastic polymer, diffusing the monomer solution into the thermoset or thermoplastic polymer; and polymerizing the monomers to form a polymer within the thermoset or thermoplastic polymer, which results in an IPN or semi-IPN. As also described above, selection of the monomer(s) or thermoset or thermoplastic polymer and/or the conditions of each part of the process can affect the properties of the resulting IPN/semi-IPN.

To form an adhesive IPN/semi-IPN with non-ionic polymer P, a non-ionizable monomer P' solution can be placed in contact with a solid form of a hydrophobic thermoset or thermoplastic polymer T. The non-ionizable monomer P' solution is allowed to infiltrate and penetrate through the thermoset or thermoplastic polymer T. Once a suitable degree of penetration occurs, the monomer P' is polymerized in the thermoset or thermoplastic polymer T to form an IPN/semi-IPN that has an adhesiveness property when the non-ionic polymer P phase in the IPN/semi-IPN is brought into contact with a bonding agent containing the same non-ionic polymer P.

Polymerization can be accomplished by dissolving 1% (w/w) 2-hydroxy-2-methylpropiophenone photoinitiator in an MMA solution, swelling the polyurethane with the MMA/photoinitiator solution, and shining UV light at $2\,mW/cm^2$ for 10 minutes onto the swollen polyurethane. However, any number of photoinitiators and concentrations thereof can also be used depending on their solubility with the precursor solutions/materials.

Penetration of the monomer P' into the starting material can be carried out by submersing and swelling the entire material or piece with a monomer solution for a predetermined amount of time. Alternatively, the swelling can be done by partially exposing the material to a monomer solution, thereby reaching a partial or one side treatment. Depending on the swelling time and/or factors, a desired degree of treatment can be achieved on regions of the material. For example, in some embodiments, the monomer P' infusion occurs by submerging the entire thermoset or thermoplastic polymer T solid form in the monomer P' solution. In further embodiments, a section or region of the thermoset or thermoplastic polymer T solid form is exposed to the monomer P' solution without fully immersing the solid form in the solution. In further embodiments, the entirety of the thermoset or thermoplastic polymer T may ultimately be placed in contact with the monomer P' solution; however, the exposure process may include iterative contacts to various regions of the solid form to ultimately expose the entire solid form to the monomer P' solution.

Figure 57A:
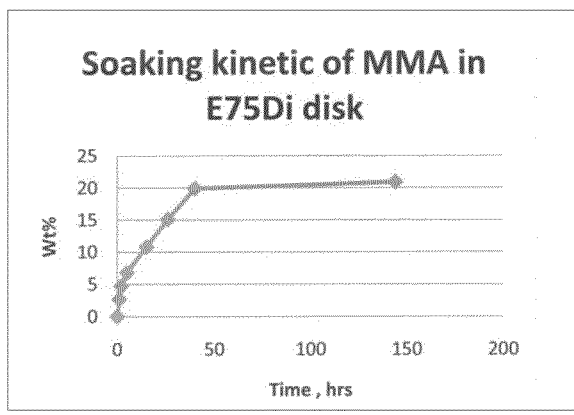
FIGS. 57A-D show the swelling kinetics results for two commercial medical grades of polyurethane.
Figure 57B:
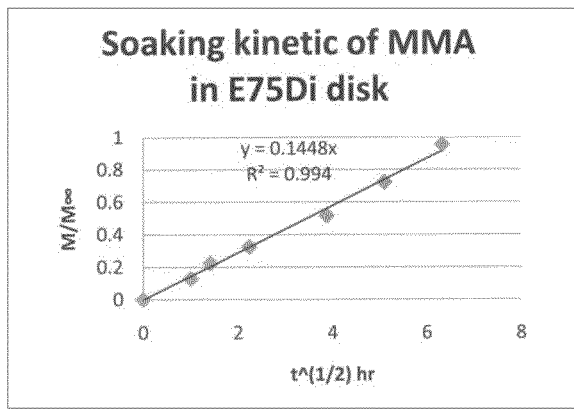
Figure 57C:
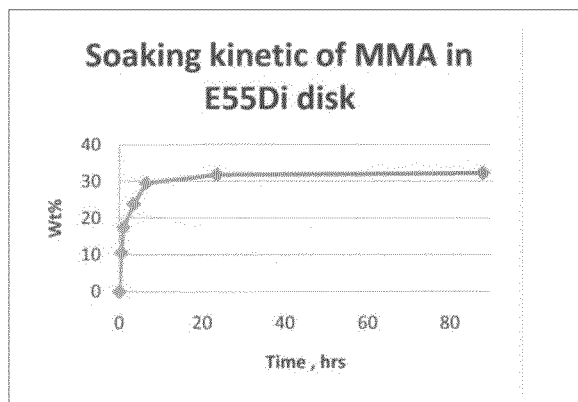
Figure 57D:
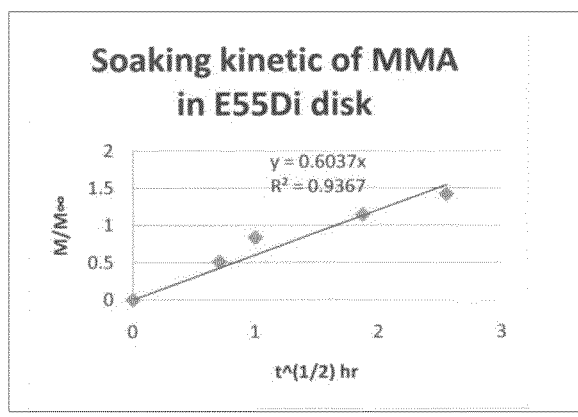

As shown in FIGS. 57A-D a swelling kinetics study was performed on two commercial medical hardness grades of polyurethane, Elasthane™ 55D and Elasthane™ 75D. In one study, a disk of Elasthane™ 75D was submerged in a MMA solution for about 150 hours. In a second study, disk of Elasthane™ 55D submerged in MMA solution past 80 hours. The degree of swelling accomplished for each grade is indicated by the weight percentage change of the disks at various time points. FIGS. 57B and 57D demonstrate the logarithmic relationship of the swelling process.

As can be appreciated in the art, the terms "entire" or "entirety" is not limited to all available surface area or volume of the solid form. Rather, the terms broadly refer to the points, area, volume, etc. that may be available for contact or exposure by the solution. For example, in some embodiments, the available exposure space on a solid form capable of forming an IPN/semi-IPN may be less than the full surface area or volume provided by the dimensions of the solid form.

In further embodiments, where the IPN/semi-IPN need only be present in a portion, side, quadrant, or region of the solid form, one or more section(s) of the thermoset or thermoplastic polymer can be selectively exposed to the monomer P' solution. For example, in the case of a joint implant made with a thermoset or thermoplastic polymer, the bone interfacing surface may be modified to include an IPN/semi-IPN to strengthen the implant and facilitate adhesion of the device to a bone cement. In such embodiments, the monomer P' solution is placed in contact with the thermoset or thermoplastic polymers in the bone interfacing surface of the device. The monomer P' solution is allowed to diffuse into the implant to the extent sufficient to impart adhesiveness and higher mechanical strength in the target location of the implant.

Affecting the amount or degree of diffusion into the implant can be accomplished by controlling the conditions of the diffusion. For example, conditions that can affect the degree of IPN penetration include modifying exposure time to the monomer P' solution, grade of the solid form, concentration of the monomer P' solution, region(s) of the solid form exposed, etc. By modifying any number or combination of these conditions (or others) the regions and degrees of adhesiveness, stiffness, shear strength, etc. can be adjusted to a suitable amount.

In additional embodiments, a solvent can be used to deliver monomers that otherwise would not mix easily (or solubilize) with the polymer or to one (or more phases) of the polymer. Solvents that can be used include, but are not limited to, di- or trichloromethane and dimethyl sulfoxide (DMSO). Depending on the solubilities in the phases of the polymer, solvents with varying degrees of swelling the polymer can be determined. Solubilities of the solvents and component material to be swollen can be obtained from polymer textbooks such as The Polymer Handbook or measured experimentally.

In another aspect of the invention, a concentration gradient can form within the starting homopolymer or thermoset/thermoplastic polymer. As shown in FIG. 2, a gradient can form in a material 20 along a thickness direction, with the IPN formed on one side 22 and extending in a diminishing concentration to another side 24, e.g., substantially only homopolymer. In FIG. 3, the IPN concentration gradient is radial within material 30, with the outer surface 32 being the highest concentration of IPN and the center or core 34 having the lowest concentration of IPN. A reverse gradient can also be made in the case of a cylinder or a sphere, with the IPN disposed in the core of the shape and the hydrophobic polymer being disposed in the outer aspect of the shape.

In some embodiments, a concentration gradient can be created by employing an IPN in a homopolymer where the concentration of the IPN changes from one region of the starting material to another. For example, a monomer solution that is allowed to diffuse into only one side of a polyurethane solid form will form an IPN through a thickness on that side of the solid form. The resulting material can contain a side with pure polyurethane and a side with IPN. Within the IPN side, the concentration of the penetrating polymer may not be uniform and, in some instances, will show a higher concentration of penetrating polymer at the site of direct exposure (surface that was in direct contact with the monomer solution) and diminishing concentration of the penetrating polymer through a thickness of the solid form from the site of direct exposure. A transition area may exist between the IPN and the pure polyurethane regions where the concentration of the penetrating polymer diminishes until effectively the IPN region merges with a non-IPN region of pure polyurethane.

FIG. 60 illustrates how the concentration gradient of the hydrophobic polymer and the non-ionic polymer can vary across the thickness (between the two surfaces) of a gradient IPN. The composition gradient yields a property gradient in which the IPN is adhesive and stiff on one side, and less adhesive (or not adhesive) and less stiff on the other.

In some variations, a concentration gradient can form by adjusting the exposure time or area of the thermoset/thermoplastic polymer in a monomer solution. Similarly, a concentration gradient can also result by limiting the exposure time of the solid form to the monomer solution. Depending on these and other factors, a gradient of material composition across a section (e.g. thickness) of the polyurethane solid form can be achieved.

By way of example, a concentration gradient can be created in a solid form of polyurethane by exposing one side of the solid form to a MMA solution. The MMA monomers penetrate the solid form through the contact side but can be limited in the degree of diffusion by factors such as the area available for penetration, exposure time, and the structure of the solid form (e.g. phases present in the thermoset/thermoplastic polymer). Once the MMA monomers are allowed to diffuse through one side of the solid form, the monomers are polymerized to form a PMMA IPN/semi-IPN within the solid form. In this example, the resulting material can exhibit a concentration or composition gradient with the IPN/semi-IPN on one side, the thermoset/thermoplastic polymer on another side, and a transition region with decreasing PMMA content from one side to the other. In some embodiments, the concentration gradient allows regions of the starting structure to exhibit properties such as greater stiffness, adhesiveness, or strength while at the same time preserving sections having the original material.

The use of concentration gradients within thermoset/thermoplastic polymer materials is especially advantageous in the creation of osteochondral grafts for orthopaedic joint replacement materials. For instance, in the case of a joint arthoplasty, the bone interfacing side of a polyurethane implant is exposed to a MMA monomer such that it forms a PMMA-polyurethane IPN through a thickness of the implant. While one side of the implant remains pure thermoplastic, the bone interfacing surface exhibits greater adhesiveness while the IPN also provides increased mechanical strength through the thickness of the implant where the IPN exists. A PMMA bone cement can be applied to the IPN (bone interfacing) surface to facilitate bonding of the implant to a bone surface.

Figure 58B:
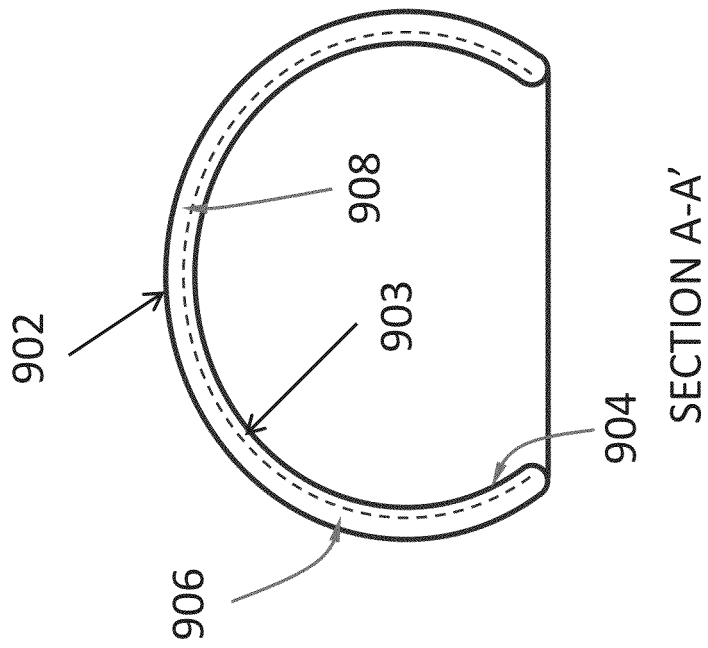
FIG. 58B shows a cross-sectional view along line A-A' of the orthopaedic implant of FIG. 58A.
Figure 58A:
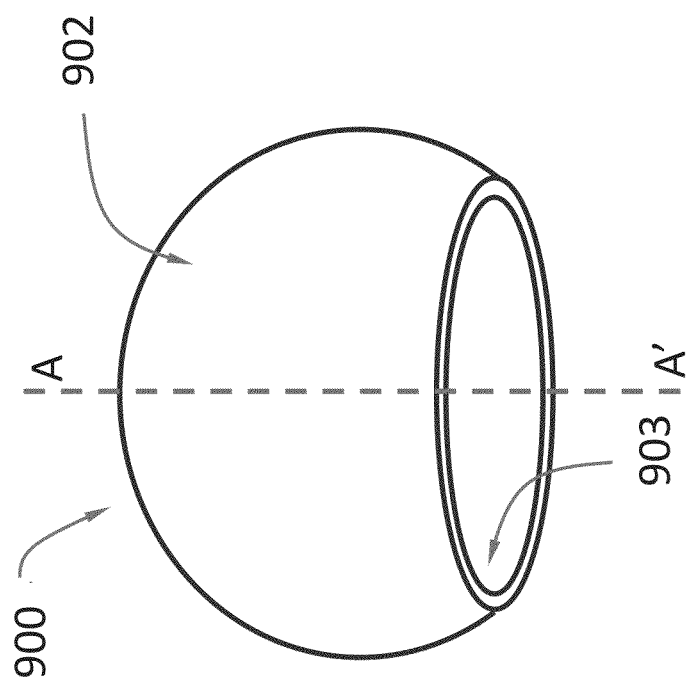
FIG. 58A shows an orthopaedic implant having a hydrophobic adhesive IPN or semi-IPN according to this invention.

In further embodiments, the starting material for the concentration gradient is a lubricious hydrophobic thermoset/thermoplastic material. Such materials may be one of those previously discussed such as a thermoset or thermoplastic polymer with a lubricious IPN/semi-IPN. For example, an orthopaedic device 900 that is designed to replace femoral head cartilage is shown in FIGS. 58A-B. The orthopaedic device 900 comprises a lubricious polyurethane based material. To impart adhesiveness to the bone contacting surface, internal bone contacting area 903 and surface 904 is infused with a MMA monomer according to the method described above. The MMA monomer is then polymerized, forming an IPN/semi-IPN layer in the bone contacting surface 904 and through a thickness in the bone contacting area 903. The resulting implant has a bone contacting area 903 and surface 904 with adhesive properties, a stiffness gradient through the thickness of the implant, and an external unmodified area 906 with an unmodified surface 902. The dotted line 908 shows a general illustration of a transition area between the IPN and the unmodified starting material. Although the dotted line 908 indicates the general area at which the gradient fades out and transitions to a pure polyurethane (or non-IPN) portion, this transition area can be anywhere along the thickness of the implant or may be absent altogether in other embodiments. In other embodiments, no discrete boundary exists between the PMMA-polyurethane IPN and the unmodified lubricious polyurethane portions of the device.

The polyurethane of the example above may be formed by any process and may contain any additional materials, including but not limited to those described in U.S. patent application Ser. No. 12/148,534 filed Jul. 4, 2008 and entitled "Hydrogel Arthroplasty Device", U.S. patent application Ser. No. 12/499,041, filed Jul. 7, 2009, and entitled "Hydrophilic Interpenetrating Polymer Networks Derived from Hydrophobic Polymers", U.S. patent application Ser. No. 12/536,233 filed Aug. 5, 2009 and entitled "Polyurethane-Grafted Hydrogels".

As described above, the forming or shaping of the IPN and semi-IPN articles according to embodiments of this invention can be done prior to or after creating the IPN/semi-IPN in the material. For example, a solid form of polyurethane can be pre-formed into a joint implant having a bone interfacing surface and a joint interfacing surface. The implant is then exposed to a monomer solution, which is polymerized to an IPN/semi-IPN in the implant.

Another aspect of the invention takes advantage of the high mechanical strength of thermoset or thermoplastic polymers and the ability to modify these materials to impart more than one desired property. For example, a thermoset or thermoplastic polymer can be made lubricious, conductive, and adhesive through the use of combinations of monomers and IPNs.

More than one property can be imparted to a hydrophobic thermoset/thermoplastic polymer by introducing a first monomer solution into the thermoset/thermoplastic polymer and polymerizing to form a first IPN/semi-IPN in the thermoplastic polymer. The process can be further repeated to introduce additional IPNs/semi-IPNs to the starting polymer.

This process is particularly useful where different sections of the starting material require different properties or sets of properties from other sections. For example, a polyurethane femoral head cap implant has a bone interfacing surface that will engage and affix to a femur surface and a joint interfacing surface that will engage the hip socket. To securely affix the implant to the bone, implant's bone interfacing surface can be infused with a monomer (e.g. MMA) solution capable of imparting adhesiveness, stiffness, or strength. With a MMA solution, the MMA monomers penetrate the bone interfacing surface of the implant and polymerize to form a PMMA-polyurethane IPN/semi-IPN in the bone interfacing surface. On the joint interfacing surface, a hydrophilic polymer can impart a lubricious surface that mimics natural cartilage. To do so, the joint interfacing surface is infused with an ionic monomer solution that polymerizes to form a hydrophilic IPN/semi-IPN in the joint surface.

In some embodiments, the multiple IPNs/semi-IPNs share the same starting thermoset/thermoplastic polymer with different penetrating polymers. This can be understood as a material containing an IPN/semi-IPN with a penetrating polymer P and a thermoset or thermoplastic polymer T and another IPN/semi-IPN with the same thermoset/thermoplastic polymer T and a penetrating polymer S. Multiple IPNs/semi-IPNs can exist in the same, overlapping, or distinct regions of the starting material. In the implant example above, the adhesive IPN on the bone interfacing surface and the lubricious IPN on the joint interfacing are disposed on different sides of the implant where the two IPNs do not overlap. However, multiple IPNs may coexist or overlap in sections of the material. Similarly, in some embodiments, multiple IPNs may overlap in certain portions of the material but not in others. Additionally, starting material or non-IPN region may be disposed adjacent to an IPN section such that the starting material region is next to one or more IPN sections. For example, a starting material region may be "sandwiched" between two IPN regions.

Moreover, the multiple IPNs/semi-IPNs do not necessarily provide different properties to the material. Some materials contemplated include more than one lubricious portion while other materials may have multiple adhesive sections. In embodiments where more than one bonding agent is used on a material, it is understood that the same IPN may not have the same degree of affinity to the different bonding agents (e.g. a PMMA-IPN may not adhere as well to bone cement with a high polystyrene content). In such cases, different penetrating polymers may be used to form different adhesive IPNs where each IPN is configured to optimize bonding with a target substance or material.

Alternatively, the multiple IPNs/semi-IPNs may employ the same penetrating polymer. For example, a polyurethane solid form may contain a PMMA-polyurethane-IPN on two different surfaces. In some instances, one IPN may be formed first and a second IPN with the same penetrating polymer formed at a later time.

Furthermore, as can be appreciated in the art, any combination of hydrophobic, non-ionic, hydrophilic, and ionic polymers can be used with a thermoset/thermoplastic starting polymer to create one or more IPNs/semi-IPNs in the starting polymer. For example, a material may contain two hydrophobic or two hydrophilic IPNs or combinations, variations, or permutations thereof.

As discussed, in some embodiments, the process of preparing multiple IPNs/semi-IPNs in a thermoset or thermoplastic polymer solid form includes the steps of placing at least one region of the solid form in contact with a monomer solution, diffusing the monomer solution into the thermoset/thermoplastic polymer, polymerizing the monomer into a penetrating polymer, and repeating these steps with additional monomer solutions. In other embodiments, the thermoset or thermoplastic polymer solid form is exposed and swollen with each of the monomer solutions before polymerization of the monomers into their respective penetrating polymers. Depending on the desired product, the process can be modified to adjust the placement of the IPNs/semi-IPNs. For example, each of the IPNs/semi-IPNs can overlap or exist in separate regions of the hydrophobic thermoset or thermoplastic polymers.

In additional embodiments, more than one concentration gradient can form in a thermoset/thermoplastic polymer with multiple IPNs/semi-IPNs. In some instances, a material having two IPNs (or more) may have two or more concentration gradients where each gradient provides regions of varying degrees of penetrating polymer concentration and varying degrees of imparted properties. As with the gradients discussed previously, the concentration gradient can be created by adjusting conditions such as the thermoset/thermoplastic polymer's exposure area and time to a monomer solution. By adjusting conditions for one or more of the monomer solutions employed, multiple concentration gradients can exist in the starting material.

For example, FIGS. 59A-C show an othropaedic device 910 that is meant to replace femoral head cartilage. The device 910 is made from a polyurethane starting material that is infused with two monomer solutions to form two concentration gradients on separate regions of the device 910. The orthopaedic device 910 has an external contact surface 912 designed to engage the hip joint and an internal surface 914 designed to engage the surface of the femur. A hydrophilic monomer can be diffused into the polyurethane starting material on the external contact surface 912 and polymerized to form a lubricious IPN. Additionally, a non-ionic monomer such as MMA can be diffused into the polyurethane starting material on the internal contact surface 914 and polymerized to form an adhesive, stiffness, strength gradient (and an adhesive surface).

In some embodiments, this process forms two IPNs with two concentration gradients, one on the lubricious side with surface 912 and one on the anchoring side with surface 914. The concentration gradient on the lubricious side may exhibit diminishing concentration of the penetrating polymer through a thickness of the implant, whereby the properties of the IPN may also decrease through a thickness of the implant in relation to the concentration of the penetrating polymer in the IPN. For example, an IPN area of higher concentration of the penetrating polymer may have a higher degree of lubriciousness than an area of lower concentration. Similarly, on the anchoring side with surface 914, the concentration of the penetrating non-ionic polymer may also diminish from one region to another through the IPN and afford a relative reduction in adhesiveness through the same area.

Because there are numerous ways of creating and placing multiple IPNs (and concentration gradients) on a starting material, behavior of a concentration gradient is not limited to diminishing concentration of a penetrating polymer through a thickness of a starting material. Gradients can be formed across a surface rather than a thickness of a material. Moreover, multiple IPNs may overlap partially or fully at regions in the starting material, or alternatively, multiple IPNs may be placed in distinct and separate regions. For example, FIGS. 59B and 59C show a region 916 between the two IPNs concentration gradients that remains as unmodified starting polyurethane material. Dotted line 918 shows generally a transition area between the concentration gradient on the lubricious side with surface 912 and the area of pure polyurethane material 916. Similarly, dotted line 920 shows generally a transition area between the concentration gradient on the anchoring side with surface 914 and a region of pure starting material 916. Although shown as dotted lines in 918 and 920, the transition areas contemplated do not require a discrete boundary between an IPN and the unmodified polyurethane material. In some embodiments, more than one gradient can meet in a portion of the starting material without a transition area from one gradient to pure starting material. In some embodiments, the transition area between gradients or gradients and starting material can be anywhere along a dimension of the material (e.g. implant) or may be absent altogether. Alternatively, in further embodiments, IPNs and gradients can be prepared such that the transition areas, points, regions between IPNs, gradients, or starting materials distinctly separate differing areas by way of boundaries or layers.

In the above example, it is understood that the multiple IPNs/semi-IPNs share the same starting thermoset/thermoplastic polymer with different penetrating polymers. This can be understood as an implant containing an IPN/semi-IPN with a penetrating polymer P and a thermoset or thermoplastic polymer T and another IPN/semi-IPN with the same thermoset or thermoplastic polymer T and a penetrating polymer S. In additional embodiments, the hydrophobic thermoset/thermoplastic material can include more than a double gradient, e.g. triple or more gradients imparted by multiple IPNs/semi-IPNs.

Figure 61A:
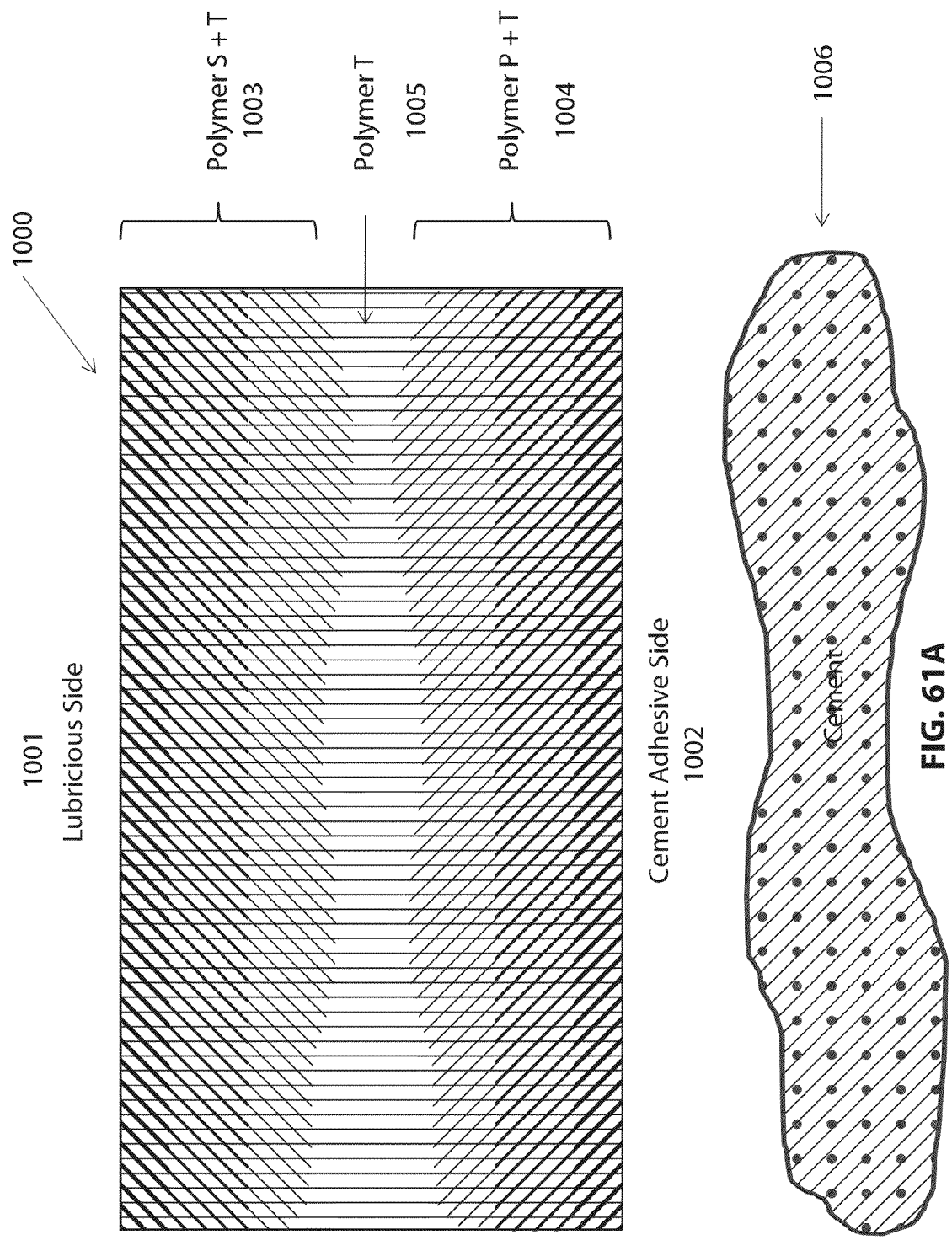
FIGS. 61A-B show an example of a double gradient with a lubricious and adhesive gradient.
Figure 61B:
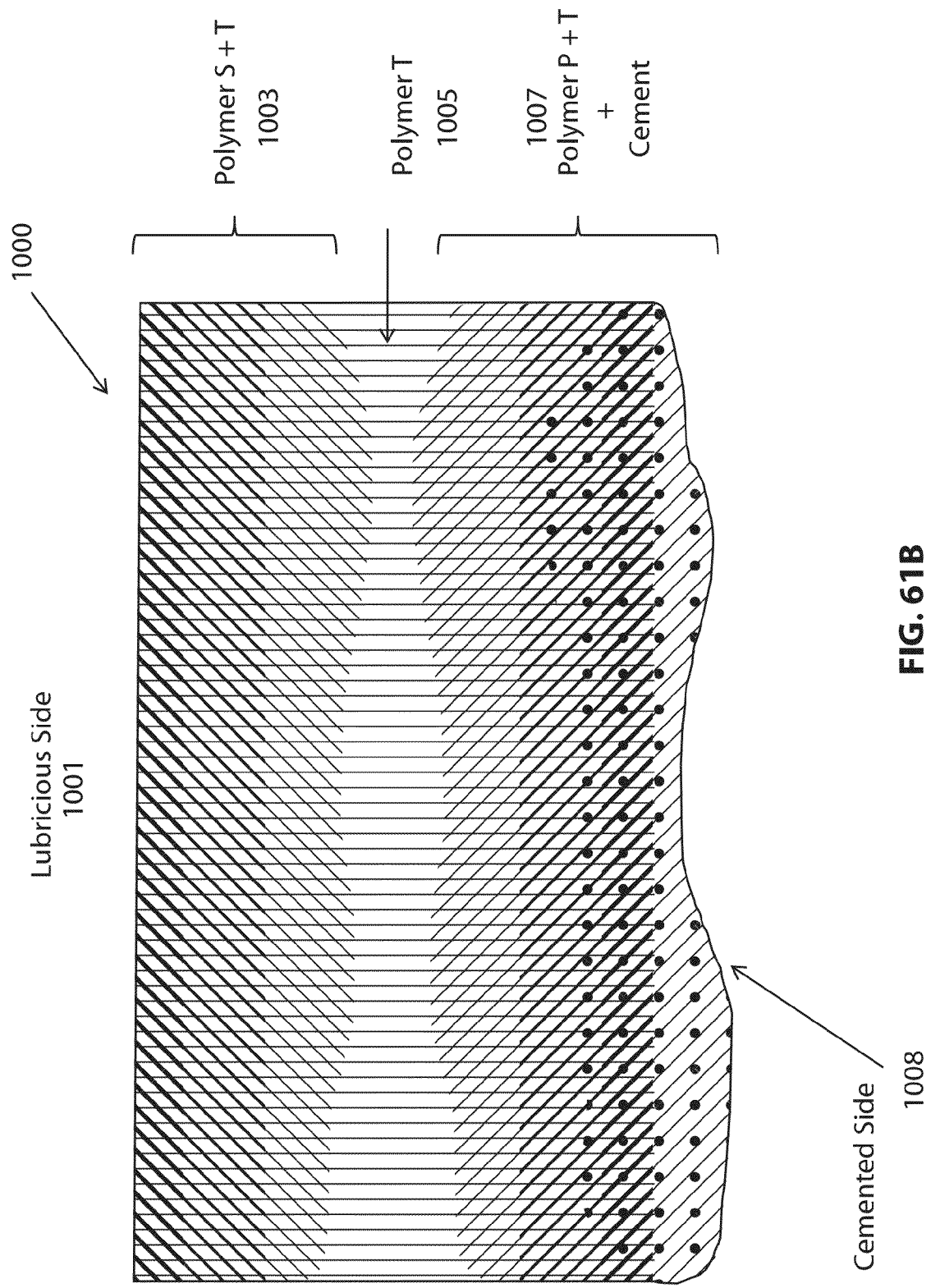

FIGS. 61A-61B illustrate one embodiment of a double gradient with a lubricious and adhesive gradient disposed on two different sides with a region of pure thermoset polymer 1005 between the gradients. The thermoset polymer material 1000 shown in FIGS. 61A and 61B has two gradients formed by two IPNs on two regions of the material 1000. The lubricious gradient is disposed in region 1003 and is formed from an IPN/semi-IPN made from a hydrophilic polymer S network within the thermoset polymer material T. The lubricious IPN area 1003 includes a surface section 1001 that provides a lubricious surface to engage with, for example, a joint region. On the other side of the material, is an adhesive gradient 1004 formed from an IPN/semi-IPN with a non-ionic polymer P network within the thermoset polymer material T. The adhesive IPN area 1004 includes a surface section 1002 that provides an adhesive surface to engage with bone through use of a cement 1006. As shown in FIG. 61A, the gradient regions 1003, 1004 and pure thermoset region 1005 are not separated in this embodiment by distinct boundaries. Rather, the regions gradually merge and transition from one to the other through a thickness of the material. For example, the concentration of the non-ionic polymer P network in region 1004 is shown as slanted lines that darken and widen from the pure thermoset region 1005 to the adhesive surface 1002. This shows that in some embodiments, the concentration of the non-ionic polymer P and the relative concentration of the adhesive gradient gradually increases from one region of the thermoset material to another without forming distinct boundaries between the sections. Similarly, on the lubricious side, the slanted lines showing the hydrophilic polymer S are wider and darker near the surface 1001 and gradually lighten as the slanted lines move toward the pure thermoset region 1005. This also shows that in some embodiments, the concentration of hydrophilic polymer S is greater at the surface 1001 and gradually diminishes through a thickness of the material toward region 1005. FIG. 61B further illustrates that in some embodiments, once the cement or anchoring compound 1006 is applied to the adhesive surface, the cement and the adhesive gradient merge to form a continuous region 1007 and a cemented side 1008 without distinct boundaries between the anchoring compound and the adhesive gradient 1004. In further embodiments, where the non-ionic polymer P in the cement 1006 and the adhesive IPN are the same (as indicated by the presence of the slanted lines in cement 1006 and region 1004), the non-ionic polymer P in the IPN and in the cement will merge and fuse to form a continuous composition.

FIGS. 62A-E show osteochondral grafts formed from a non-ionic IPN or semi-IPN of this invention that may be used singly or in any combination needed to replace or augment cartilage within a knee joint. FIG. 62A shows a osteochondral graft 1110 adapted to engage the femoral condyles (or alternatively, just one condyle). FIG. 62B shows osteochondral grafts 1111 and 1112 adapted to engage one or both sides of the tibial plateau 1113. FIG. 62C shows an osteochondral graft 1118 adapted to engage the patella 1114 and to articulate with an osteochondral graft 1119 adapted to engage the patellofemoral groove 1115. FIG. 62D show osteochondral grafts 1116 and 1117 adapted to engage the lateral and medial menisci. FIG. 62E shows how some of these prostheses may be assembled in place within the knee joint. Any of the IPNs/semi-IPNs as described and contemplated herein can be used with grafts such as those in FIGS. 62A-E to provide advantageous properties such as adhesiveness, stiffness, lubricity, conductivity, etc.

Moreover, in some embodiments, gradients such as those described in FIGS. 61A-B are employed where applicable to provide a lubricious and an adhesive gradient in the graft. For example, osteochondral graft 1110 can contain an adhesive surface and adhesive gradient on the portion of the graft adapted to engage the bone surface of the femoral condyles. Osteochondral graft 1110 may also include a lubricious surface and lubricious gradient to engage the tibial plateau 1113. As shown in FIG. 62B, the tibial plateau 1113 may also include osteochondral grafts 1111 and 1112 that can contain double gradients as described including an adhesive gradient with an adhesive surface on a tibia bone interfacing surface and a lubricious gradient and lubricious surface on a joint interfacing surface. Similarly, the gradients as described can be used in any, some, or all of the described grafts in FIGS. 62A-E.

In a further example, FIG. 63 shows two sides of a generic articular joint with both sides of the joint replaced with components or devices of the current disclosure. Concave bony prominence 1010 has a bone interface 1012 which accepts a concave articular component 1014. Convex bony prominence 1016 has a bone interface 1017 which accepts a convex articular component 1018. Concave component articular component 1014 mates with convex articular component 1018 at articular interface 1020. Any of the components may include a cross section such as the cross section at 1022 with single or multiple IPNs/semi-IPNs as described (such as those in FIGS. 61A and 61B). For example, cross section 1022 may contain a lubricious gradient and a lubricious surface on the joint interface portion facing the joint interface region 1024 where articular components 1014 and 1018 meet at 1020. An adhesive surface and adhesive gradient may be disposed on the bone interfacing portion facing the bone interface 1012.

Figure 64:
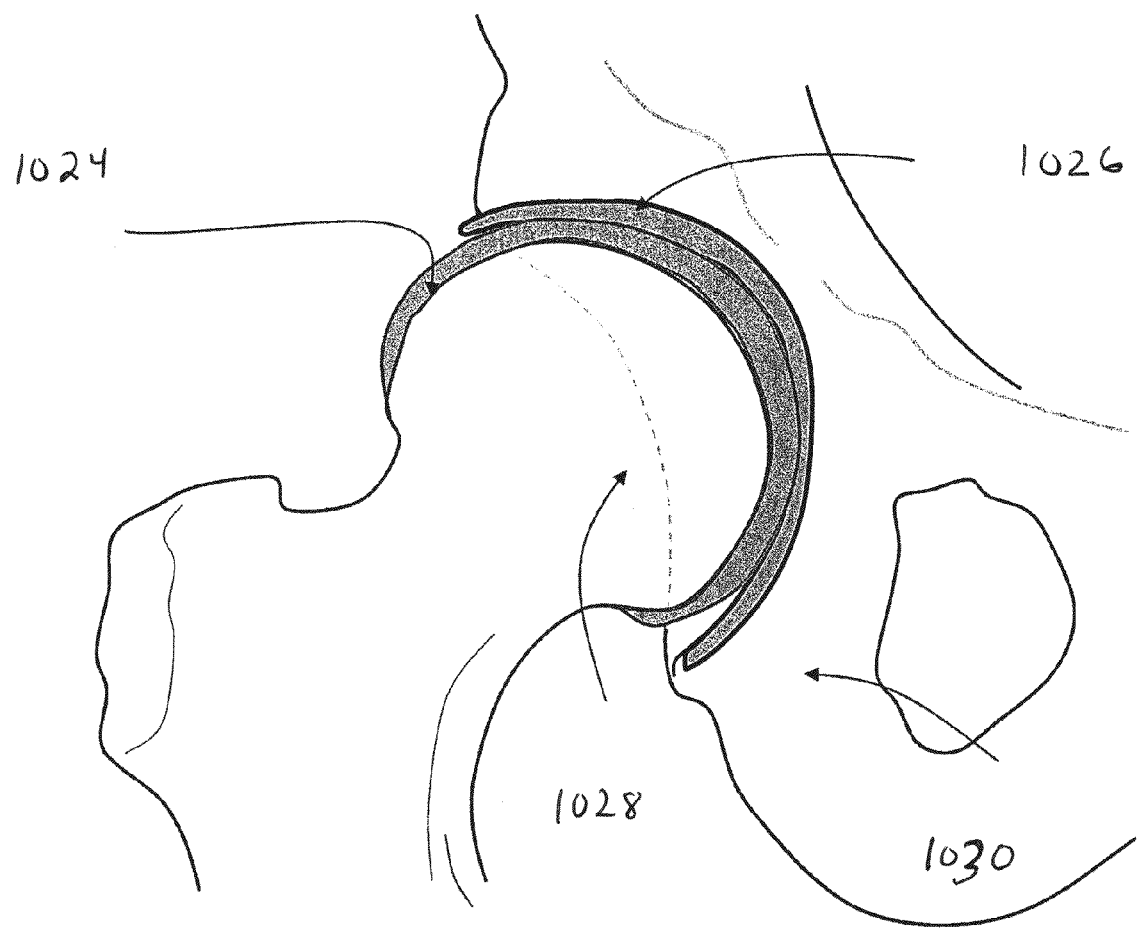
FIG. 64 illustrates cap-on-cup components with a convex articular component cap and a concave articular component cup according to embodiments of this invention.

FIG. 64 illustrates another embodiment with the placement of a cap-on-cup with a convex articular component cap 1024 over a femoral head 1028 and a concave articular component cup 1026 facing an acetabulum 1030 without the synthetic joint capsule and synthetic labral components in place. These components can be made with the thermoset/thermoplastic polymer materials with the IPN(s)/semi-IPN(s) and gradient(s) described. One or more of these components can include gradients such as those shown in FIGS. 61A and 61B.

Figure 65:
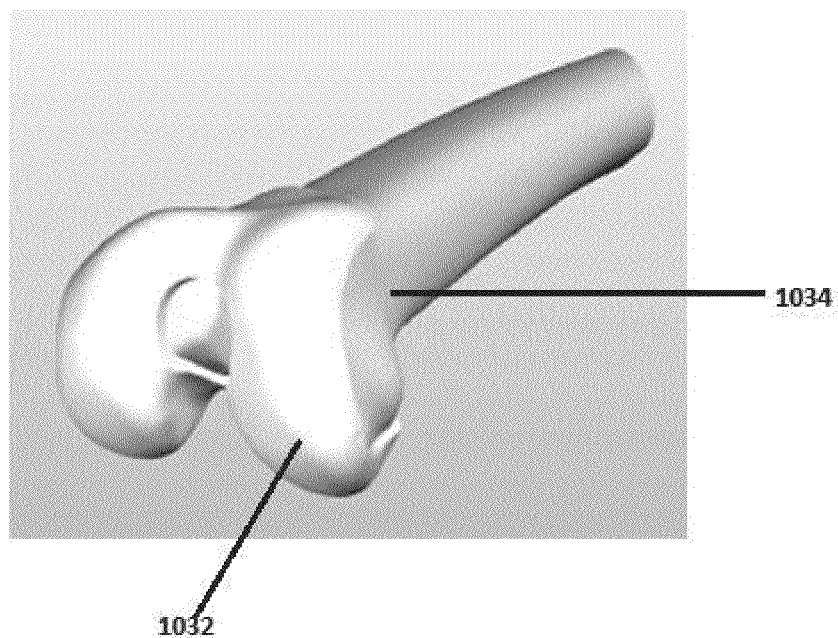
FIG. 65 illustrates an osteochrondral graft formed to fit over a surface of a femur.

The components and devices described can be formed into any number of designs for use such as grafts, patches, plugs, and total surface replacement. For example, FIGS. 65-68 provide examples of shapes employed with various embodiments. FIG. 65 shows an osteochrondral graft formed to fit over a surface of a femur. The device is formed as a patch 1032 to cover the femoral condyles of femur 1034. The patch 1032 may contain one or more IPNs/semi-IPNs that provide a gradient (or gradients) through a region(s) of the patch 1032. For example, the patch 1032 may contain an adhesive surface on the bone interfacing surface to facilitate affixing the patch 1032 to the femoral condyles via an anchoring agent.

Figure 66A:
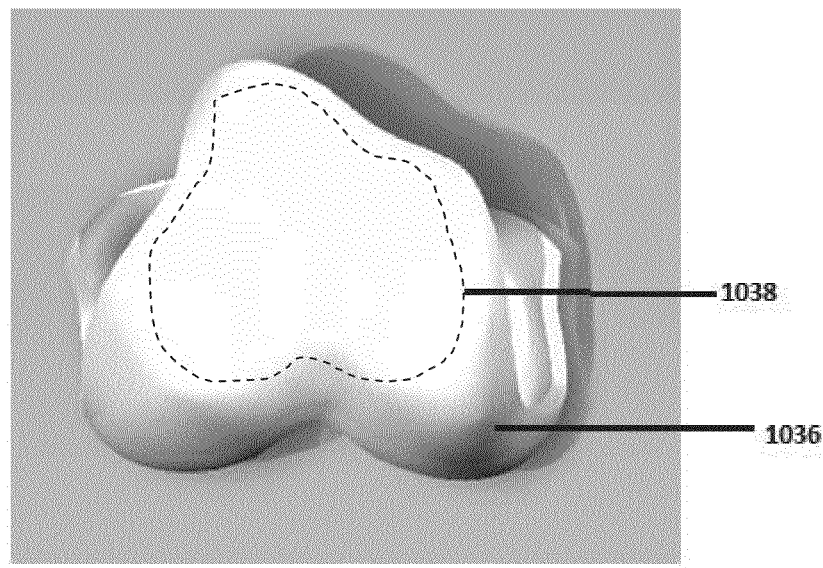
FIGS. 66A-B illustrate examples of osteochrondral grafts formed to fit as patches or plugs.
Figure 66B:
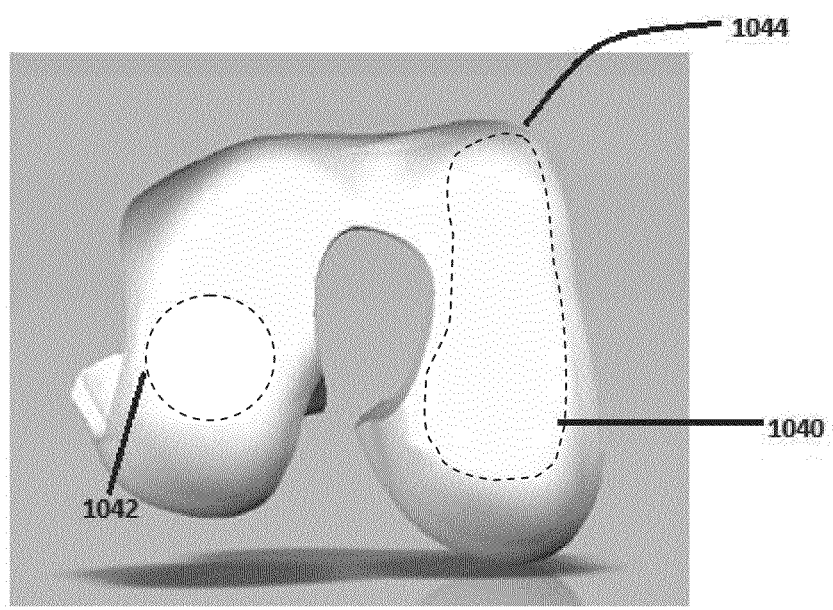

In further embodiments, the graft, patch, plug, etc. may be implants or devices designed to partially cover or replace cartilage surface. FIGS. 66A and 66B illustrate examples of various forms of osteochrondral grafts that provide partial replacement. FIG. 66A illustrates a smaller graft 1038 that may be used in lieu of larger graft 1036 to resurface the patellofemeroal groove. Similarly, FIG. 66A shows a plug 1042 and a smaller patch 1040 that can be used to replace a region of the femoral condyles as an alternative to a larger patch 1044.

Figure 67:
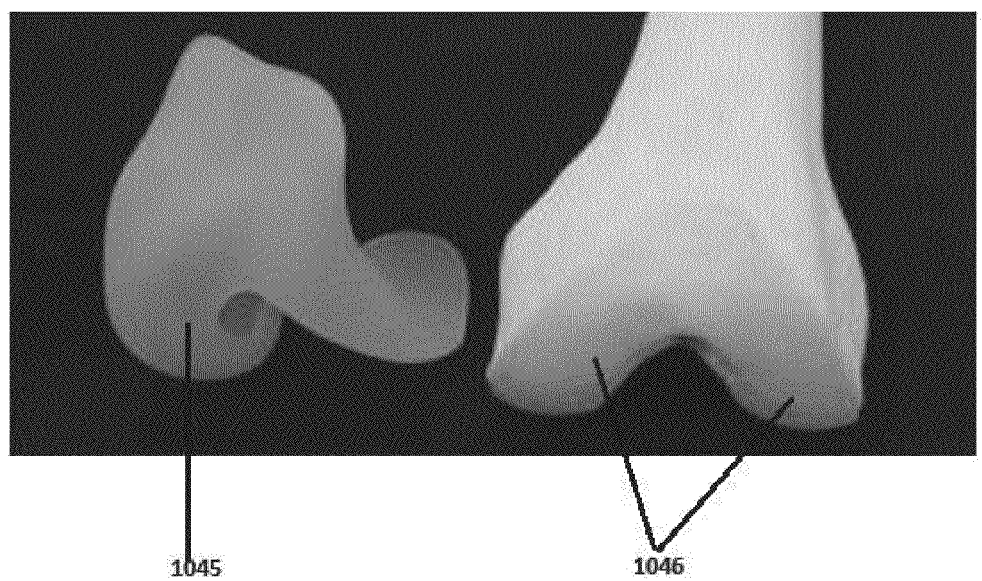
FIG. 67 illustrates a full distal femoral cartilage replacement component according to embodiments of this invention.

Additionally, FIG. 67 illustrates a full distal femoral cartilage replacement component according to embodiments of this invention where the graft 1045 is placed over the distal surface 1046 of the femur.

Figure 68:
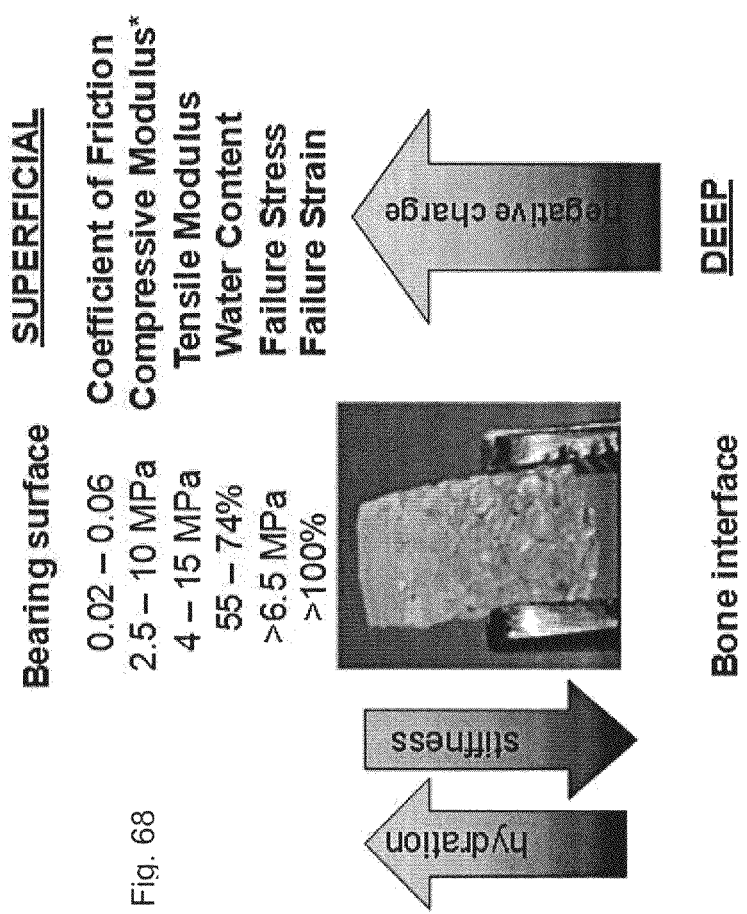
FIG. 68 illustrates an osteochrondral graft having a stiffness and hydration gradient.

FIG. 68 provides another example of an osteochrondral plug with a lubricious gradient and a stiffness gradient that are disposed on different sides with overlapping regions.

In some embodiments, an osteochrondral graft such as a plug with one or more IPNs/semi-IPNs may also include a porous bone interfacing material. The porous bone interfacing layer can be added to a bone interfacing portion of a device to facilitate bone ingrowth and integration. In some embodiments, a lubricious, cartilage-like synthetic region and surface may be disposed on one side of the graft and an adhesive bone interfacing region and surface may be anchored to another side. The adhesive bone interfacing region may further include a porous bone or a synthetic, porous bone-like structure. In one embodiment, the lubricious region consists of an interpenetrating polymer network that is composed of two polymers. The first polymer may be a hydrophobic thermoplastic with high mechanical strength, including but not limited to polyether urethane, polycarbonate urethane, silicone polyether urethane, and silicone polycarbonate urethanes, or these materials with incorporated urea linkages, or these materials with incorporated urea linkages (e.g. polyurethane urea). The second polymer may be a hydrophilic polymer derived from ionizable, vinyl monomers, including but not limited to acrylic acid and/or sulfopropyl methacrylate.

The adhesive region may consist of another interpenetrating polymer network that is composed of the same hydrophobic thermoplastic polymer of the lubricious region and a non-ionic polymer such as PMMA. A porous bone interface material, such as the one shown in FIG. 69 may be applied to the surface of the adhesive region to help facilitate attachment of the graft with the target bone location. In further embodiments, the porous bone interface material may itself contain IPNs/semi-IPNs or gradients.

Figure 72:
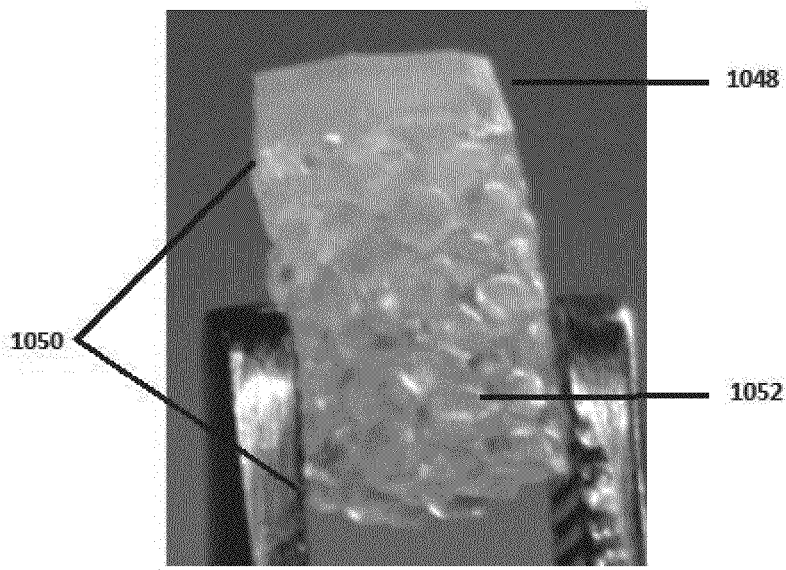
FIG. 72 illustrates a synthetic osteochondral plug with a porous bone-interfacing material.
Figure 73:
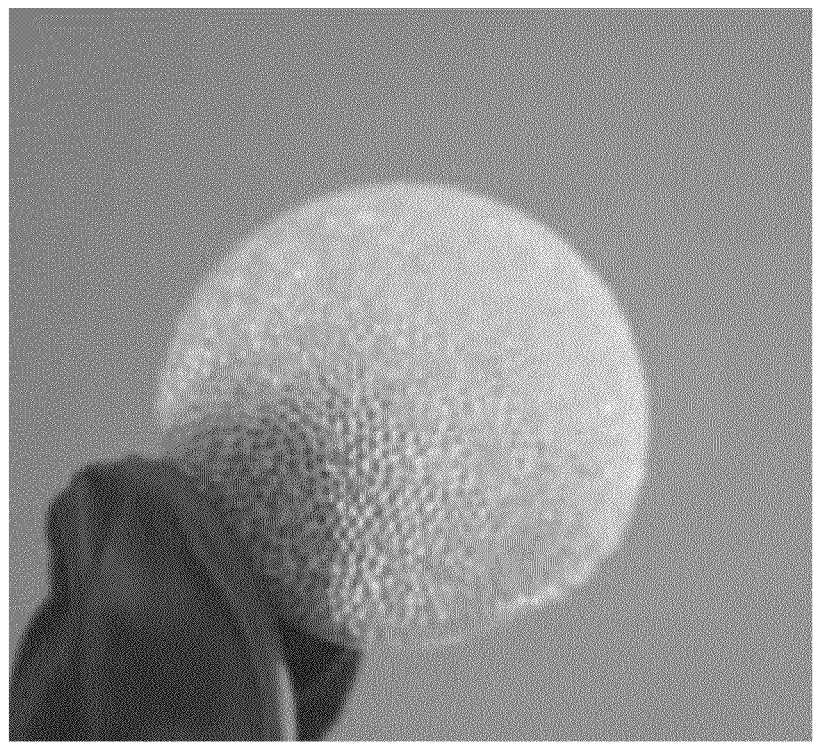
FIG. 73 illustrates an injection-molded hemispherical shell with porous backing.
Figure 74A:
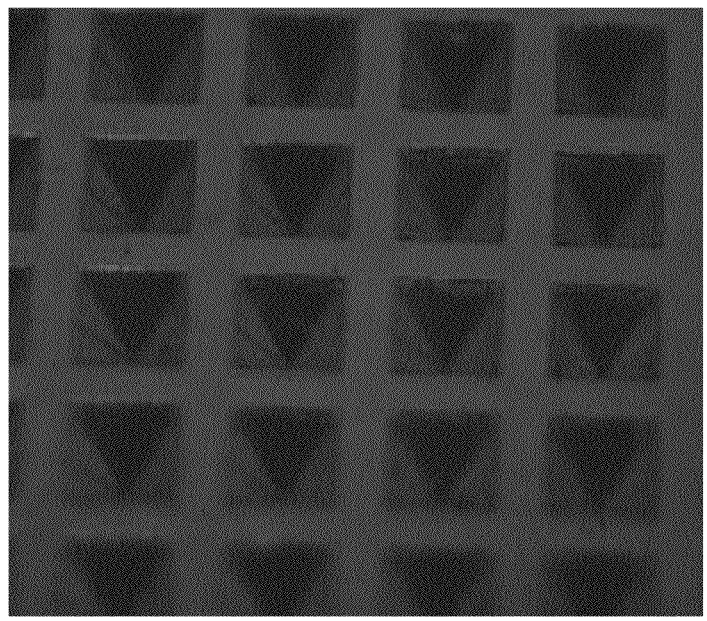
FIGS. 74A-B illustrate an injection-molded design with pyramidal surface feature indentations.
Figure 74B:
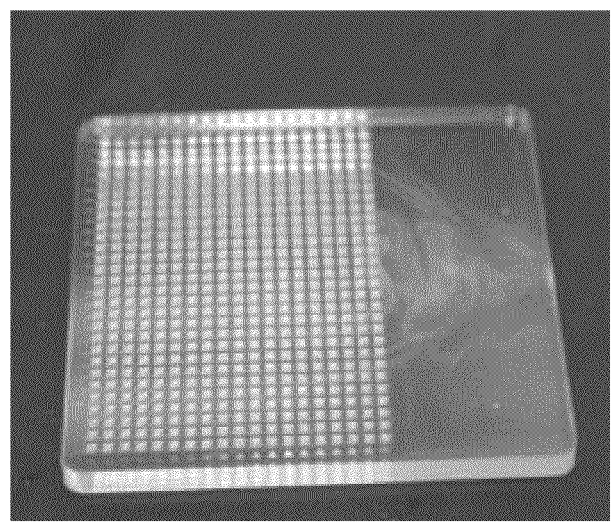

In further examples, the devices and components of the embodiments described may include a porous bone-interfacing material or layer such as the ones shown in FIGS. 72-75. In FIG. 72, a synthetic osteochondral plug consists of a lubricious, cartilage-like bearing surface 1048 that transitions to a bone-interface region 1050 with a porous surface 1052 to facilitate bone ingrowth. FIG. 73 provides an example of an injection molded hemispherical shell with a porous backing. FIG. 74A provides an example of an injection-molded design with pyramidal surface feature indentations. FIG. 74B provides an enlarged view of the pyramidal surface features on 74A. As discussed, these porous bone-interfacing materials can be used with any of the devices, components, and materials described herein (including those with one or more IPNs/semi-IPNs and gradients).

Figure 75A:
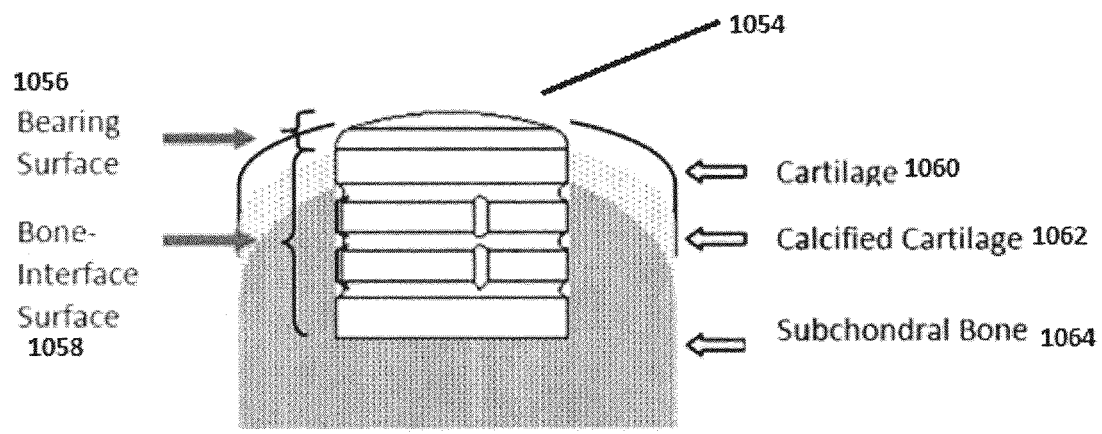
FIGS. 75A-C illustrate an osteochrondral plug according to embodiments of this invention.
Figure 75B:
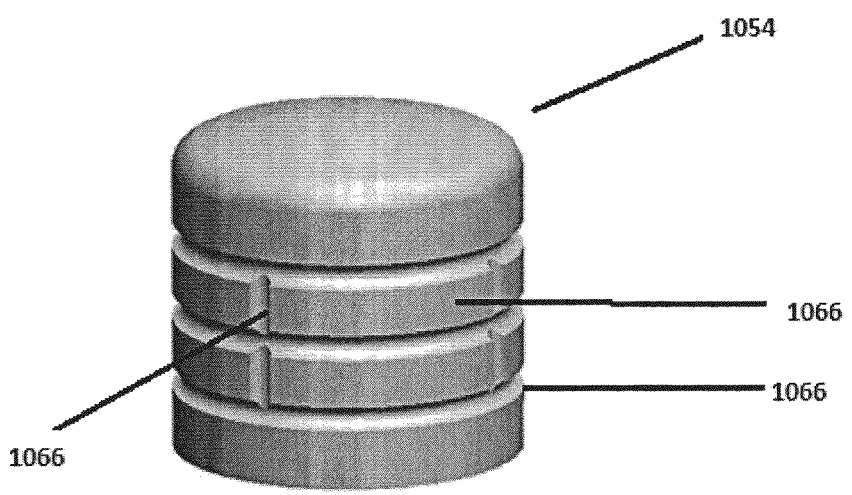
Figure 75C:
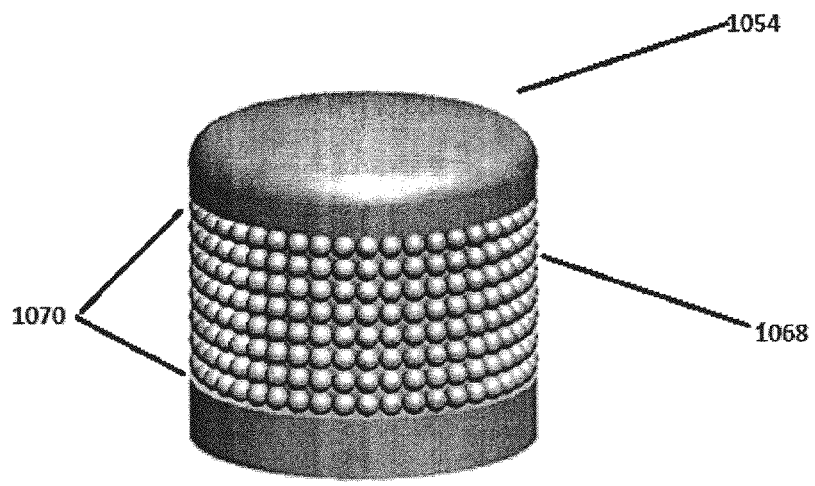

FIG. 75A-C provide a further osteochrondral plug embodiment of the described invention. FIG. 75A shows the cross section of plug 1054. The plug 1054 has a bearing surface 1056 and a bone interfacing surface 1058. The plug is implanted through a layer of cartilage 1060, calcified cartilage 1062, and subchondral bone 1064. In some embodiments, the curvature of the bearing surface 1054 will match that of the cartilage 1060 at the implantation site to minimize contact stresses in the apposing cartilage. The outer edge has a greater curvature to avoid "catching" during sliding-contact and to facilitate cartilage growth toward the device. The plug 1054 may also contain one or more IPNs/semi-IPNs and gradients.

FIG. 75B provides the osteochrondral plug of FIG. 75A with a bone-interface surface with the addition of larger grooves 1066 (depth=750 µm, width=1500 µm) to enhance biologic fixation. FIG. 75C shows the plug of FIG. 75A further including a porous bone-interfacing surface 1070 made from sintered beads 1068. In some embodiments the pore size is approximately 100-400 µm.

Furthermore, although the starting polymers have been described as hydrophobic thermoset or thermoplastic polymers, other suitable starting polymers known in the art such as polyethylene glycol or polyvinyl alcohol may be used as a starting material.

Another aspect of the present invention relates to a group of new polyurethane structures (polyurethane-polyacrylic acids; PU-PAA) and their IPNs which provide superior hydrolytical resistance, oxidative stability and creep resistance through covalently bonded crosslinks. In further embodiments, medical devices such as prostheses for a body, including joint prostheses are made from these materials.

In some embodiments, the new group of polyurethane structures may form polyurethane precursor material with structural integrity similar to Elasthane™ grade polyurethanes, such as resistance to hydrolysis and/or oxidation and/or creep; allow for cross linking with a subsequently added second network that is formed by polymerizing acrylic acid that has previously swollen the polyurethane; and/or allow for subsequent covalent bond formation between antioxidant(s) and polyurethane soft segment (s) after the acrylic acid polymerization.

Although a commercially available polyurethane product, Elasthane, Bionate, Pursil, or Sylgard, was used in some examples as a suitable polyurethane hydrophobic thermoset/thermoplastic polymer, it is understood in the art that any suitable polyurethane containing material may be used and there is no limitation as to the particular commercial products/tradenames described herein.

Figure 76:
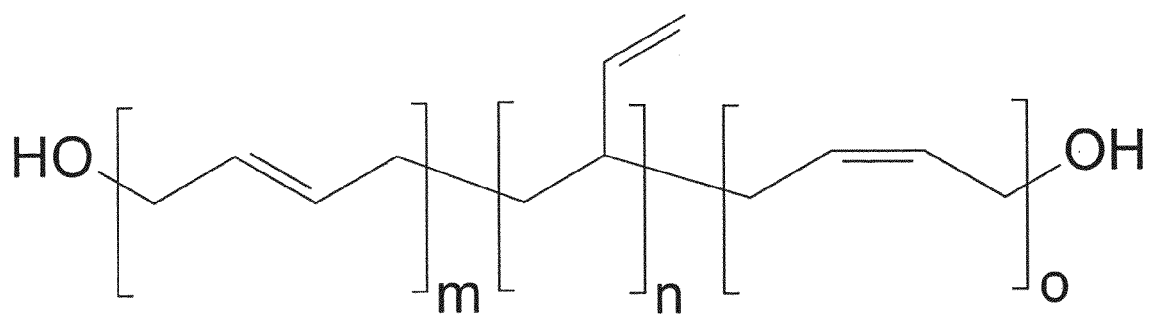
FIG. 76 shows a representation of the chemical structure for a hydroxy-terminated polybutadiene (HTPB).
Figure 77:
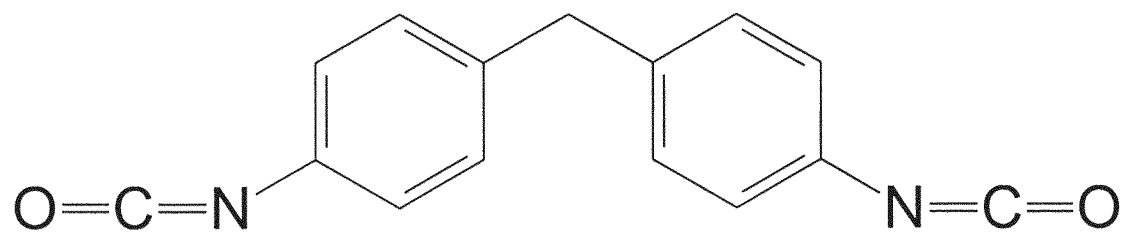
FIG. 77 shows a representation of the chemical structure for a bis-methylenediphenyl diisocyanate (MDI).

In some embodiments, example raw materials for the new group of polyurethane structures contemplated are hydroxyterminated polybutadiene (HTPB) (FIG. 76) and bis-methylenediphenyl diisocyanate (MDI) (FIG. 77). Alternatively, any other isocyanate(s) can be used, such as HDI, TDI, etc. In addition, any other diol(s) may be used with and without the dangling vinyl group. The diol may have a double bond in the chain.

Moreover, alternatively, mixtures of HTPB and PTMO or PEG can be used with a concentration that varies from 1-99%. PTMO: polytetramethyleneoxide, PEG: polyethylene glycol.

In some variations, the polymers are prepared according to the following reactions:

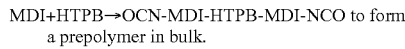

MDI+HTPB→OCN-MDI-HTPB-MDI-NCO to form a prepolymer in bulk.

Any solvent or mixture of solvents may be used to form the prepolymer (e.g. dimethylacetamide (DMAC), dimethylformamide (DMF), dimethylsulfoxide (DMSO), or toluene). The prepolymer is then chain-extended with diols such as butanediol (BD). Any diol or a mixture of diols can be used. The relative ratio of HTPB and PTMO or other soft segment (diol) and/or the molecular weight of the HTPB can be adjusted in order to provide final PUs with desired mechanical properties.

Figure 79:
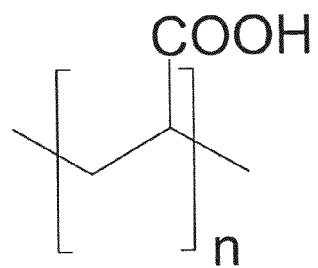
FIG. 79 shows a representation of the chemical structure for a polyacrylic acid.
Figure 80:
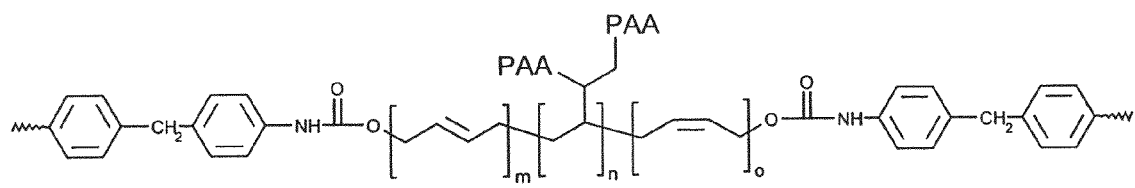
FIG. 80 shows a representation of the chemical structure for a material having polyacrylic acid copolymerized with HTPB.

In some embodiments, the resultant PU is soaked with a mixture of aqueous acrylic acid, (photo) initiator and crosslinker and polymerized using any method (e.g. ultraviolet (UV) light, thermal energy, atomic transfer radical polymerization (ATRP), reversible addition-fragmentation chain transfer (RAFT), emulsion polymerization) to form a hybrid of semi-IPN and IPN. PAA (FIG. 79) is spontaneously copolymerized with the dangling vinyl group on the (HTPB) chain to form the material shown in FIG. 80.

Figure 78:
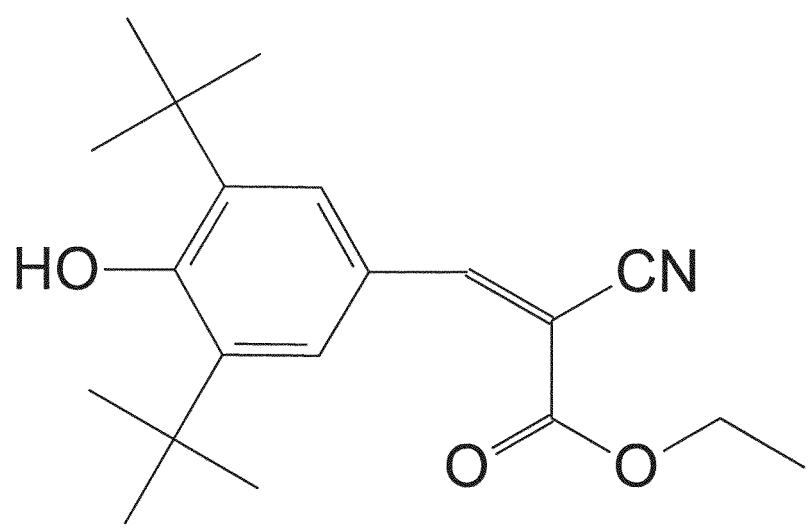
FIG. 78 shows a representation of the chemical structure for a hindered-phenol acrylate.

Any initiator and any cross-linker soluble in the acrylic acid solution may be used. The initiator maybe any, e.g. a photo or thermal initiator (2-hydroxy-2-methylpropiophenone, AIBN, 4,4'-azobis(4-cyanovaleric acid), V-501 by Wako, or V-44 (Wako). The cross-linker may be any e.g. bis-acylamide, bis-acrylate, bis-methyacrylate, PEG-diacrylate, or divinylether. The IPN is further modified with an antioxidant such as a hindered-phenol acrylate as shown in FIG. 78. Any antioxidant that has a double bond may be used.

Figure 81:
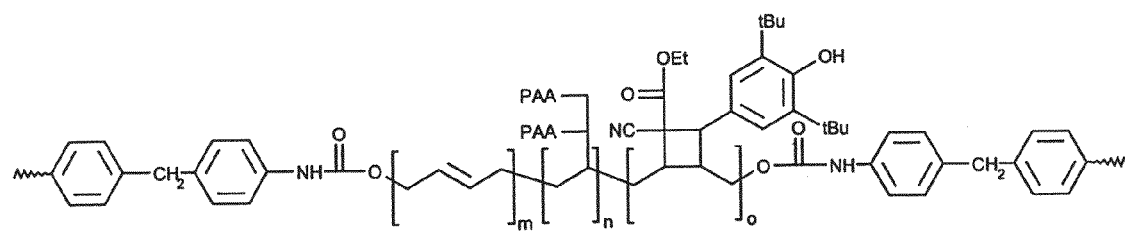
FIG. 81 shows a representation of the chemical structure for an IPN having a covalently bonded antioxidant.

The antioxidant can be covalently bonded to the PU-PAA described in this disclosure through a [2+2] cycloaddition with the —C=C— bonds on the HTPB. A covalently bonded antioxidant will not leach out throughout life time of a medical device made out of the PU-PAA IPN using UV irradiation. The final structure of the end material is shown in FIG. 81.

In some embodiments, the resultant material has some or all of the following superior properties: excellent hydrolytical stability; excellent oxidative stability; superior hard segment integrity, reducing the creep and increasing device dimensional stability; extremely low cell adhesion; extremely low protein absorption; better biocompatibility; and no PAA leaching during the lifetime of the device.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A composition of matter adapted to comprise one or more surfaces including an exterior surface of a medical implant comprising:
a first IPN or semi-IPN comprising a non-ionic polymer P and a hydrophobic thermoset or thermoplastic polymer T, and a second IPN or semi-IPN comprising the same said hydrophobic thermoset or thermoplastic polymer T and a hydrophilic interpenetrating polymer S.

2. The composition of claim 1 wherein P is derived from an ethylenically unsaturated monomer without ionizable functional groups.

3. The composition of claim 1 wherein T is a polyurethane containing polymer.

4. The composition of claim 1 wherein S is an ionic polymer.

5. The composition of claim 1 wherein P is polymethylmethacrylate and T is polyurethane.

6. The composition of claim 1 wherein the first IPN or semi-IPN is disposed in a first section of the said hydrophobic thermoset or thermoplastic polymer and the second IPN or semi-IPN is disposed in a second section of the said hydrophobic thermoset or thermoplastic polymer.

7. The composition of claim 1 wherein the non-ionic polymer P forms a concentration gradient from a first portion of the composition to a second portion of the composition.

8. The composition of claim 1 wherein the non-ionic polymer P forms a concentration gradient from a first portion of the first IPN or semi-IPN to a second portion of the first IPN or semi-IPN.

9. The composition of claim 1 wherein the hydrophilic interpenetrating polymer S forms a concentration gradient from a first portion of the composition to a second portion of the composition.

10. The composition of claim 1 wherein the hydrophilic interpenetrating polymer S forms a concentration gradient from a first portion of the second IPN or semi-IPN to a second portion of the second IPN or semi-IPN.

11. The composition of claim 1 further comprising at least two concentration gradients, wherein the non-ionic polymer P forms a first concentration gradient from a first portion of the composition to a second portion of composition and the hydrophilic interpenetrating polymer S forms a second concentration gradient from a third portion of the composition to a fourth portion of the composition.

12. The composition of claim 11 wherein the first concentration gradient provides an adhesiveness gradient within the composition.

13. The composition of claim 11 wherein the second concentration gradient provides a lubricious gradient within the composition.

14. The composition of claim 11 wherein the first concentration gradient provides a stiffness gradient within the composition.

15. The composition of claim 11 wherein the first concentration gradient provides a strength gradient within the composition.

16. The composition of claim 11 wherein the first concentration gradient provides an adhesiveness gradient and the second concentration provides a hydration gradient.

17. The composition of claim 11 wherein the first concentration gradient and the second concentration gradient partially or fully overlap.

18. The composition of claim 1 further comprising a region of the hydrophobic thermoset or thermoplastic polymer T that is disposed adjacent to an IPN or semi-IPN, wherein the region of the hydrophobic thermoset or thermoplastic polymer T does not contain a polymer P or S.

19. A composition of matter adapted to comprise one or more surfaces including an exterior surface of a medical implant comprising:
at least two IPNs or semi-IPNs, wherein a first IPN or semi-IPN comprises a hydrophobic thermoset or thermoplastic polymer and a non-ionic polymer and a second IPN or semi-IPN comprises a hydrophobic thermoset or thermoplastic polymer and a hydrophilic interpenetrating polymer.

20. A medical implant comprising a single body comprising a bone interfacing surface, a joint interfacing surface, a first IPN or semi-IPN comprising a non-ionic polymer P and a hydrophobic thermoset or thermoplastic polymer T being adjacent to the bone interfacing surface, and a second IPN or semi-IPN comprising the same said hydrophobic thermoset or thermoplastic polymer T, and a hydrophilic interpenetrating polymer S adjacent to the joint interfacing surface;
wherein the first IPN or semi-IPN and the second IPN or semi-IPN are between the bone interfacing surface and the joint interfacing surface.

21. The medical implant of claim 20 further comprising at least two concentration gradients are between the bone interfacing surface and the joint interfacing surface, wherein the non-ionic polymer P forms a first concentration gradient from a first portion of the implant to a second portion of the implant and the hydrophilic interpenetrating polymer S forms a second concentration gradient from a third portion of the implant to fourth portion of the implant;
wherein the first, second, third and fourth portions are between the bone interfacing surface and the joint interfacing surface.

22. The medical implant of claim 21 wherein the first concentration gradient provides an adhesiveness gradient and the second concentration gradient provides a lubricious gradient.

23. The medical implant of claim 20 wherein the non-ionic polymer P is derived from an ethylenically unsaturated monomer without ionizable functional groups.

24. The medical implant of claim 20 wherein the non-ionic polymer P is a constituent of a bone cement.

25. The medical implant of claim 20 wherein the non-ionic polymer P is selected from the group consisting of polymethylmethacrylate and polystyrene.

26. The medical implant of claim 20 wherein the hydrophobic thermoset or thermoplastic polymer T is a polyurethane polymer.

27. The medical implant of claim 20 wherein the first IPN or semi-IPN exhibits greater adhesiveness than the hydrophobic thermoset or thermoplastic polymer T.

28. The medical implant of claim 20 wherein the first IPN or semi-IPN exhibits greater stiffness than the hydrophobic thermoset or thermoplastic polymer T.

29. The medical implant of claim 20 wherein the first IPN or semi-IPN exhibits greater shear strength than the hydrophobic thermoset or thermoplastic polymer T.

30. The medical implant of claim 20 wherein the first IPN or semi-IPN exhibits greater adhesiveness than the hydrophobic thermoset or thermoplastic polymer T and the second IPN or semi-IPN exhibits greater lubriciousness than the hydrophobic thermoset or thermoplastic polymer T.

31. The medical implant of claim 21, wherein the first and second gradient partially or fully overlap.

32. The medical implant of claim 20 further comprising a region on the implant wherein the region is adjacent to the first and second IPN or semi-IPN and does not contain an IPN or semi-IPN.

33. A medical implant comprising a single body comprising a bone interfacing surface, a joint interfacing surface, and at least two IPNs or semi-IPNs, wherein a first IPN or semi-IPN comprises a non-ionic polymer disposed in at least one section of a hydrophobic thermoset or thermoplastic polymer, and a second IPN or semi-IPN comprises a non-ionic polymer disposed in at least one section of the said hydrophobic thermoset or thermoplastic polymer;
wherein the first IPN or semi-IPN and the second IPN or semi-IPN are between the bone interfacing surface and the joint interfacing surface, wherein the at least one sections are between the bone interfacing surface and the joint interfacing surface.

34. The composition of claim 1, wherein the non-ionic polymer is a constituent of a bone cement.

35. The composition of claim 1 wherein the hydrophobic thermoset or thermoplastic polymer is physically entangled with the non-ionic polymer.

36. The composition of claim 1 wherein the hydrophobic thermoset or thermoplastic polymer is chemically crosslinked to the non-ionic polymer.

37. The composition of claim 1 further comprising a bone cement, the bone cement comprising the non-ionic polymer P.

38. The composition of claim 18, wherein the region of the hydrophobic thermoset or thermoplastic polymer T that does not contain a polymer P or S is between the first IPN or semi-IPN and the second IPN or semi-IPN.

39. The medical implant of claim 20, wherein the bone interfacing surface and the joint interfacing surface of the implant are configured for a hip joint.

40. The medical implant of claim 33, wherein the bone interfacing surface and the joint interfacing surface of the implant are configured for a hip joint.

* * * * *